US009739783B1

(12) United States Patent
Kumar et al.

(10) Patent No.: US 9,739,783 B1
(45) Date of Patent: Aug. 22, 2017

(54) CONVOLUTIONAL NEURAL NETWORKS FOR CANCER DIAGNOSIS

(71) Applicant: Anixa Diagnostics Corporation, Los Angeles, CA (US)

(72) Inventors: Amit Kumar, San Jose, CA (US); John Roop, Ben Lomond, CA (US)

(73) Assignee: ANIXA DIAGNOSTICS CORPORATION, Los Angeles, CA (US)

( * ) Notice: Subject to any disclaimer, the term of this patent is extended or adjusted under 35 U.S.C. 154(b) by 0 days.

(21) Appl. No.: 15/209,616

(22) Filed: Jul. 13, 2016

Related U.S. Application Data

(60) Provisional application No. 62/308,763, filed on Mar. 15, 2016.

(51) Int. Cl.
G01N 33/574 (2006.01)
G01N 21/64 (2006.01)

(52) U.S. Cl.
CPC ... G01N 33/57492 (2013.01); G01N 21/6428 (2013.01); G01N 21/6458 (2013.01); G01N 33/57415 (2013.01); G01N 33/57449 (2013.01); *G01N 2021/6439* (2013.01); *G01N 2201/12* (2013.01); *G01N 2333/4742* (2013.01); *G01N 2333/705* (2013.01); *G01N 2333/70589* (2013.01)

(58) Field of Classification Search
None
See application file for complete search history.

(56) References Cited

U.S. PATENT DOCUMENTS

| 5,753,014 | A | 5/1998 | Van Rijn |
|---|---|---|---|
| 5,837,115 | A | 11/1998 | Austin et al. |
| 6,251,343 | B1 | 6/2001 | Dubrow et al. |
| 6,598,750 | B2 | 7/2003 | Tai et al. |
| 8,341,100 | B2 | 12/2012 | Miller et al. |
| 8,921,102 | B2 | 12/2014 | Fuchs et al. |
| 8,980,568 | B2 | 3/2015 | Lin et al. |
| 9,182,387 | B2 | 11/2015 | Goldkorn et al. |
| 2010/0105074 | A1 | 4/2010 | Covey et al. |
| 2011/0236903 | A1 | 9/2011 | McClelland et al. |
| 2012/0183946 | A1 | 7/2012 | Tang et al. |

(Continued)

FOREIGN PATENT DOCUMENTS

| CN | 103984958 A | 8/2014 |
|---|---|---|
| WO | WO-2011002649 A1 | 1/2011 |

(Continued)

OTHER PUBLICATIONS

Adams et al. Circulating Cancer-Associated Macrophage-Like Cells Differentiate Malignant Breast Cancer and Benign Breast Condition. Cancer Epidemiol Biomarkers Prev 25:1037-1042 (2016).

(Continued)

*Primary Examiner* — Rebecca Martinez
(74) *Attorney, Agent, or Firm* — Wilson Sonsini Goodrich & Rosati

(57) ABSTRACT

The present disclosure provides devices and systems for diagnosing and characterizing cancer in a subject. Devices include microfilters and microfiltration systems useful for the isolation and characterization of cells from a subject.

28 Claims, 42 Drawing Sheets
(25 of 42 Drawing Sheet(s) Filed in Color)

(56) References Cited

U.S. PATENT DOCUMENTS

| | | | | |
|---|---|---|---|---|
| 2012/0276555 | A1* | 11/2012 | Kuhn | G01N 33/5076 |
| | | | | 435/7.23 |
| 2013/0071876 | A1* | 3/2013 | Hao | G06K 9/00127 |
| | | | | 435/40.52 |
| 2013/0255361 | A1 | 10/2013 | Juncker et al. | |
| 2013/0266959 | A1 | 10/2013 | Kaiser et al. | |
| 2013/0309662 | A1 | 11/2013 | Park | |
| 2014/0030799 | A1 | 1/2014 | Yu et al. | |
| 2014/0178890 | A1* | 6/2014 | Kanbara | G01N 1/405 |
| | | | | 435/6.14 |
| 2015/0213302 | A1 | 7/2015 | Madabhushi et al. | |
| 2015/0356238 | A1 | 12/2015 | Sen et al. | |
| 2016/0136552 | A1* | 5/2016 | Nakanishi | B01D 37/00 |
| | | | | 210/695 |
| 2016/0169786 | A1 | 6/2016 | Albitar et al. | |
| 2017/0044265 | A1 | 2/2017 | Ahmadi et al. | |

FOREIGN PATENT DOCUMENTS

| | | | |
|---|---|---|---|
| WO | WO-2011139445 | A1 | 11/2011 |
| WO | WO-2013158045 | A1 | 10/2013 |
| WO | WO-2013181532 | A1 | 12/2013 |
| WO | WO2015012315 | * | 1/2015 |
| WO | WO-2015112932 | A1 | 7/2015 |
| WO | WO-2015177268 | A1 | 11/2015 |

OTHER PUBLICATIONS

Adams et al. Circulating giant macrophages as a potential biomarker of solid tumors. PNAS USA 111:3514-3519 (2014).

Brock et al. Liquid biopsy for cancer screening, patient startification and monitoring. Transl Cancer Res 4(3):280-290 (2015).

Byussens et al. Chapter 27. Multiscale Convolutional Neural Networks for Vision-Based Classification of Cells. Computer Vision—ACCV 2012, Part II, LNCS 7725, pp. 342-353 (2013).

Chen et al. Single-Cell Analysis of Circulating Tumor Cells. Cancer Biol Med 12:184-192 (2015).

Ciresan et al. Chapter 51. Mitosis Detection in Breast Cancer Histology Images with Deep Neural Networks. MICCAI 2013 8150:411-418 (2013).

Coumans et al. Filter Characteristics Influencing Circulating Tumor Cell Enrichment from Whole Blood. PLoS ONE 8(4):e61770 (2013).

Dong et al. Deep Learning for Automatic Cell Detection in Wide-Field Microscopy Zebrafish Images. 2015 IEEE 12th International Symposium on Biomedical Imaging (ISBI) (5 pgs.) (Apr. 16-19, 2015).

Faber et al. Activated macrophages containing tumor marker in colon carcinoma: immunohistochemical proof of a concept. Tumor Biol 33(2):435-441 (2012).

Harouaka et al. Circulating Tumor Cell Enrichment Based on Physical Properties. Journal of Laboratory Automation 18(6):455-468 (2013).

Kraus et al. Classifying and Segmenting Microscopy Images Using Convolutional Multiple Instance Learning. Bioinformatics 32(12):i52-i59 (2016).

Krombach et al. Cell Size of Alveolar Macrophages: An Interspecies Comparison. Environ Health Perspect 105(Supp 5):1261-1263 (1997).

Lu et al. A study of the autofluorescence of parylene materials for µTAS applications. Lab Chip 10:1826-1834 (2010).

Malon et al. Identifying histological elements with convolutional neural networks. Proceeding transdisciplinary science and technology. pp. 450-456 (2008).

Nagrath et al. Isolation of rare circulating tumour cells in cancer patients by microchip technology. Nature 450(7173):1235-1239 (2007).

Ranzato et al. Automatic Recognition of Biological Particles in Microscopic Images. Pattern Recognition Letters 28(1):31-39 (2007).

Romaszko. Signal Correlation Prediction Using Convolutional Neural Networks. JMLR: Workshop and Conference Proceedings 46:45-56 (2015).

Sanborn. Detection of fluorescent neuron cell bodies using convolutional neural networks. Stanford University—Final Report. (7 pgs.) (2015).

Schmid et al. Myeloid cell trafficking and tumor angiogenesis. Cancer Lett 250(1):1-8 (2007).

Sollier et al. Size-selective collection of circulating tumor cells using Vortex technology. Lab Chip 14(1):63-77 (2014).

Xie et al. Microscopy Cell Counting with Fully Convolutional Regression Networks. Department of Engineering Science, University of Oxford, UK. (8 pgs.) (no date provided).

Xu et al. A Cancer Detection Platform Which Measures Telomerase Activity from Live Circulating Tumor Cells Captured on a Microfilter. Cancer Res 70(16):6420-6426 (2010).

Zheng et al. 3D microfilter device for viable circulating tumor cell (CTC) enrichment from blood. Biomed Microdevices 13(1):203-213 (2011).

Zheng et al. Membrane microfilter device for selective capture, electrolysis and genomic analysis of human circulating tumor cells. J Chromatogr A 1162(2):154-161 (2007).

Recktenwald. Teaching Notes from Multidimensional Flow Cytometric Analysis of Bone Marrow and Peripheral Blood Stem Cells. J Hemother 2:387-394 (1993).

U.S. Appl. No. 15/445,913 Office Action dated Jun. 13, 2017.

* cited by examiner

DAPI

Ck 8,18,19

EpCAM

CD45

DAPI

Ck 8,18,19

EpCAM

CD45

DAPI

Ck 8,18,19

EpCAM

CD45

CONVOLUTIONAL NEURAL NETWORKS FOR CANCER DIAGNOSIS

CROSS-REFERENCE

This application claims the benefit of U.S. provisional application Ser. No. 62/308,763, filed Mar. 15, 2016, which is incorporated by reference herein in its entirety.

BACKGROUND OF THE INVENTION

In the course of a lifetime, cancer will strike about one in three women and one in two men. More than 560,000 die from it each year in the United States alone. Early detection and treatment is currently the leading method to reduce cancer death, especially if the cancer is detected before metastasis. For nearly all types of cancer, the 5-year relative survival rate is substantially lower if the disease is caught at an advanced stage. Moreover, the financial costs of cancer treatment at an advanced stage can be an additional burden. By 2020, the cost of cancer treatment is expected to be $207 billion annually in the United States. Accordingly, early detection of cancer is important for increasing cancer survival rates and reducing the cost of treatment.

However, methods for early detection often lack sensitivity and generate numerous false positives, leading to additional unnecessary testing, which can include biopsies and other painful, stressful and expensive procedures. As a result, the overall health burden borne by test subjects who register as false positives can outweigh the benefits to those patients who benefit from early detection of their cancers. This is especially true for screening tests where the incidence of disease is low. Thus, there is a need for a cancer diagnostic test which produces an unambiguous result, is low cost and minimally invasive, and has few false positives. Such a test would be useful for recurrence testing, validation testing, and other situations where an initial indication of cancer needs to be verified before an expensive and aggressive follow up procedure is performed.

SUMMARY OF THE INVENTION

During tumor development and growth, there is a large increase of multiple types of white blood cells. A subset of these white blood cells are of myeloid origin and are found in the tumor stroma. These myeloid derived cells are mobile and capable of re-entering the blood stream after exposure to the tumor microenvironment. Myeloid derived cells which have come in contact with tumor cells, referred to herein as Tumor Derived Myeloid Cells (TDMCs), have unique morphologies and surface markers characteristic of tumor exposure.

Another class of cells which enter the blood stream from the tumor environment are Circulating Tumor Cells (CTCs), which are tumor cells that have detached from a solid tumor. CTCs are heterogeneous and include at least epithelial tumor cells, epithelial-to-mesenchymal transition (EMT) cells, hybrid (epithelial/EMT+) tumor cells, irreversible EMT+ tumor cells, and circulating tumor stem cells (CTSCs). Typically, CTCs are defined as cells with an intact viable nucleus, absence of CD45, and are cytokeratin positive and epithelial cell adhesion molecule (EpCAM) positive. Increasing evidence suggests that CTCs are responsible for metastatic relapse. Accordingly, CTCs have become an important biomarker for early cancer diagnosis, prognosis, and treatment monitoring.

Another class of tumor related cells are Tumor Associated Macrophages (TAMs). TAMs often have an M2 phenotype and show mostly pro-tumoral functions, promoting tumor cell survival, proliferation, and metastasization. High numbers of TAMs, in the stroma of a tumor, are frequently associated with an unfavorable prognosis. TAMs are also found at remote metastatic secondary tumor initiation sites, and may function in preparation of the initiation sites.

In various aspects, provided herein are systems and methods for the isolation and detection of tumor related cells such as TDMCs, CTCs and TAMs. Systems include microfiltration devices for cell enrichment as well as detection devices for identifying one or more features of the enriched cells. Further provided are methods for characterizing a tumor related cell as derived from a specific type of tumor by characterizing one or more features of the tumor related cell.

In one aspect, provided herein is a microfilter for filtering a biological sample, the microfilter comprising a biologically compatible metal layer and a plurality of pores extending through the metal layer; wherein each of the plurality of pores has a first diameter between about 1 and 50 microns. In some embodiments, the first diameter is between about 4 and 30 microns. In some embodiments, the first diameter is between about 4 and 15 microns. In some embodiments, one or more of the plurality of pores has a second diameter of between about 6 and about 100 microns. In some embodiments, the first diameter is between about 1 and about 12 microns and the second diameter is between about 6 and about 50 microns. In some embodiments, the metal layer has an autofluorescence less than parylene-C filter material in the FITC, TRITC, and Cy5 fluorescent channels used in fluorescence microscopy, by relative measurement. In some embodiments, the metal layer has an autofluorescence that is less than about 80%, 70%, 60%, 50%, 40%, 30%, 20%, 10%, or 5% of the autofluorescence of parylene-C in the FITC, TRITC, and/or Cy5 fluorescent channels, by relative measurement. Commonly used and commercially available parylene types C, F, A, AM, N and D are widely used as a biocompatible material for microfluidics, with parylene-C being the most widely used. Parylene is a trade name for a class of poly(p-xylylene) polymers. Paraylene-C is formed of repeating units of the structure

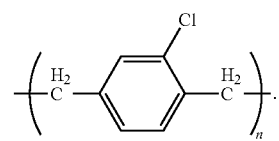

In some embodiments, the metal layer comprises titanium, nickel, gold, silver, cobalt, chromium, copper, iron, manganese, platinum, zinc, palladium, molybdenum, tungsten, aluminum, indium, carbon, silicon, tin, lead or an alloy or combination thereof. In some embodiments, the metal layer comprises nickel or an alloy thereof. In some embodiments, the metal layer comprises palladium or an alloy thereof. In some embodiments, the metal layer comprises nickel, palladium or a combination thereof, the metal layer having an autofluorescence that is less than about 50%, 40%, 30%, 20%, or 10% of parylene-C in the FITC fluorescent channel. In some embodiments, the metal layer comprises nickel, palladium or a combination thereof, the metal layer having an autofluorescence that is less than about 50%, 40%, 30%, 20%, or 10% of parylene-C in the TRITC fluorescent channel. In some embodiments, the metal layer comprises nickel, palladium or a combination thereof, the metal layer having an autofluorescence that is less than about 50%, 40%, 30%, 20%, or 10% of parylene-C in the Cy5 fluorescent channel. In some embodiments, the microfilter withstands a pressure between about 10 mmHg and about 760 mmHg. In some embodiments, the tensile strength of the microfilter is greater than about 100 MPa. In some embodiments, the thickness of the microfilter greater than about 5 microns. In some embodiments, the microfilter is between about 5 and 100 microns thick. In some embodiments, the microfilter is between about 5 and 20 microns thick. In some embodiments, the diameter of the microfilter is between about 1 and about 30 millimeters. In some embodiments, the diameter of the microfilter is between about 2 and 15 millimeters. In some embodiments, a first pore of the plurality of pores is separated from a second pore of the plurality of pores by a distance of about 2 to about 24 microns. In some embodiments, the microfilter comprises a central region comprising the plurality of pores and an annular support ring extending beyond the central region. In some embodiments, the width of the annular supporting ring is between about 0.5 and about 4 millimeters. In some embodiments, the width of the central region is between about 5 and about 20 millimeters. In some embodiments, the density of the plurality of pores per square millimeter is between about 1 and about 10,000 pores. In some embodiments, a surface of the metal layer is functionalized with a biomolecule. In some embodiments, the biomolecule is a protein or nucleic acid that binds to a ligand of a target cell in the biological sample. In some embodiments, the biomolecule is a cytokine, antibody, or receptor.

Further provided are devices comprising the microfilter and a microfilter holder. In some embodiments, the microfilter is bonded to the microfilter holder. In some embodiments, the microfilter holder comprises an opening flanked by a rim. In some embodiments, a periphery of the microfilter is bonded to the rim of the microfilter holder. In some embodiments, the periphery of the microfilter does not comprise the plurality of pores and the plurality of pores is exposed to the opening of the microfilter holder. In some embodiments, the periphery comprises one or more pores. In some embodiments, the microfilter holder comprises glass or plastic. In some embodiments, the microfilter holder is a slide configured for use in fluorescence microscopy.

In another aspect, provided herein is a microfilter for filtering a biological sample, the microfilter prepared by a method comprising: (a) providing a mechanical support comprising a layer of conductive material and a plurality of pillars; (b) electroplating the layer of conductive material with a layer of metal; and (c) removing the layer of metal from the mechanical support to obtain the microfilter comprising the layer of metal and a plurality of pores within the metal layer, wherein the position of the plurality of pores corresponds to the position of the plurality of pillars on the mechanical support. In some embodiments, the layer of conductive material comprises titanium, gold, nickel, silver, cobalt, chromium, copper, iron, manganese, platinum, zinc, palladium, molybdenum, tungsten, aluminum, indium, carbon, silicon, tin, lead or an alloy or combination thereof. In some embodiments, the plurality of pillars comprises photoresist. In some embodiments, the photoresist is a positive photoresist. In some embodiments, the positive photoresist comprises AZ P4620. In some embodiments, the photoresist is spin-coated on the mechanical support. In some embodiments, the diameter of one or more of the plurality of pillars is between about 1 and about 50 microns. In some embodiments, a first diameter of one or more of the plurality of pores is between about 1 and about 50 microns. In some embodiments, the first diameter of one or more of the plurality of pores is between about 4 and 30 microns. In some embodiments, a second diameter of one or more of the plurality of pores is between about 6 and about 100 microns. In some embodiments, the layer of metal is between about 1 and about 100 microns in thickness. In some embodiments, the layer of metal is between about 5 and 20 microns in thickness. In some embodiments, the layer of metal comprises titanium, nickel, gold, silver, cobalt, chromium, copper, iron, manganese, platinum, zinc, palladium, molybdenum, tungsten, aluminum, indium, carbon, silicon, tin, lead or an alloy or combination thereof. In some embodiments, the layer of metal comprises nickel or an alloy thereof. In some embodiments, the layer of metal comprises palladium or an alloy thereof. In some embodiments, the metal layer has an autofluorescence less than parylene-C filter material in the FITC, TRITC, and Cy5 fluorescent channels used in fluorescence microscopy, by relative measurement. In some embodiments, the metal layer has an autofluorescence that is less than about 80%, 70%, 60%, 50%, 40%, 30%, 20%, 10%, or 5% of the autofluorescence of parylene-C in the FITC, TRITC, and/or Cy5 fluorescent channels, by relative measurement. In some embodiments, the microfilter withstands a pressure between about 10 mmHg and about 760 mmHg. In some embodiments, the tensile strength of the microfilter is greater than about 100 MPa. In some embodiments, the tensile strength of the layer of metal is greater than about 100 MPa. In some embodiments, the diameter of the microfilter is between about 1 and about 30 millimeters. In some embodiments, the diameter of the microfilter is between about 2 and 15 millimeters. In some embodiments, a first pore of the plurality of pores is separated from a second pore of the plurality of pores by a distance of about 2 to about 24 microns. In some embodiments, the microfilter comprises a central region comprising the plurality of pores and an annular support ring extending beyond the central region. In some embodiments, the width of the annular supporting ring is between about 0.5 and about 4 millimeters. In some embodiments, the width of the central region is between about 5 and about 20 millimeters. In some embodiments, the density of the plurality of pores per square millimeter is between about 1 and about 10,000 pores. In some embodiments, a surface of the metal layer is functionalized with a biomolecule. In some embodiments, the biomolecule is a protein or nucleic acid that binds to a ligand of a target cell in the biological sample. In some embodiments, the biomolecule is a cytokine, antibody, or receptor. In some embodiments, Further provided are devices comprising the microfilter prepared by any method herein and a microfilter holder. In some embodiments, the microfilter is bonded to the microfilter holder. In some embodiments, the microfilter holder comprises an opening flanked by a rim. In some embodiments, a periphery of the microfilter is bonded to the rim of the microfilter holder. In some embodiments, the periphery of the microfilter does not comprise the plurality of pores and the plurality of pores is exposed to the opening of the microfilter holder. In some embodiments, the periphery comprises one or more pores. In some embodiments, the microfilter holder comprises glass or plastic. In some embodiments, the microfilter holder is a slide configured for use in fluorescence microscopy.

In another aspect, provided herein is a method of preparing a microfilter for filtering a biological sample, the method comprising: (a) providing a mechanical support comprising a layer of conductive material; (b) applying a layer of photoresist on the layer of conductive material; (c) patterning the layer of photoresist to expose regions of the layer of conductive material, wherein the photoresist pattern comprises a plurality of pillars of photoresist; (d) electroplating the exposed regions of the layer of conductive material with a layer of metal to a height equal to or less than the height of each of the plurality of pillars; (e) dissolving the plurality of pillars of photoresist; and (f) separating the layer of metal from the mechanical support to obtain the microfilter, the microfilter comprising the layer of metal and a plurality of pores. In some embodiments, the mechanical support comprises a silicon wafer. In some embodiments, the silicon wafer has a thickness of between about 0.5 to about 6 inches. In some embodiments, the layer of conductive material comprises titanium, gold, or an alloy or combination thereof. In some embodiments, the layer of conductive material is deposited on the mechanical support by vapor deposition. In some embodiments, the photoresist is a positive photoresist. In some embodiments, the positive photoresist comprises AZ P4620. In some embodiments, the photoresist is spin-coated on the mechanical support. In some embodiments, separating the layer of metal from the mechanical support comprises underetching the conductive layer, thereby allowing the layer of metal to be released from the mechanical support. In some embodiments, the microfilter is cleaned by washing in an aqueous solution, organic solution or a combination thereof. In some embodiments, the microfilter is annealed. In some embodiments, the diameter of one or more of the plurality of pillars is between about 1 and about 50 microns. In some embodiments, a first diameter of one or more of the plurality of pores is between about 1 and about 50 microns. In some embodiments, the first diameter of one or more of the plurality of pores is between about 4 and about 30 microns. In some embodiments, a second diameter of one or more of the plurality of pores is between about 6 and about 100 microns. In some embodiments, the layer of metal is between about 1 and about 100 microns in thickness. In some embodiments, the layer of metal is between about 5 and 20 microns in thickness. In some embodiments, the layer of metal comprises titanium, nickel, gold, silver, cobalt, chromium, copper, iron, manganese, platinum, zinc, palladium, molybdenum, tungsten, aluminum, indium, carbon, silicon, tin, lead or an alloy or combination thereof. In some embodiments, the metal layer comprises nickel or an alloy thereof. In some embodiments, the layer of metal comprises nickel or an alloy thereof. In some embodiments, the layer of metal comprises palladium or an alloy thereof. In some embodiments, the metal layer has an autofluorescence less than parylene-C filter material in the FITC, TRITC, and Cy5 fluorescent channels used in fluorescence microscopy, by relative measurement. In some embodiments, the metal layer has an autofluorescence that is less than about 80%, 70%, 60%, 50%, 40%, 30%, 20%, 10%, or 5% of the autofluorescence of parylene-C in the FITC, TRITC, and/or Cy5 fluorescent channels, by relative measurement. In some embodiments, the microfilter withstands a pressure of at least about 100 MPa. In some embodiments, the tensile strength of the microfilter is greater than about 100 MPa. In some embodiments, the tensile strength of the metal layer is greater than about 100 MPa. In some embodiments, the diameter of the microfilter is between about 1 and about 30 millimeters. In some embodiments, the diameter of the microfilter is between about 2 and about 15 millimeters. In some embodiments, a first pore of the plurality of pores is separated from a second pore of the plurality of pores by a distance of about 1 to about 24 microns. In some embodiments, the microfilter comprises a central region comprising the plurality of pores and an annular support ring extending beyond the central region. In some embodiments, the width of the annular supporting ring is between about 0.5 and about 4 millimeters. In some embodiments, the width of the central region is between about 5 and about 20 millimeters. In some embodiments, the density of the plurality of pores per square millimeter is between about 1 and about 10,000 pores. In some embodiments, the method further comprises functionalizing a surface of the metal layer with a biomolecule. In some embodiments, the biomolecule is a protein or nucleic acid that binds to a ligand of a target cell in the biological sample. In some embodiments, the biomolecule is a cytokine, antibody, or receptor.

In another aspect, provided herein is a method of diagnosing cancer in a subject, the method comprising: (a) passing a biological sample from the subject through a microfilter comprising a metal layer and a plurality of pores extending through the metal layer; wherein a length of one or more of the plurality pores is smaller than a length of a target cell; and wherein if the biological sample comprises the target cell, retaining the target cell on a surface of the metal layer; (b) applying to the microfilter a probe comprising a ligand specific for a biomarker of the target cell; wherein if the target cell is retained on the surface of the metal layer, binding the probe to the target cell; and (c) detecting the presence or absence of the target cell by detecting the presence or absence of the probe bound to the target cell; wherein the presence of the target cell is indicative of cancer in the subject. In some embodiments, the biomarker is cytokeratin 8, cytokeratin 18, cytokeratin 19, EpCAM, or a combination thereof. In some embodiments, the cancer is breast cancer. In some embodiments, the cancer is ovarian cancer. In some embodiments, the specificity for diagnosing cancer in the subject is greater than about 50%. In some embodiments, the selectivity for diagnosing cancer in the subject is greater than about 50%. In some embodiments, the biological sample is passed through the microfilter at a rate of between 0.1 and 15 milliliters per minute. In some embodiments, the biological sample has a volume between about 1 and about 15 milliliters. In some embodiments, the biological sample has a volume of about 7.5 milliliters. In some embodiments, the biological sample is whole blood, serum or plasma. In some embodiments, the biological sample is prepared prior to microfiltration by combination with a buffer, labeling reagent, anticlotting agent, fixing agent, or a combination thereof. In some embodiments, the length of one or more of the plurality of pores is between about 1 and about 50 microns. In some embodiments, the length of one or more of the plurality of pores is between about 4 and about 30 microns. In some embodiments, the metal layer is between about 5 and about 100 microns in thickness. In some embodiments, the metal layer is between about 5 and about 100 microns in thickness. In some embodiments, the metal layer comprises titanium, nickel, gold, silver, cobalt, chromium, copper, iron, manganese, platinum, zinc, palladium, molybdenum, tungsten, aluminum, indium, carbon, silicon, tin, lead or an alloy or combination thereof. In some embodiments, the metal layer comprises nickel or an alloy thereof. In some embodiments, the metal layer has an autofluorescence less than parylene-C filter material in the FITC, TRITC, and Cy5 fluorescent channels used in fluorescence microscopy, by relative measurement. In some embodiments, the metal layer has an autofluorescence that is less than about 80%, 70%, 60%, 50%, 40%, 30%, 20%, 10%, or 5% of the autofluorescence of parylene-C in the FITC, TRITC, and/or Cy5 fluorescent channels, by relative measurement. In some embodiments, the microfilter withstands a pressure of between about 10 mmHg and about 760 mmHg. In some embodiments, the tensile strength of the microfilter is greater than about 100 MPa. In some embodiments, the tensile strength of the metal layer is greater than about 100 MPa. In some embodiments, the diameter of the microfilter is between about 1 and about 30 millimeters. In some embodiments, the diameter of the microfilter is between about 2 and about 15 millimeters. In some embodiments, a first pore of the plurality of pores is separated from a second pore of the plurality of pores by a distance of about 1 to about 24 microns. In some embodiments, the microfilter comprises a central region comprising the plurality of pores and an annular support ring extending beyond the central region. In some embodiments, the width of the annular supporting ring is between about 0.5 and about 4 millimeters. In some embodiments, the width of the central region is between about 5 and about 20 millimeters. In some embodiments, the density of the plurality of pores per square millimeter is between about 1 and about 10,000 pores. In some embodiments, a surface of the metal layer is functionalized with a biomolecule. In some embodiments, the biomolecule is a nucleic acid or protein configured to bind to the target cell. In some embodiments, the biomolecule is a cytokine, antibody or receptor. In some embodiments, detecting the presence or absence of the probe bound to the target cell comprises measuring an electric signal. In some embodiments, the probe comprises a chemiluminescent substrate. In some embodiments, the probe comprises a fluorophore. In some embodiments, detecting the presence or absence of the probe bound to the target cell comprises detecting a fluorescent signal from the fluorophore. In some embodiments, a user detects the presence or absence of the fluorescent signal by fluorescent microscopy. In some embodiments, a computer comprising a software module configured to detect fluorescence detects the presence or absence of the fluorescent signal.

In some embodiments, detecting the presence or absence of the target cell in the method of diagnosing cancer comprises a computer-implemented method comprising: (a) transmitting, by a computer, a surface scanning instruction to a multichannel fluorescence acquisition device, wherein the microfilter is positioned on a stage of the multichannel fluorescence acquisition device; the surface scanning instruction comprising one or more commands for the multichannel fluorescence acquisition device to determine the z-axis height of the microfilter surface; (b) transmitting, by a computer, an image capture instruction to the multichannel fluorescence acquisition device, the image capture instruction comprising one or more commands for the multichannel fluorescence acquisition device to acquire a plurality of digital images of the microfilter using a channel corresponding to the fluorophore, wherein the plurality of digital images are acquired at each stage position in a z-stack having a focus plan centered on the microfilter surface height determined in step (a); (c) generating, by a computer, an in-focus image by stitching together in-focus portions of each of multiple images of the plurality of digital images; (d) selecting, by a computer, an in-focus image that comprises a cell of interest; and (e) identifying, by a computer, an area of interest comprising the cell of interest in the in-focus image. In some embodiments, the computer-implemented method further comprises determining, by a user, a probability of the cell of interest being the target cell. In some embodiments, the computer-implemented method further comprises determining, by a user, a probability of the cell of interest being from a particular type of cancer. In some embodiments, the cancer is ovarian cancer or breast cancer.

In some embodiments, the computer-implemented method further comprises enhancing, by a computer, the visibility of a feature in the acquired digital image.

In some embodiments, the method of diagnosing cancer comprises applying to the microfilter a second probe comprising a second fluorophore; wherein the computer implemented method further comprises transmitting a scanning instruction comprising one or more commands for the digital acquisition device to acquire a digital image of the microfilter using a second fluorescent channel corresponding to the second fluorophore. In some embodiments, the method of diagnosing cancer comprises applying to the microfilter a third probe comprising a third fluorophore; wherein the computer implemented method further comprises transmitting a scanning instruction comprising one or more commands for the digital acquisition device to acquire a digital image of the microfilter using a third fluorescent channel corresponding to the third fluorophore. In some embodiments, the method of diagnosing cancer comprises applying to the microfilter a fourth probe comprising a fourth fluorophore; wherein the computer implemented method further comprises transmitting a scanning instruction comprising one or more commands for the digital acquisition device to acquire a digital image of the microfilter using a fourth fluorescent channel corresponding to the fourth fluorophore. In some embodiments, the method of diagnosing cancer comprises applying to the microfilter a fifth probe comprising a fifth fluorophore; wherein the computer implemented method further comprises transmitting a scanning instruction comprising one or more commands for the digital acquisition device to acquire a digital image of the microfilter using a fifth fluorescent channel corresponding to the fifth fluorophore.

In some embodiments, detecting the presence or absence of the target cell in the method of diagnosing cancer comprises a computer-implemented method comprising: (a) transmitting, by a computer, an image capture instruction to a multichannel fluorescence acquisition device, wherein the microfilter is positioned on a stage of the multichannel fluorescence acquisition device; the image capture instruction comprising one or more commands for the multichannel acquisition device to acquire one or more digital images of the microfilter using a channel corresponding to a fluorophore of the probe; (b) receiving, by a computer, the one or more digital images of the microfilter; and (c) determining, by a computer, the presence or absence of the target cell in each of the one or more digital images of the microfilter. In some embodiments, the computer determines the presence or absence of the target cell using a software module configured with a trained convolutional neural network (CNN).

In some embodiments, the method of diagnosing cancer comprises applying to the microfilter a probe that binds to a nucleic acid. In some embodiments, the probe that binds to a nucleic acid is 2-(4-Amidinophenyl)-1H-indole-6-carboxamidine (DAPI).

In another aspect, provided herein is a computer-implemented method of processing an image of a microfilter for detecting cancer, the method comprising: (a) receiving, by a computer, a plurality of images of the microfilter, wherein the plurality of images of the microfilter are acquired using a multichannel fluorescence acquisition device; and (b) identifying, by the computer, the presence or absence of a target cell indicative of cancer in each of the plurality of images. In some embodiments, the identification comprises identifying one or more tumor derived myeloid cells. In some embodiments, the identification comprises identifying one or more circulating tumor cells. In some embodiments, the identification comprises distinguishing between tumor derived myeloid cells and circulating tumor cells. In some embodiments, the identification comprises generating a total count of one or more tumor derived myeloid cells. In some embodiments, the identification comprises generating a total count of one or more circulating tumor cells. In some embodiments, the identification comprises executions on one or more graphic processing unit. In some embodiments, the identification comprises a use of a neural networks method. In some embodiments, the identification comprises a use of a convolutional neural networks method. In some embodiments, the identification comprises a use of a supervised deep neural networks method. In some embodiments, the identification comprises image classification. In some embodiments, the identification comprises identifying one or more translation invariant features. In some embodiments, the identification comprises learning, extracting and enhancing one or more implicit feature of an input image. In some embodiments, the identification comprises a use of a neural network with one or more convolution layers. In some embodiments, the identification comprises a use of a neural network with one or more hidden convolution layers. In some embodiments, the identification comprises a use of a neural network with a plurality of convolution layers, the plurality of convolution layers processing data layer by layer. In some embodiments, the identification comprises a use of a neural network with at least one convolution layer, the at least one convolution layer comprising one or more feature filters. In some embodiments, the one or more feature filters are configured to (1) extract one or more features from a region of units using a convolution, (2) apply an additive bias, and (3) apply a sigmoid function. In some embodiments, the one or more features comprise one or more of the following: one or more local features, one or more global features, one or more edges, one or more colors, one or more intensity level, one or more spatial features, and one or more shape features. In some embodiments, the identification comprises a use of a neural network with one or more non-linear layers. In some embodiments, the one or more non-linear layers comprise a rectified linear transform. In some embodiments, the identification comprises a use of a neural network with one or more pooling layers. In some embodiments, the one or more pooling layers are configured to reduce a dimension of features. In some embodiments, at least two pooling layers execute sequentially. In some embodiments, the one or more pooling layers are configured to perform a max-pooling algorithm to pass only a maximum value. In some embodiments, the identification comprises a training step. In some embodiments, the identification comprises supervised learning. In some embodiments, the identification comprises using a labeled training database. In some embodiments, the identification comprises unsupervised learning. In some embodiments, the plurality of images comprises images acquired from at least two channels. In some embodiments, the plurality of images comprises images acquired from four channels.

In another aspect, provided herein is a computing system for processing images of a microfilter for detecting cancer, the system comprising: (a) a computing device comprising a processor, a memory module and an operating system, wherein the computing device is configured to (1) acquire a plurality of images of a microfilter, (2) identify a first image with a target cell indicative of cancer, (3) identify a second image with a target cell not indicative of cancer, and (3) transmitted the first and the second images to a server; and (b) the server comprising a server processor, a memory module, a server operating system and at least one graphics processing unit, wherein the server is configured to (1) receive the first and the second images, and (2) perform a classification analysis on the first and the second images using a convolutional neural network model based on the at least one graphics processing unit. In some embodiments, the computing device is further configured to generate an identification report and transmit the identification report to the server. In some embodiments, the server is further configured to perform the classification analysis based on the identification report. In some embodiments, the computing device is further configured to aggregate first patient information and transmit the first patient information to the server. In some embodiments, the computing device is further configured to aggregate second patient information and transmit the second patient information to the server. In some embodiments, the server is configured to compare the first and the second patient information. In some embodiments, the server is configured to refine the convolutional neural network model when the server determines that the first and the second patient information are different. In some embodiments, the determination is evaluated by a probabilistic method. In some embodiments, the refined convolutional neural network model replaces the convolutional neural network model for a future use. In some embodiments, the at least one graphics processing unit comprises two or more processing cores.

BRIEF DESCRIPTION OF THE DRAWINGS

This application file contains at least one drawing executed in color. Copies of this patent application publication with color drawings will be provided by Applicant upon request and payment of the necessary fee.

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE INVENTION

Figure 1A:
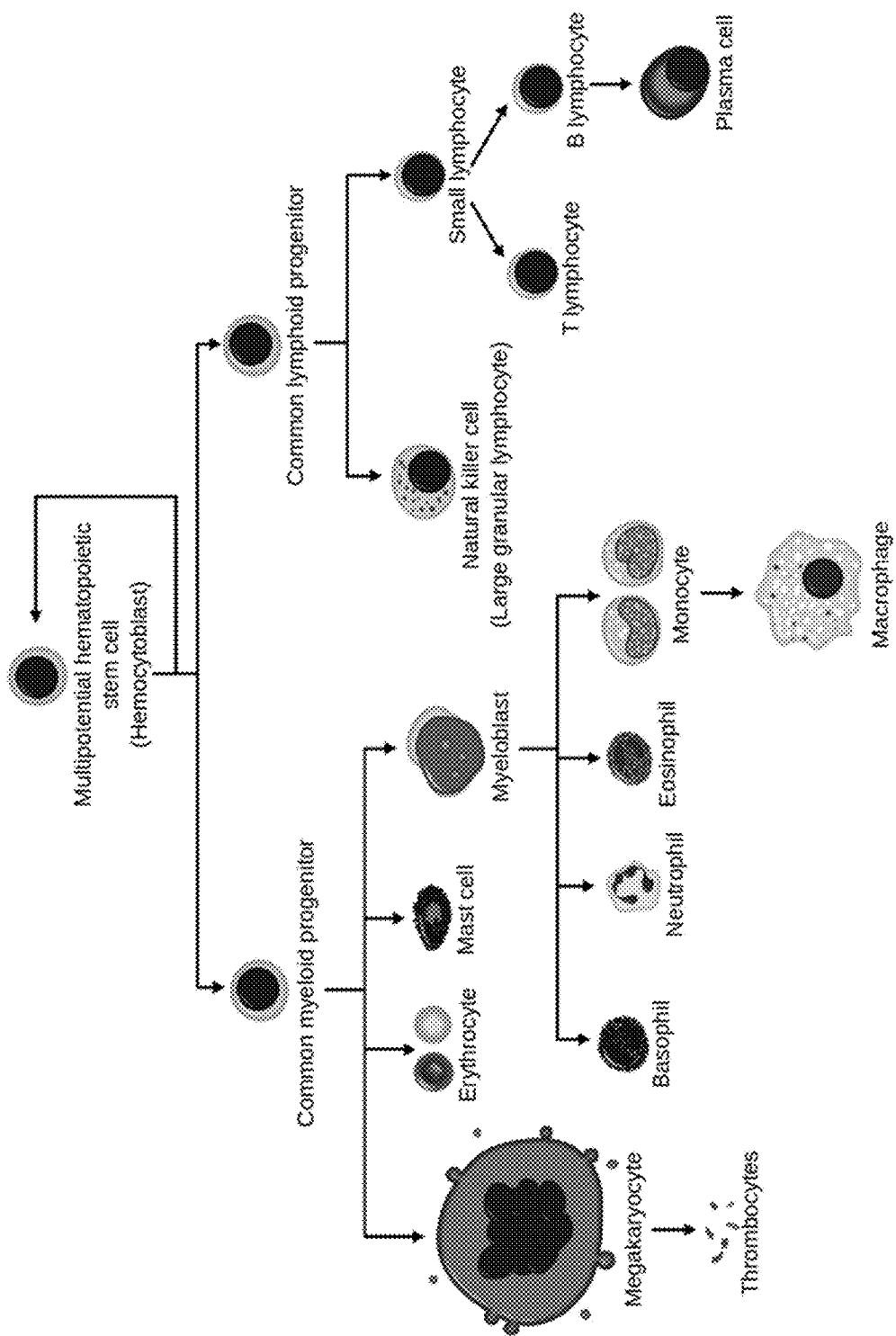
FIG. 1A is an illustration of the development tree of macrophages and other myeloid cells from multipotential hematopoietic stem cells.

Provided herein are systems and methods for the detection of a target cell in a biological sample from a subject. Target cells include those which correlate to a disease or condition and thus the methods provide for diagnosing and monitoring a disease or condition in the subject. For example, the detection of tumor derived cells such as TDMCs, CTCs and TAMs in a sample from a subject is indicative of cancer in that subject. Detection methods include identifying a cell of interest as being a target cell by comparing one or more features or biomarkers of the cell of interest with that of the target cell which are specific to a certain disease or condition. In some cases, characterization of an identified target cell is indicative of a state of a disease or condition and as such, allows for the monitoring of the disease or condition over time in a subject. As non-limiting examples, characterization of tumor derived cells are useful for determining if a tumor is malignant or benign; evaluating patient response to therapy such as surgery, chemotherapy, immunotherapy or hormonal therapy; determining if a cancer patient has a recurrence; determining if a cancer patient is in remission; and validating or confirming a cancer diagnosis made by other means.

Detection of a target cell is often facilitated by enriching the biological sample for the target cell. In the case of tumor derived cells or other appropriate cells which are larger than other cells types in the sample, a method for enrichment is size inclusion or exclusion. Further provided herein are methods for enriching a biological sample for a target cell by size inclusion using microfiltration. An exemplary microfiltration method comprises passing a biological sample through a microfilter comprising a plurality of pores. Cells and molecules smaller than the diameter of the pores are removed, and potential target cells having diameters larger than the diameter of the pores are enriched on the microfilter. In some microfiltration methods, a potential target cell is captured on a microfilter by binding of the cell to a capture element on a surface of the microfilter. A capture element is inclusive of a biomolecule with a binding affinity for a target cell as well as a structure that physically retains a potential target cell within the structure on the microfilter. Target cells captured and identified using a microfilter may be further analyzed by molecular diagnostics, where a molecular signature such as a genetic sequence is identified in the target cell to identify or characterize a disease or condition. Target cells can also be analyzed by numerous single-cell analytical techniques, including sequencing, that enable identification and analysis of proteins, nucleic acids, morphology, and other biological molecules and structures.

In one aspect of the systems and methods described herein, a size based inclusion method is provided for isolating potential target cells using a micropore filter, or "microfilter" comprising a layer of metal. The layer of metal provides a strength to the microfilter so that the microfilter can be bound to a carrier for filtration and/or detection of captured cells and is amenable to automated handling. For methods that comprise the detection of a target cell using fluorescence microscopy, the metal material has a low autofluorescence and thus an increased signal to noise ratio. In some embodiments, the microfilter is fabricated using photolithographic technology, whereby the metal is electroplated on a mechanical support comprising one or more posts correlating to one or more pores in the finished microfilter. The metal is then removed from the substrate comprising the one or more pores. In some methods, a target cell to be isolated is a tumor derived cell such as a TDMC, CTC, TAM or a related cell. If present, target cells having diameters larger than the pores of the microfilter are retained on the surface. For example, TDMCs are typically 12 to 22 microns in diameter and are filtered using microfilters having pores with diameters between about 1 and 50 microns separated by approximately 2-24 microns. Once potential target cells are captured by the microfilter, captured cells are removed from the microfilter or retained, for example, by fixation, for analysis.

In another aspect, provided herein are methods for detecting and/or characterizing a target cell by analyzing a feature and/or biomarker of a cell of interest from a biological sample and comparing the feature and/or biomarker to a signature of the target cell. A feature of a cell includes morphology of the cell, morphology of the nucleus, size of the cell, size of the nucleus, and the presence of multiple nuclei. Biomarkers of a cell include the presence and/or absence of one or more biomarkers within, expressed on, or bound to the cell, such as proteins, nucleic acids, carbohydrates, lipids, and small molecules. As a non-limiting example, some tumor derived cells comprise one or more biomolecules obtained from the tumor environment and as such, detection of these biomolecule biomarkers is indicative of the presence of that tumor. In some embodiments, a target cell is detected by analyzing the nucleus of a cell of interest, where the cell of interest comprises a large, irregular nucleus and/or multiple nuclei. In some embodiments, a target cell is a cell of interest that is CD45+ and/or comprises cytokeratin 8 (Ck8), cytokeratin 18 (Ck18), cytokeratin 19 (Ck19), and/or EpCAM. For potential target cells isolated on a microfilter, a method of detecting the one or more features and/or biomarkers of a target cell comprises applying to the microfilter one or more probes specific for the one or more features and/or biomarkers. In some methods, one or more probes specific for the one or more features and/or biomarkers are combined with a sample prior to microfiltration. In some cases, the probes comprise a fluorophore, which allow for target cells to be identified using fluorescent microscopy. The microfilter is then visualized by a clinician and/or automated system to identify the presence and/or absence of the features and/or biomarkers.

Further provided herein are methods for detecting and characterizing a target cell using a computerized image recognition system. In some such instances, a biological sample suspected of comprising a target cell is imaged and an artificial neural network system utilizing convolutional neural networks, pooling, and deep learning automatically identifies and counts, if present, the target cell. In various examples, the target cell is imaged after capture on a microfilter. In some cases, the system distinguishes between different cell types. As an example, a TDMC is differentiated from a CTC. In some cases, the system distinguishes between different types of target cells derived from different diseases. For suspected target cells identified by the system, a clinician can be notified for further analysis of the image. To facilitate analysis of the image by both a computer system and clinician, the biological sample suspected of comprising a target cell may be treated with one or more probes specific for the target cell. As a non-limiting example, a biological sample is treated with a fluorescent probe and imaged using fluorescent microscopy.

Target Cells

In various aspects, provided herein are systems and methods for identifying and optionally characterizing a cell of interest as a target cell by analyzing a signature of the cell of interest and comparing it to a signature of the target cell. A signature of a cell includes a feature of the cell as well as the presence, absence or relative amount of one or more biomarkers within and/or associated with the cell. Biomarkers cover a broad range of biochemical entities, such as nucleic acids, proteins, lipids, carbohydrates, small metabolites, and cytogenetic and cytokinetic parameters. The signature of a cell of interest is useful for diagnosing or otherwise characterizing a disease or condition in a patient from which the potential target cell was isolated. As used herein, an isolated cell refers to a cell separated from other material in a biological sample using any separation method including, without limitation, microfiltration. An isolated cell may be present in an enriched fraction from the biological sample and thus its use is not meant to be limited to a purified cell. In some embodiments, the morphology of an isolated cell is analyzed. In some embodiments, analyzing comprises determining the presence or absence of a biomarker in the cell. In some embodiments, analyzing comprises determining a level of a biomarker within or associated with the cell. For target cells indicative of cancer, analysis of a cell signature is useful for a number of methods including diagnosing cancer, determining a stage of cancer, determining a type of cancer, and monitoring progression of cancer with a given treatment. Some of these methods involve monitoring a change in the signature of the target cell, which includes an increase and/or decrease of a biomarker and/or any change in morphology.

In some embodiments, the signature of a cell of interest is analyzed in a fraction from a biological sample of a subject, wherein the biological sample has been processed to enrich for a target cell. In some cases, the enriched fraction lacks the target cell and the absence of a signature of a target cell in the enriched fraction indicates this absence. Target cells include tumor derived cells such as TDMCs, CTCs, TAMs and other large and/or myeloid derived cells.

Myeloid Derived Cells

Figure 1B:
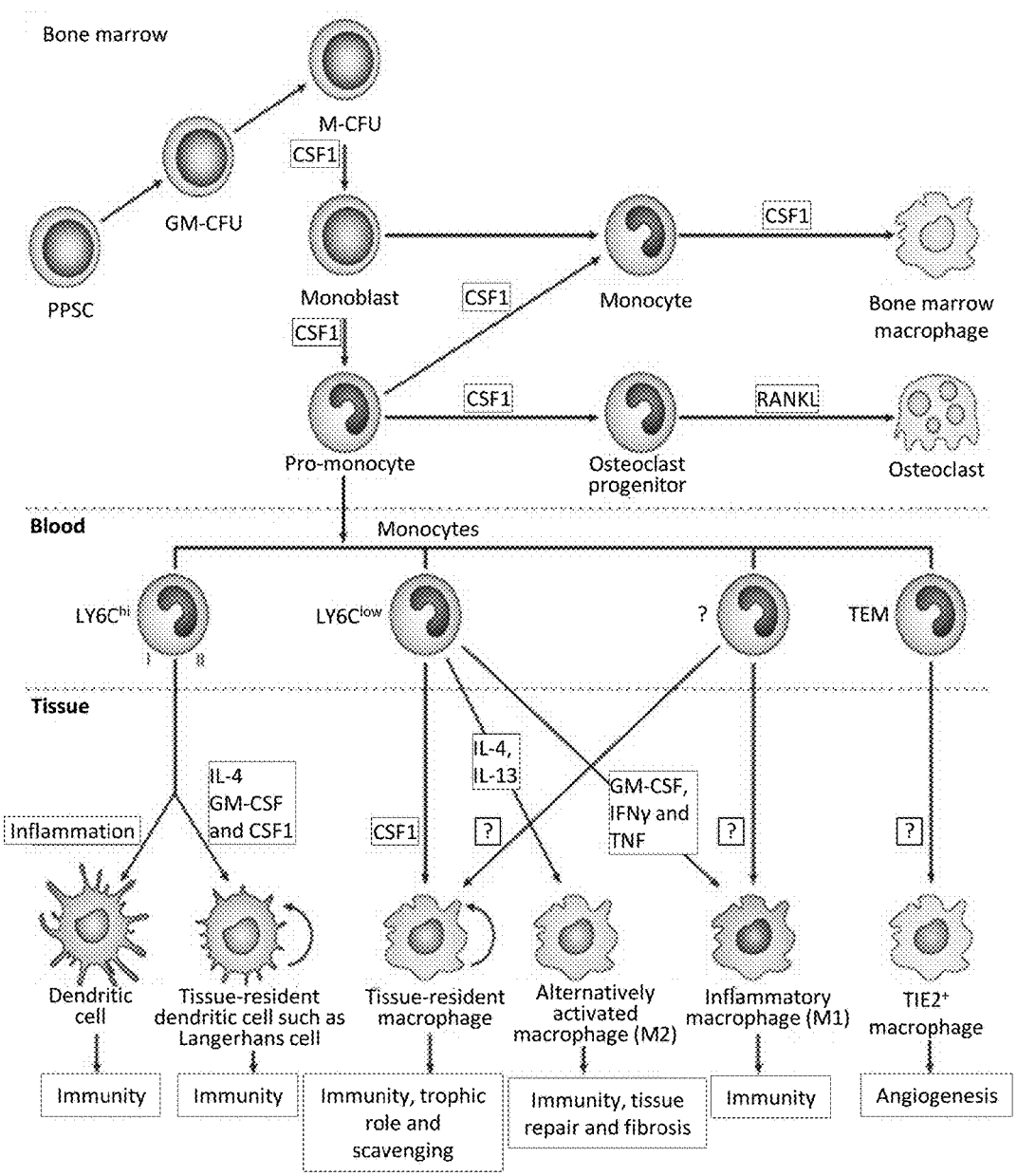
FIG. 1B is a diagram showing the differentiation of monocytes into various types of macrophages and other myeloid cells.

The developmental tree of myeloid and lymphoid cells derived from multipotential hematopoietic stem cells (hemocytoblasts) is shown in FIG. 1A. As shown, myeloid derived cells include monocytes and macrophages. FIG. 1B shows how circulating monocytes give rise to a variety of tissue resident macrophages throughout the body. Macrophages are important cells of the immune system that are formed in response to an infection or accumulating damaged or dead cells where they recognize, engulf and destroy select cells. When there is tissue damage, infection, or a tumor, monocytes leave the blood stream and enter the affected tissue or organ and undergo a series of changes to become macrophages. These macrophages can modify themselves to form different structures in order to fight various different microbes and invaders. In this way, macrophages provide a first line of defense in protecting the host from infection and cancer. The macrophages present in humans are around 21 microns in diameter and comprise one or more specific protein markers on their surfaces. Some non-limiting examples include CD14, CD11b, EMR1, MAC-1/MAC-3, Lysozyme M and CD68.

Figure 2:
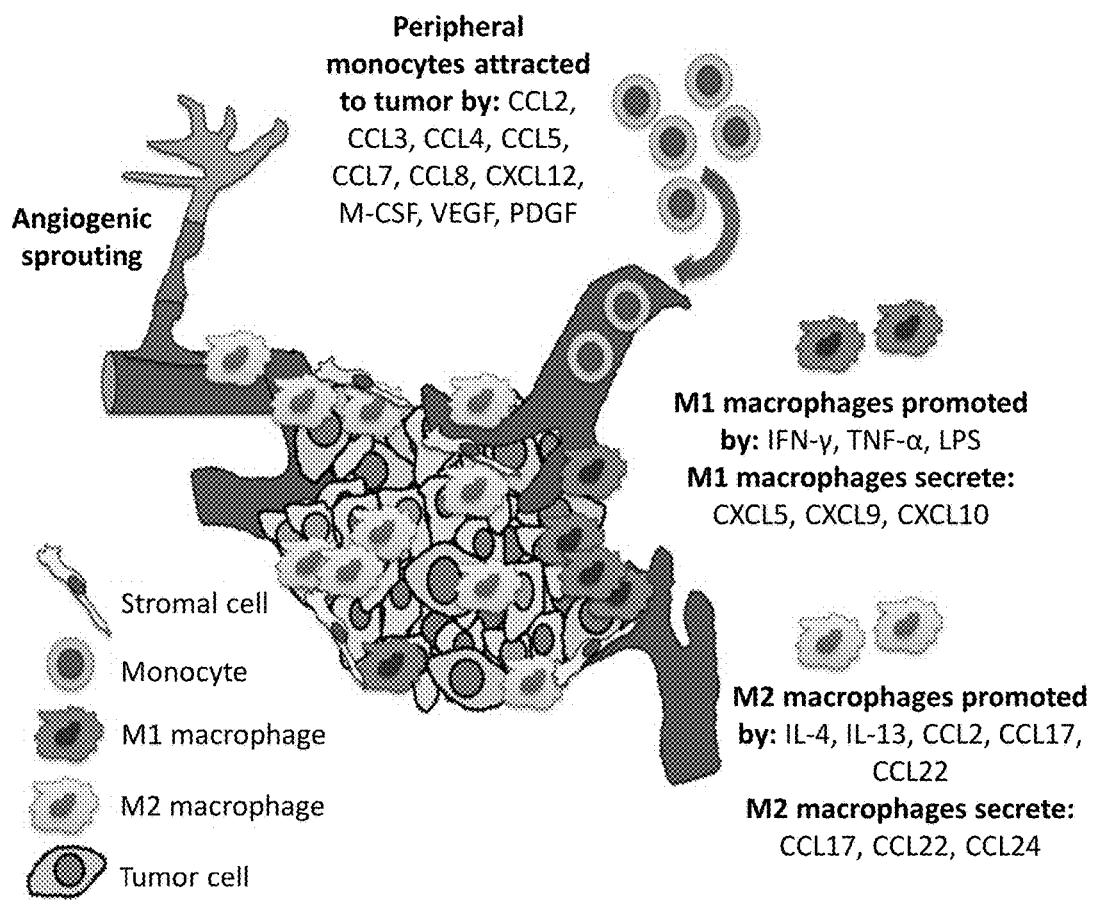
FIG. 2 is an illustration of a cancer tumor and associated features.

Monocytes originate in bone marrow from a common myeloid progenitor that is shared with neutrophils, and then are released into the peripheral blood, where they circulate for several days before entering tissues and replenishing the tissue macrophage populations. The morphology of mature monocytes in the peripheral circulation is heterogeneous, and these cells constitute ~5-10% of peripheral-blood leukocytes in humans. They vary in size and have different degrees of granularity and varied nuclear morphology. As shown in FIG. 2, monocytes are attracted by tumors by the tumor emission of chemoattractants such as CCL2, CCL3, CCL4, CCL5, CCL7, CCL8, CXCL-12, M-CSF, VDGF, PDGF, and others. The monocytes enter the tumor from the blood stream where they are promoted into M1 macrophages by IFN-[gamma], TNF-[alpha], and LPS. M1 macrophages secrete CXCL5, CXCL9, and CXCL10. Monocytes are also promoted into M2 macrophages by IL-4, IL-13, CCL2, CCL17, and CCL22. M2 macrophages secrete CCL17, CCL22, and CCL24.

Myeloid Derived Cells and Cancer

Macrophages readily enter and exit the stroma of the tumor through vasculature. Macrophages that have been in contact with the tumor and have moved back into blood stream are Tumor Derived Myeloid Cells (TDMCs) as discussed elsewhere herein. TDMCs have been identified in the blood of cancer patients, even those patients with early stage cancer, but have not been found in normal patients.

The tumor microenvironment is a highly varied ecology of cells that evolves with and provides support to tumor cells during the tumor progression. Among the innate and adaptive immune cells recruited to the tumor site, macrophages are abundant and are present at all stages of tumor development, where they can play a protumoral role. For example, in the primary tumor, macrophages can stimulate angiogenesis and enhance tumor cell invasion, motility, and intravasation. During tumor development and/or metastasis, macrophages prepare the premetastatic site and promote tumor cell extravasation, survival, and growth. Generally, tumor associated macrophages (TAMs) have been found to promote tumor progression via different mechanisms.

Tumor Derived Cells

Tumor derived cells targeted for detection using devices and methods herein include those of myeloid origin such as TDMCs, CTCs and TAMs. These tumor derived cells are identified by analyzing one or more features and/or biomarkers of potential target cells in a biological sample of a subject. In some embodiments, the biological sample has been enriched for tumor derived cells. In some cases, enrichment includes exclusion of other types of cells and components such as erythrocytes, platelets and lymphoid and myeloid cells. For example, TDMCs are present in peripheral blood when a tumor is present along with other types of lymphoid and myeloid cells to make up the Complete Blood Count (CBC). As such, to avoid false positives from other cell types an exclusion protocol is optionally performed prior to analysis.

In some embodiments, one or more biomarkers of a tumor derived cell distinguish the cell from another tumor derived cell or from a non-tumor derived cell. For example, when monocytes encounter foreign material in the bloodstream they can progress to macrophages without entering the tissue. These macrophages can be distinguished from macrophages or myeloid cells that are found in tumors by differences in and/or the presence or absence of one or more biomarkers in either type of cell.

In some embodiments, a tumor derived cell has one or more biomarkers specific for the type of tumor from which it was derived. In some cases this specificity is the presence or absence of a biomarker. In some cases this specificity is a degree of the presence of a biomarker or the binding or take up of a probe specific for the biomarker. As a non-limiting example, in some embodiments, ovarian TDMCs have a lower degree of binding to anti-EpCAM than TDMCs originating from breast cancer tumors. As another example, TDMCs derived from prostate cancers may have engulfed prostate material and thus have taken up or bound to PSMA.

Characteristics of a tumor derived cell that make up the signature of the cell include, without limitation: (a) large atypical nucleus or multiple nuclei; (b) expression of one or more of cytokeratin 8, 18 and 19; (c) cell size greater than about 10-20 microns; (d) CD45 positive phenotype (TDMCs) or CD45 negative phenotype (CTCs); (e) expression of EpCAM; (f) expression of one or more markers of a primary tumor; and any combination of (a)-(1). Further described are signature characteristics of a tumor derived cell that are indicative of the type of tumor from which the cell was derived, including, without limitation, prostate specific membrane antigen (PSMA), alpha-fetoprotein (AFP), carcinoembryonic antigen (CEA), cancer antigen (CA-125), MUC-1, ETA, tyrosinase, melanoma-associated antigen (MAGE), vascular endothelial growth factor (VEGF), human epidermal growth factor receptor 2 (Her2nue), Beta 2 microglobulin (B2M), c-kit/CD117, estrogen receptor (ER), progesterone receptor (PR), fibrin and fibrinogen. Microfilter devices, systems and diagnostic methods described herein are applicable to any tumor marker known in the art and are not limited to those exemplified herein. In some embodiments, a characteristic of a tumor derived cell includes an absence of binding to a negative biomarker. For example, a tumor derived cell is identified as not being derived from a specific type of tumor if the tumor derived cell does not bind to a biomarker of the specific type of tumor. As such, any of the markers provided herein and known in the art which are specific for one or more types of cancers are useful as negative biomarkers for diagnosing a type of tumor derived cell in any method described herein.

Target Cell Enrichment

The identification and/or characterization of a target cell by analyzing a signature of a potential target cell is facilitated by enriching a biological sample for the target cell. The biological sample is obtained from a subject by any means including non-invasive or minimally invasive techniques such as a blood draw. A biological sample or sample refers to any preparation containing cellular material from a subject including, without limitation, blood, serum, plasma, tissue, sweat, tear, urine, skin and hair. Methods for enriching a biological sample for a target cell include any method which increases the concentration of the target cell, if present, from the concentration of the target cell in the subject. Biological samples described herein include samples of cellular material from a subject before, during and after any enrichment or purification procedure.

In some embodiments, if a target cell is present in a biological sample, the target cell is isolated or captured using a microfilter comprising a plurality of pores. In some such cases, the target cell is retained on a surface of the microfilter while other cells in the sample are removed by passage through the plurality of pores. For example, tumor derived cells of monocyte origin are larger than other cell types and thus could be retained on a microfilter having pore diameters smaller than the diameter of monocytes. One method for enrichment of blood samples comprises passing the blood through a microfilter, whereby cells smaller than the target cell are removed through pores of the microfilter. The types and sizes of various blood cells are: erythrocytes (7-8 μm), neutrophils (12-14 μm), eosinophils (12-17 μm), basophils (14-16 μm), lymphocytes (6-9 μm), and monocytes (up to 20 μm). By exploiting this size difference, target cells in the blood which are larger than other cell types are retained on the microfilter. As a non-limiting example, a microfilter comprising pore sizes between about 1 and about 50 microns is used to filter a blood sample for enrichment of large cells such as monocytes and tumor derived cells.

Although use of a microfilter to enrich for target cells is exemplified in some embodiments herein, other methods may be used alone or in combination with microfiltration for target cell enrichment. Other methods include, centrifugation, flow cytometry, cell marker adhesion methods, affinity purification, blood smearing and spreading on slides, and use of other micro fabricated devices.

Microfilters

In one aspect of the disclosure, provided herein are microfilters for the enrichment of a target cell from a biological sample. The biological sample may comprise the target cell, not comprise the target cell and/or be suspected of comprising the target cell. In some embodiments, the microfilter comprises a plurality of pores sufficient in size to allow erythrocytes, serum and platelets in a blood sample to pass while retaining larger leukocytes and tumor derived cells.

In some embodiments, a microfilter comprises a biologically compatible metal layer and a plurality of pores extending through the metal layer. In various cases, a biologically compatible metal layer has a minimal or no adverse effect on biological material from a biological sample as the biological material is passed through and/or retained on the microfilter during filtration. For example, the biological material comprises a target cell and the target cell is not lysed or morphologically altered by the biologically compatible metal layer. Non-limiting examples of metals in a microfilter include titanium, nickel, gold, silver, cobalt, chromium, copper, iron, manganese, platinum, zinc, palladium, molybdenum, tungsten, aluminum, indium, carbon, silicon, tin, lead and alloys and combinations thereof. In some, cases the microfilter comprises nickel or an alloy thereof. In some cases, the microfilter comprises palladium or an alloy thereof. An exemplary microfilter comprises nickel and palladium.

In some embodiments, a microfilter comprises a material that has low fluorescence for fluorescent microscopy imaging. The low autofluorescence is a function at least of the composition of the microfilter. In some cases, the microfilter comprises a metal with low autofluorescence. As a non-limiting example, the microfilter comprises nickel, palladium or both nickel and palladium. In some embodiments, the metal layer has low autofluorescence, where low autofluorescence is an autofluorescence less than parylene-C filter material in the FITC, TRITC, and/or Cy5 fluorescent channels used in fluorescence microscopy, by relative measurement. In some embodiments, the metal layer has an autofluorescence that is less than about 80%, 70%, 60%, 50%, 40%, 30%, 20%, 10%, or 5% of the autofluorescence of parylene-C in the FITC fluorescent channels, by relative measurement. In some embodiments, the metal layer has an autofluorescence that is less than about 80%, 70%, 60%, 50%, 40%, 30%, 20%, 10%, or 5% of the autofluorescence of parylene-C in the TRITC fluorescent channels, by relative measurement. In some embodiments, the metal layer has an autofluorescence that is less than about 80%, 70%, 60%, 50%, 40%, 30%, 20%, 10%, or 5% of the autofluorescence of parylene-C in the Cy5 fluorescent channels, by relative measurement. In some cases, comparative measurements are performed under similar measurement conditions, for instance, the same excitation source, microscope slide type (e.g., glass) and/or detector are used to measure fluorescence from the metal layer as the parylene-C. In some cases, low autofluorescence is less than about 20% of the autofluorescence of parylene-C in the FITC channel. In some cases, low autofluorescence is less than about 20% of the autofluorescence of parylene-C in the TRITC channel. In some cases, low autofluorescence is less than about 50% of the autofluorescence of parylene-C in the Cy5 channel. In some cases, the metal layer has low autofluorescence from excitation wavelengths of about 330 nm to about 650 nm, when auto fluorescing in emission wavelengths of about 400 nm to about 800 nm.

In some embodiments, a microfilter has a strength sufficient to allow for ease of handling and is amenable to automatic handling. In some embodiments, the microfilter withstands a pressure of at least about 10, 50, 100, 200, 250, 300, 350, 400, 450, 500, 550, 600, 650, 700, or 750 mmHg. In some embodiments, the microfilter withstands a pressure of at least 10-760 mmHg, 100-760 mmHg, 200-760 mmHg, 300-760 mmHg, 400-760 mmHg, or 500-760 mmHg. In some embodiments, the microfilter has a tensile strength greater than 75, 100, 150, 200, 250, 300, 350, 400, 450, 500, 550, or 600 MPa. The strength of the microfilter is a function of at least one or more of: the composition of the microfilter, the height of the microfilter and the size and density of pores within the microfilter. In some cases, the microfilter comprises a metal layer with a strength greater than 75, 100, 150, 200, 250, 300, 350, 400, 450, 500, 550, or 600 MPa. As a non-limiting example, the microfilter comprises nickel, palladium or both nickel and palladium. In some embodiments, the height of the microfilter is between about 5 and about 1,000 microns. Non-limiting microfilter heights include about 5, 6, 7, 8, 9, 10, 11, 12, 13, 14, 15, 16, 17, 18, 19, 20, 50, 100, 200, 300, 400, 500, 600, 700, 800, 900 and 1,000 microns, as well as any range therein, such as 5-15, and 50-500 microns. In some embodiments, the diameter of length along an axis of the microfilter is between about 1 and about 30 millimeters. Non-limiting examples of microfilter diameters and lengths include about 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 millimeters, as well as any range therein, such as 1-20, 6-18, 7-16, 8-15, and 9-14. In some embodiments, the filter surface area of the microfilter is between about 20 mm² and 1,000 mm², between about 20 mm² and 300 mm², or between about 40 mm² and 80 mm².

Figure 3:
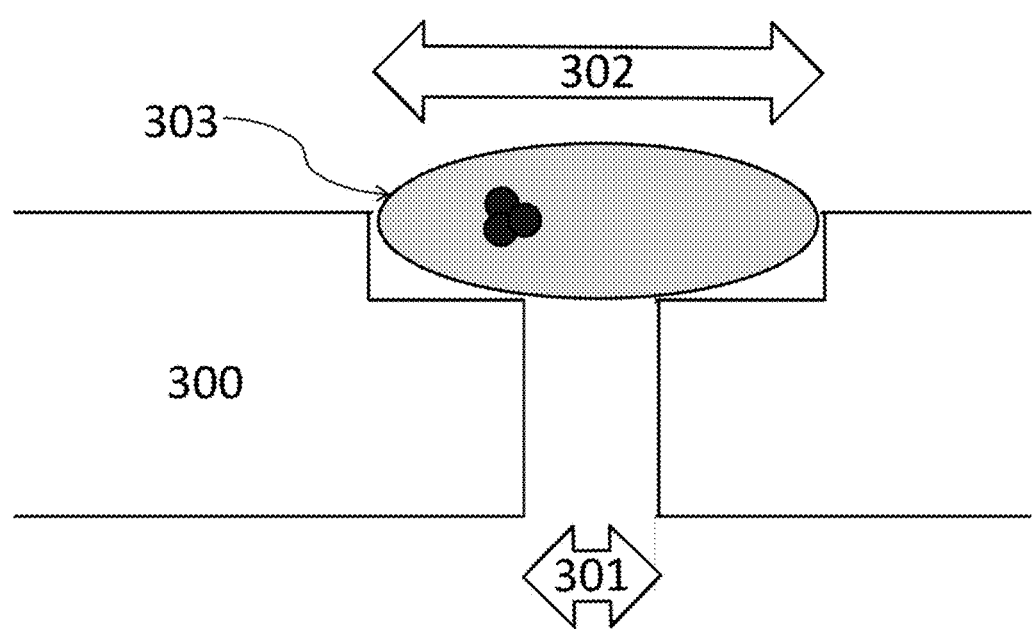
FIG. 3 is a side view of microfilter comprising a stepped pore.

The plurality of pores in a microfilter are configured in any pattern and include pores which are heterogeneous and homogeneous in the plurality. One or more the pores take the form of any shape, including a circle, square, ellipse, oval, triangle, and patterns such as a zig-zag. Pores do not need to be uniform in size throughout the microfilter and pores having a variety of dimensions as the pores progress through the microfilter are envisioned. Further provided are microfilters comprising one or more structural features such as microwells and/or posts for capturing and retaining target cells. In some embodiments, a pore of a microfilter comprises a microwell. In some embodiments, the pore is a stepped pore comprising a first diameter and a second diameter, wherein the second diameter defines a microwell, and the first diameter is smaller than the second diameter and defines a channel through which cells may pass. A non-limiting example of a stepped pore is shown in FIG. 3. Microwell 300 comprises a pore having a second diameter 301 and a first diameter 302, where a target cell of interest 303 is captured on the microwell formed by the larger second diameter of the pore. In some embodiments, the second diameter, or channel diameter, is from about 1 micron to about 12 microns, or about 1, 2, 3, 4, 5, 6, 7, 8, 9, 10, 11 or 12 microns. In some embodiments, the first diameter, or microwell diameter, is from about 6-100 microns, 6-80 microns, 6-60 microns, 6-40 microns, 10-100 microns, 10-80 microns, 10-60 microns, or any range therebetween. In some cases, the diameter of the microwell of a pore is about 10, 20, 30, 40, 50, 60, 70, 80, 90 or 100 microns. In the non-limiting example of FIG. 3, diameter 301 is about 20 microns and diameter 302 is about 5-6 microns.

In some embodiments, one or more of the plurality of pores has a diameter of between about 1 and about 50 microns. As used herein, diameter is not limited to a pore having a circular shape and is inclusive of the length and/or width along any axis of a pore. For example, for pores having different diameters throughout their X or Y axis, such as the case with a stepped pore, the diameter refers to any diameter along the X or Y axis, respectively. Non-limiting diameters of a pore include about 4, 5, 6, 7, 8, 9, 10, 11, 12, 13, 14, 15, 20, 25, 30, 35, 40, 45, and 50 microns, as well as any range therein, such as 4-12, 5-10, 6-9, 7-8, 5-20, 10-30, and 25-50 microns. In some embodiments, the aspect-ratio of each of the plurality of pores is less than about 5, 4, 3, 2 or 1. In other embodiments, the aspect-ratio of each of the plurality of pores is greater than about 5, such as greater than about 10, 15, 20 or more. In some embodiments, a first pore of the plurality of pores is separated from a second pore of the plurality of pores by a distance of about 2 to about 24 microns. In some cases, two pores within the plurality of pores are separated by about 2, 3, 4, 5, 6, 7, 8, 9, 10, 11, 12, 13, 14, 15, 16, 17, 18, 19, 20, 21, 22, 23, or 24 microns. In some embodiments, the density of the plurality of pores per square millimeter of microfilter is between about 1 and about 10,000 pores, between about 5 and about 5,000 pores, between about 5 and about 3,000 pores, less than 1 pore, or greater than 3,000 pores.

In some embodiments, a microfilter is patterned so that a central region of the microfilter comprises a plurality of pores (referred to as a membrane) and surrounding this central region may be an annular support ring optionally not comprising a pore. In some cases the annular support ring comprises one or more pores. The annular support ring is not limited in shape to a ring and includes any shape suitable for surround one or more sides or the entire central region. In some such cases, the width of the annular supporting ring is between about 0.5 and about 20 millimeters. For example, the annular supporting ring is about 1, 2, 3, 4, 5, 10, 15 or 20 millimeters in width. In some cases, the diameter or length along an axis of the central region is between about 5 and about 30 millimeters. For example, the diameter or length of the central region is about 5, 6, 7, 8, 9, 15, 20, 25 or 30 millimeters.

In some embodiments, a microfilter comprises a surface that is functionalized with a biomolecule or chemical moiety for attracting or otherwise interacting with a target cell. In some cases the microfilter comprises a functionalized metal layer. An example of a biomolecule is a cytokine. Another example of a biomolecule is an antibody. For microfilters configured to enrich for tumor derived cells, biomolecules also include EpCAM, Ck8, Ck18, Ck19, as well as biomolecules which bind with a target specific for the tumor from which the cells were derived.

Microfilters are optionally bonded to or otherwise situated in a microfilter holder during and/or after microfiltration. In some embodiments, a microfilter is bonded to a microfilter holder using an adhesive. In some embodiments, a microfilter is held by or onto a microfilter holder using pressure and/or friction. In some embodiments, a microfilter holder is or is part of a cassette. A cassette is sometimes used to hold a microfilter during a microfiltration process. In some cases, a microfilter is held between a slide cover and a slide, where the slide is the microfilter holder. In some configurations, a microfilter holder comprises an opening flanked by a rim, where a periphery of the microfilter is bonded to the rim of the microfilter holder. In some cases, the periphery of the microfilter does not comprise the plurality of pores and the plurality of pores is exposed to the opening of the microfilter holder. The microfilter holder may be of any material suitable for holding a microfilter, including, for example, glass and plastic. In some cases the microfilter holder is a slide used for microscopy or digital imaging of the microfilter.

Figure 4:
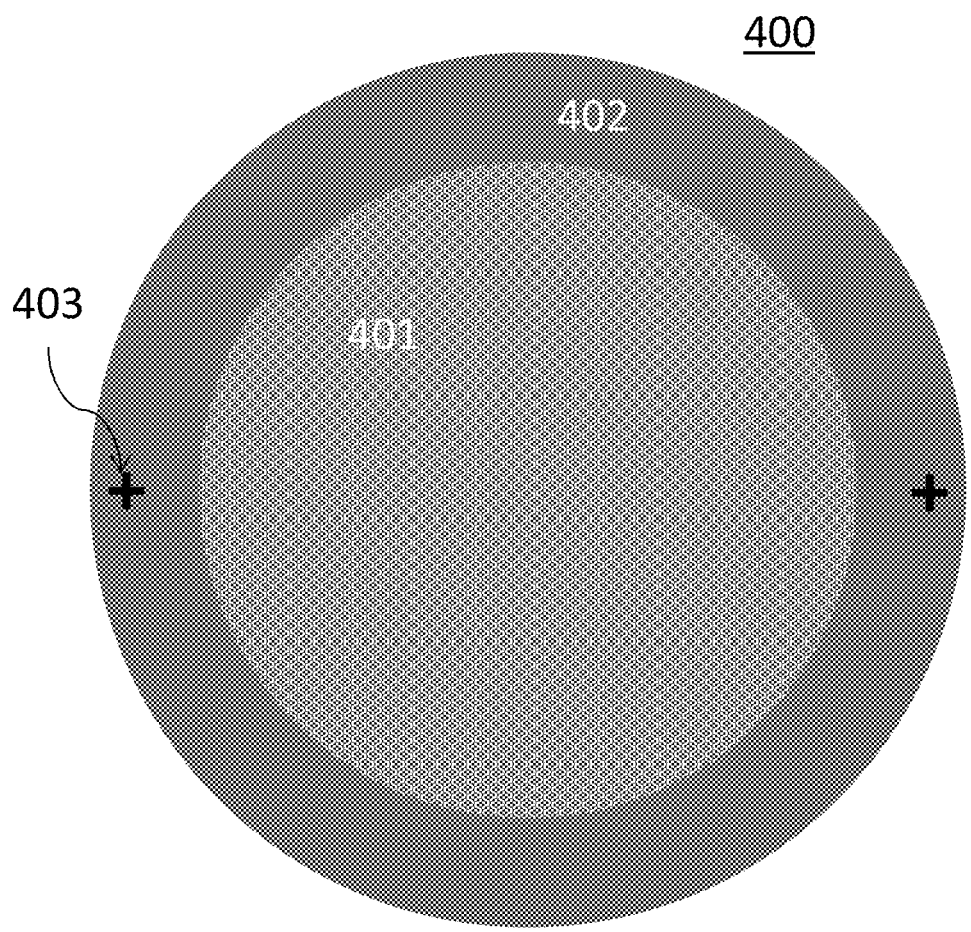
FIG. 4 is an illustration of a single microfilter membrane with registration marks.

A non-limiting example of a microfilter is shown in FIG. 4. Microfilter 400 comprises a circular disk comprising a central region 401 comprising a plurality of pores (membrane) and an annular supporting ring 402. Two registration marks 403 denoted by a (+) are shown on the annular ring. Such registration marks are included for ease of alignment during microscopy. In this example, the membrane of the microfilter 401 is about 8 microns thick and 9 mm in diameter. The annular supporting ring 402 is 2 mm in width. The dimensions, shapes and materials of a microfilter may vary from those exemplified as long as the filter membrane is thick enough for structural rigidity and the overall surface area is sufficient to allow low-pressure filtration to occur in a short period. The filter area corresponding to the membrane 401 in one embodiment is comprised of series of parallel lines of 8 micron diameter holes on 16 micron centers. The strips are separated in one embodiment by 16 microns and are alternatingly staggered by 8 microns so that the filter holes form a hexagonal pattern. The dimensions provided are exemplary and strip separation and pore spacing may vary as long as there is sufficient filter membrane material to preserve structural rigidity and to provide a surface on which to collect target cells.

Microfilter Fabrication

Microfilters described herein are prepared using any number of methods and the exemplary methods described herein are not limiting. In some embodiments, a microfilter is prepared by a method comprising electroplating a layer of material onto a mechanical support. In some embodiments, the mechanical support comprises a plurality of pillars having diameters of desired pore size in the prepared microfilter. As a non-limiting example, the layer of material is electroplated on the mechanical support around the pillars, the plurality of pillars having diameters between about 1 and about 100 microns. In some embodiments, the layer of metal is electroplated at height about equal to or less than the height of the pillars. As a non-limiting example, the layer of material is between about 1 and about 50 microns thick. In some embodiments, the microfilter is prepared to have a diameter or length in one axis of between about 1 and 30 millimeters, or about 2, 5, 8, 9, 10, 11, 12, 13, 14, 15, 20, 25 or 30 millimeters.

In some embodiments, the layer of material electroplated on the mechanical support has an autofluorescence less than parylene-C filter material in the FITC, TRITC, and Cy5 fluorescent channels used in fluorescence microscopy, by relative measurement. In some embodiments, the layer has an autofluorescence that is less than about 80%, 70%, 60%, 50%, 40%, 30%, 20%, 10%, or 5% of the autofluorescence of parylene-C in the FITC, TRITC, and/or Cy5 fluorescent channels, by relative measurement. In some cases, the layer of material has an autofluorescence less than about 20% of the autofluorescence of parylene-C in the FITC channel. In some cases, the layer of material has an autofluorescence less than about 20% of the autofluorescence of parylene-C in the TRITC channel. In some cases, the layer of material has an autofluorescence less than about 50% of the autofluorescence of parylene-C in the Cy5 channel. In some cases, the layer has low autofluorescence from excitation wavelengths of about 330 nm to about 650 nm, when auto fluorescing in emission wavelengths of about 400 nm to about 800 nm. In some embodiments, the layer of material comprises a material of suitable strength and thickness so that the resulting microfilter withstands a pressure of at least about 75, 100, 150, 200, 250, 300, 400, 500, 600 or 760 mmHg. In some cases, a microfilter prepared by a method provided herein has a tensile strength greater than about 75, 100, 150, 200, 250, 300, 400, 500, or 600 MPa. In some cases, the material electroplated on the mechanical support comprises a metal. Non-limiting examples of metals in a microfilter include nickel, gold, cobalt, chromium, copper, iron, manganese, platinum, zinc, palladium, titanium, silver, molybdenum, tungsten, aluminum, indium, carbon, silicon, tin, lead and alloys and combinations thereof. In some methods the layer of metal comprises nickel, palladium or a combination of nickel and palladium.

An exemplary method for microfilter fabrication comprises a) providing a mechanical support comprising a layer of conductive material and a plurality of pillars; b) electroplating the layer of conductive material with a layer of metal; and c) removing the layer of metal from the mechanical support to obtain the microfilter comprising the layer of metal and a plurality of pores within the metal layer, wherein the position of the plurality of pores corresponds to the position of the plurality of pillars on the mechanical support. In some embodiments, the layer of conductive material comprises titanium, gold, nickel, silver, cobalt, chromium, copper, iron, manganese, platinum, zinc, palladium, molybdenum, tungsten, aluminum, indium, carbon, silicon, tin, lead or an alloy or combination thereof. In some embodiments, the plurality of pillars comprise photoresist, for example, a positive photoresist such as AZ P4620. In some embodiments, the photoresist is spin-coated on the mechanical support. In some methods, the microfilter is functionalized on a surface with a biomolecule or chemical moiety that binds or otherwise interacts with a target cell.

An exemplary method for microfilter fabrication comprises a) providing a mechanical support comprising a layer of conductive material; b) applying a layer of photoresist on the layer of conductive material; c) patterning the layer of photoresist to expose regions of the layer of conductive material, wherein the photoresist pattern comprises a plurality of pillars of photoresist; d) electroplating the exposed regions of the layer of conductive material with a layer of metal to a height equal to or less than the height of each of the plurality of pillars; e) dissolving the plurality of pillars of photoresist; and f) separating the layer of metal from the mechanical support to obtain the microfilter, the microfilter comprising the layer of metal and a plurality of pores. Some methods further comprise underetching the conductive layer, thereby allowing the layer of metal to be released from the mechanical support. Some methods further comprise cleaning the microfilter. For example, by ultrasonic cleaning in an aqueous and/or organic solution. Some methods further comprise annealing the microfilter. Annealing includes heating and in some instances, improves flatness of the microfilter.

In some embodiments, a mechanical support comprises a silicon wafer. In some cases a mechanical support has a thickness of between about 0.5 to about 6 inches. In some embodiments, a layer of conductive material comprises titanium, gold, nickel, silver, cobalt, chromium, copper, iron, manganese, platinum, zinc, palladium, molybdenum, tungsten, aluminum, indium, carbon, silicon, tin, lead or an alloy or combination thereof. In some cases, the layer of conductive material is deposited on the mechanical support by vapor deposition. In some embodiments, the plurality of pillars comprise photoresist, for example, a positive photoresist such as AZ P4620. In some cases, the photoresist is spin-coated on the mechanical support. In some embodiments, the photoresist is spin-coated on the mechanical support. In some methods, the microfilter is functionalized on a surface with a biomolecule or chemical moiety that binds or otherwise interacts with a target cell.

Figure 5:
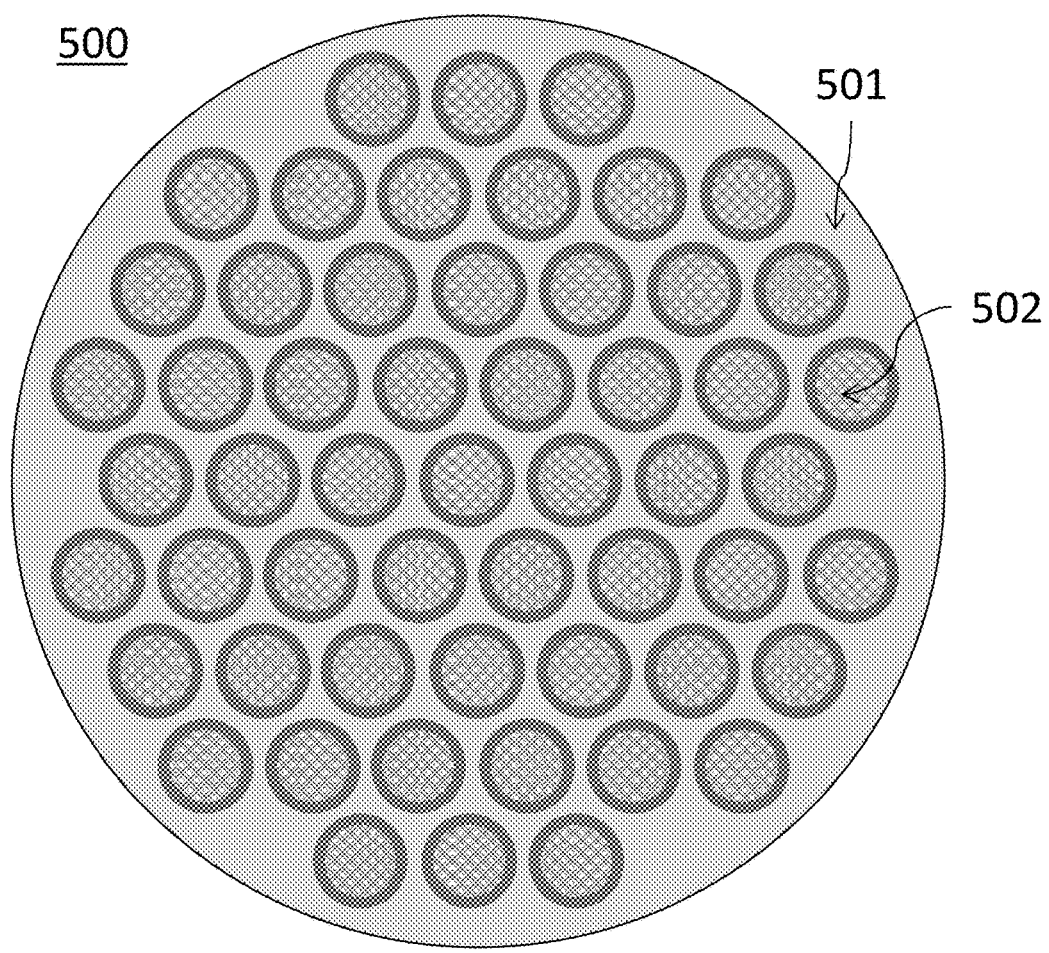
FIG. 5 is an illustration of a plurality of microfilter membrane structures during fabrication.

Turning to the figures, FIG. 5 shows a silicon wafer 500 used as a mechanical support for a microfilter fabrication process as described herein. The mechanical support comprises a surface 501 and a plurality of prepared microfilters 502. As an example, silicon wafer 500 is 4 inches thick.

Figure 6:
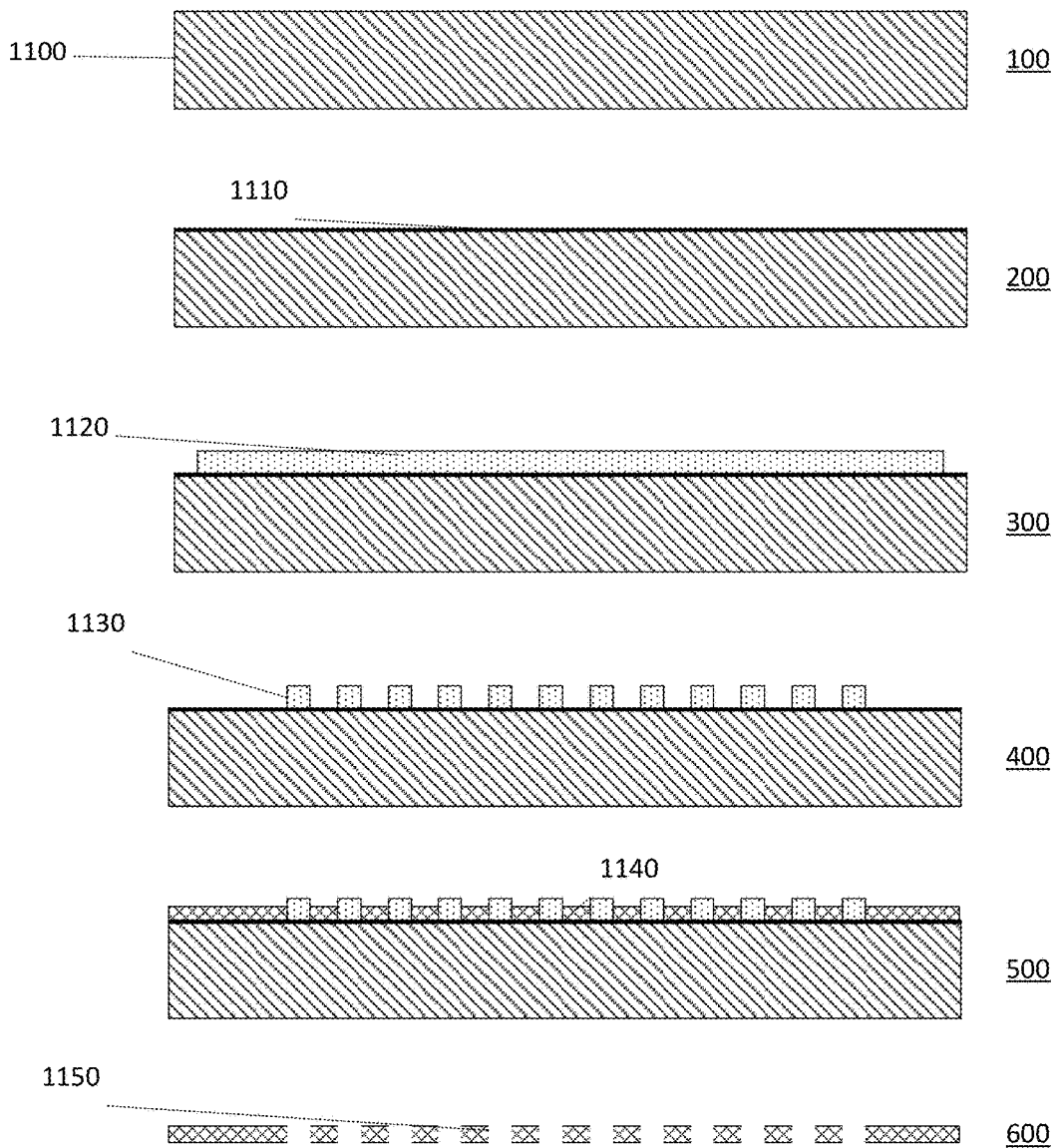
FIG. 6 is a side view of a mechanical support showing multiple steps during the microfilter fabrication process.

A schematic for an exemplary photolithographic process is shown in FIG. 6. Shown in panel 100 is a side view of a mechanical support 1100, such as a silicon wafer. A titanium layer on the order of ¼ to ⅓ micron in thickness 1110 is deposited on the support 1100 using a vapor deposition process (panel 200). The titanium material has good adhesion to the support and acts as an adhesion layer for a subsequent vapor deposited gold layer (not shown), also approximately ¼ to ⅓ micron in thickness. The function of the gold layer is to act as a conductive layer for electroplating. After the gold layer is deposited, a positive photoresist 1120 such as AZ P4620 or other positive photoresist is applied as a liquid and spin-coated (panel 300). The spin coating is performed at a relatively low rpm, e.g., approximately 150 rpm for 20 seconds, or as appropriate to achieve a photoresist thickness of approximately 12 microns. The photoresist is then softbaked for between 70 degrees C. for 60 seconds and 100 degrees C. for 4 minutes. The photoresist is then softbaked in preparation for exposure and development.

Figure 7:
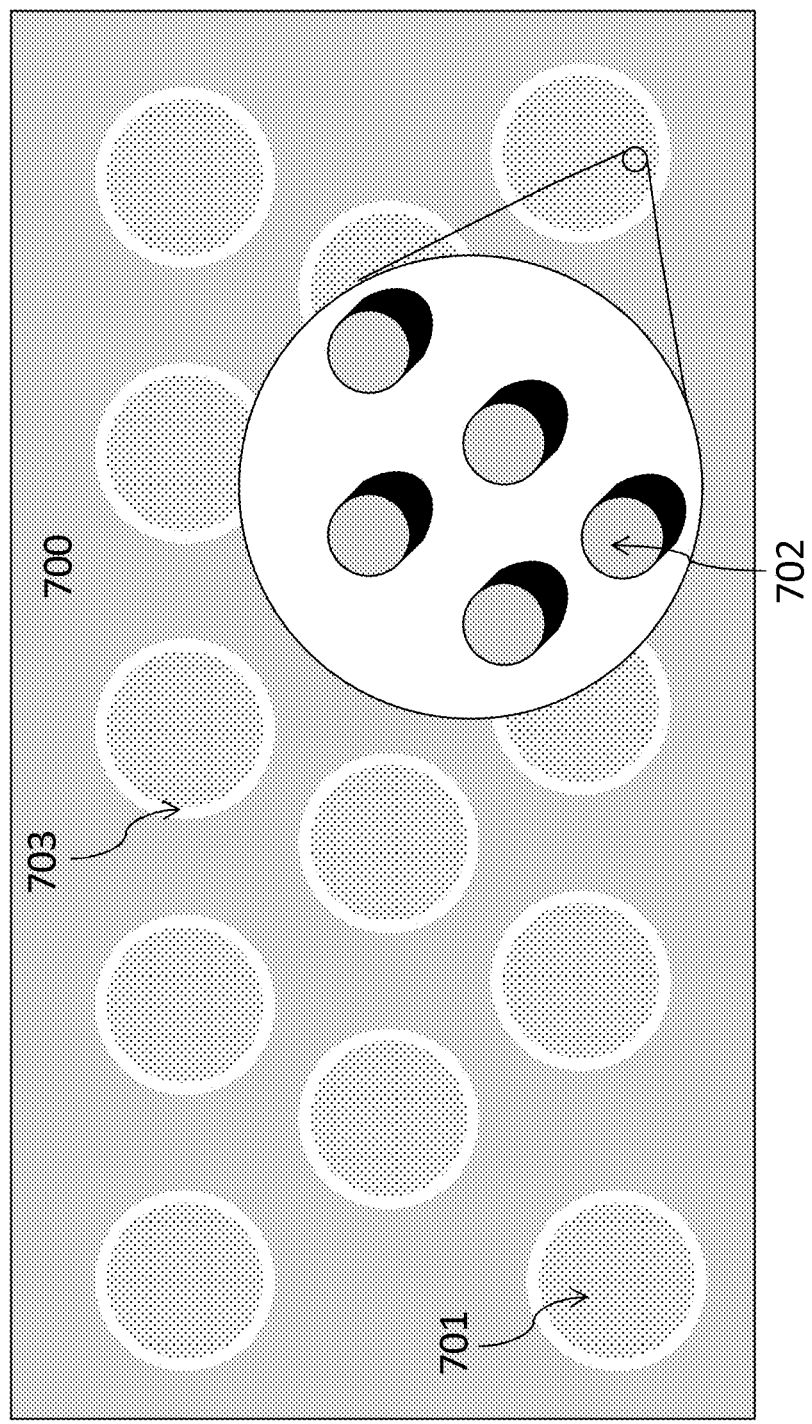
FIG. 7 is a magnified image showing several photoresist pillars after exposure, development, and rinsing of the photoresist.

To obtain a plurality of posts or other filter structures on the mechanical support, a photolithography mask is prepared with a pattern to selectively expose layers of photoresist on the mechanical support. The photoresist is exposed, using a stepping process to expose each filter structure location on the wafer. Approximately 40, 13 mm microfilters can be exposed on a 4 inch wafer. The positive photoresist is developed, which causes the unexposed areas to dissolve. After curing, the resulting photoresist pattern appears as a set of filter areas, wherein there is a region of pillars of photoresist 1130 (panel 400). Turning to FIG. 7, a view of a surface of a support 700 is shown comprising a plurality of regions 701 for microfilter fabrication, each of the plurality of regions comprising a plurality of pillars of photoresist 702. In one embodiment, each pillar 702 is approximately 8 microns in diameter and approximately 12 microns high on 16 micron centers. A circular trench 703 2 mm wide and 13 mm in diameter which will form a supporting ring around each 9 mm diameter circular filter area is also shown.

Figure 8:
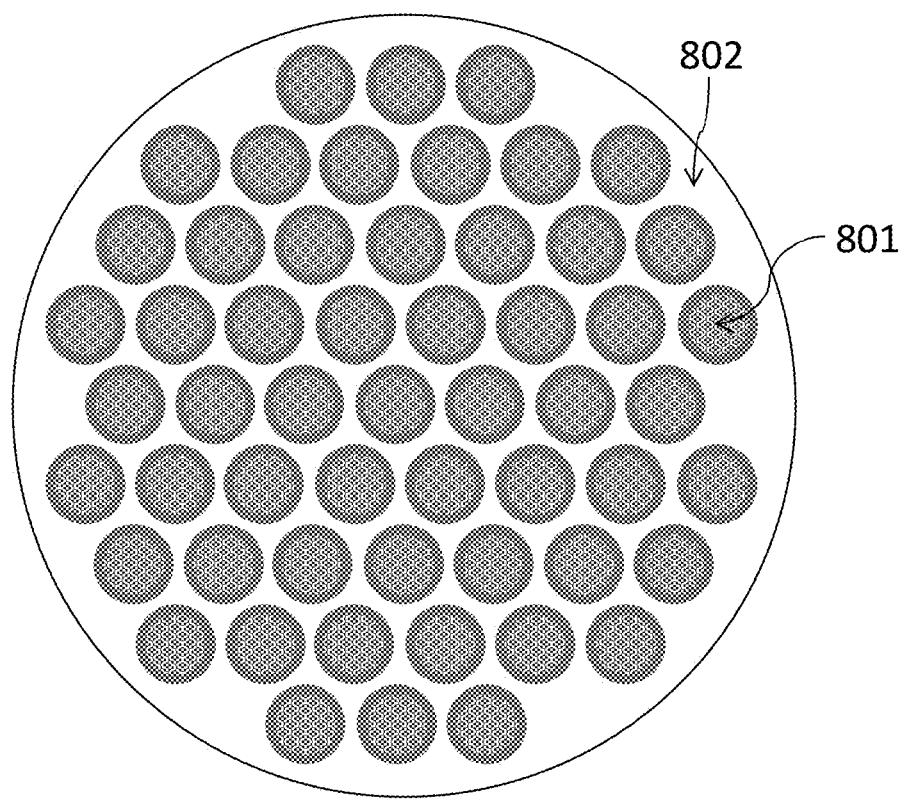
FIG. 8 is an illustration of a plurality of microfilter membrane structures adhering to a mechanical support after photoresist dissolves and before floating the filters off the support.

Referring back to FIG. 6, the wafer with the photoresist pattern (panel 400) is then electroplated with nickel-palladium to a thickness of approximately 8 microns 1140 (panel 500). Accordingly, at each pore location, the photoresist pillars rise approximately 3-4 microns above the nickel-palladium layer. The photoresist is then dissolved, leaving a plurality of filter membrane structures 801 adhering to the wafer 802 as shown in FIG. 8. After this step, the titanium and gold layers are underetched, allowing the nickel-palladium microfilter membranes to float free from the wafer 1150 (panel 600). The microfilters are then cleaned, and can be annealed to improve flatness.

Figure 9:
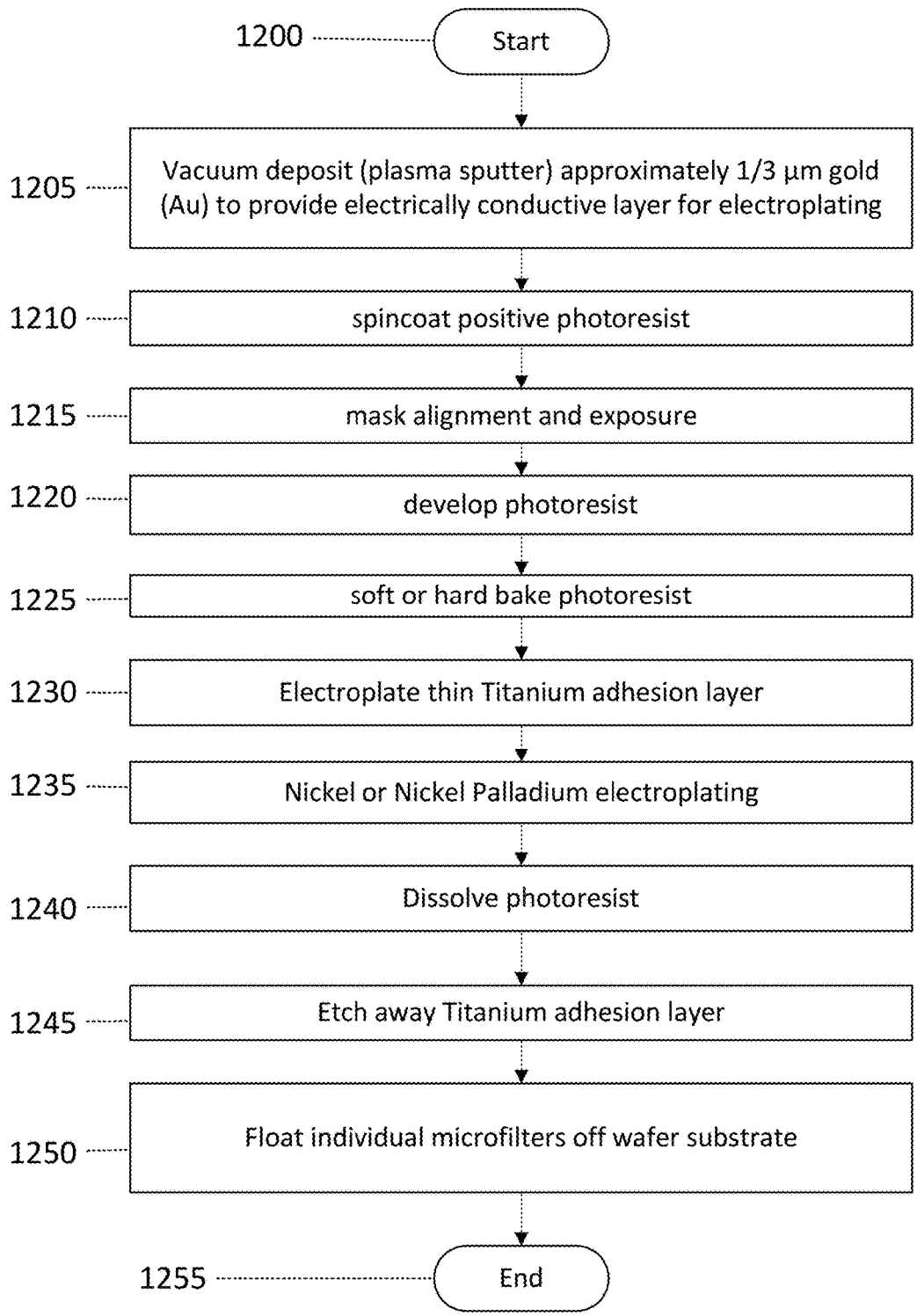
FIG. 9 is a flow chart illustrating the steps in an exemplary microfilter fabrication process.

A flow chart outlining a general process of photolithography is shown in FIG. 9. A mechanical support is a starting product (1200) for microfiltration fabrication. A conductive material such as gold is vacuum deposited onto the mechanical support (1205). A positive photoresist is spincoated onto the conductive layer (1210). A photolithography mask is aligned over the support and the photoresist is patterned by exposure through the mask (1215). The photoresist is developed (1220) and then soft or hard baked (1230). An adhesion layer (e.g., comprising titanium) is electroplated onto the surface of the support (1235). A layer of metal (e.g., nickel and/or palladium) is electroplated onto the adhesion layer (1235). The patterned photoresist is dissolved (1240) and the titanium adhesion layer etched away (1245), allowing individual microfilters to float free from the support surface (1250), where they are collected and used, for example, for microfiltration of a biological sample as described elsewhere herein (1255).

Microfiltration System and Methods

Microfilters described herein are often provided on a holder and/or cassette during microfiltration and/or imaging. In some embodiments, a microfiltration holder is a slide. In some methods, a microfilter is held by a cassette during microfiltration and a slide during imaging. In some cases a cassette functions as a slide holder or vice versa.

Figure 10:
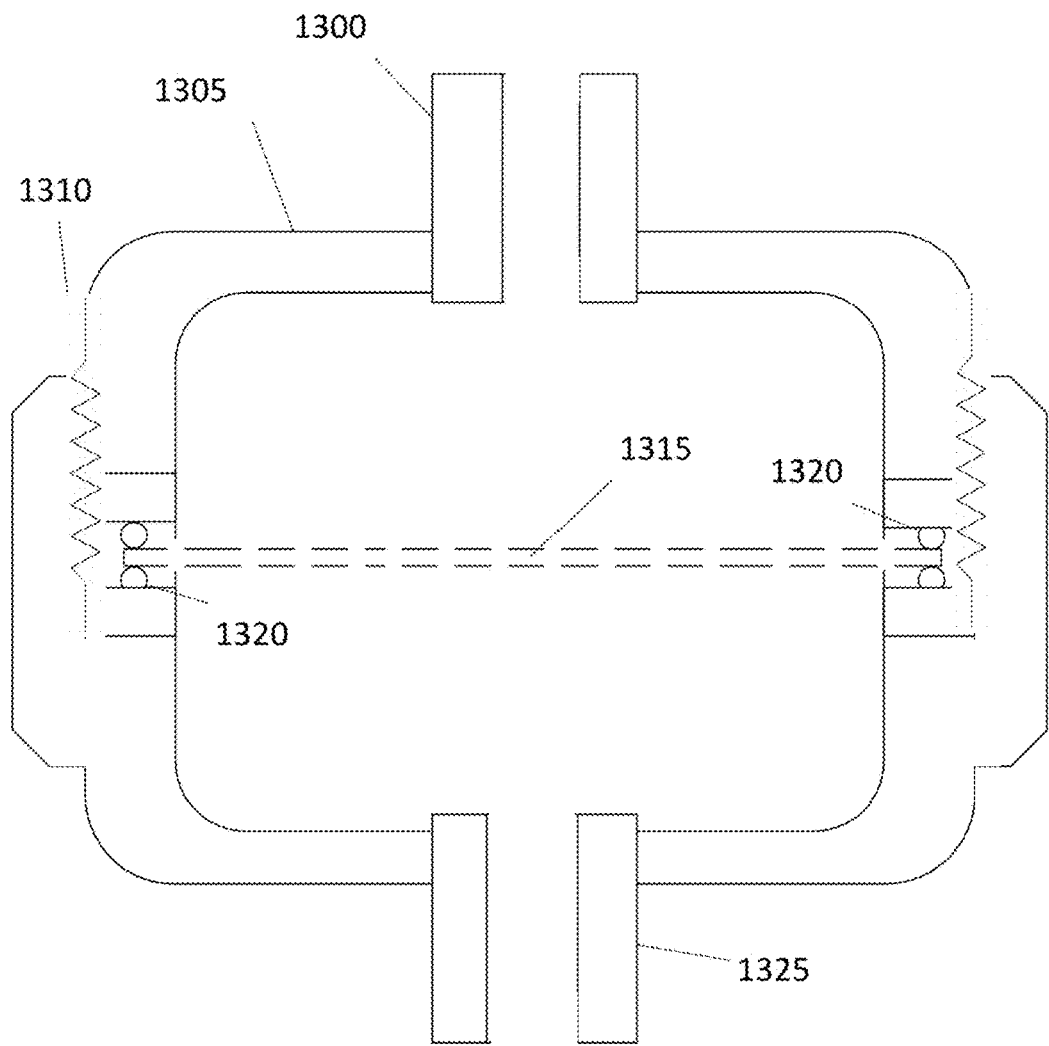
FIG. 10 shows a first embodiment of a microfilter holder cassette.

An example of a microfilter cassette assembly is shown as a side cutaway view in FIG. 10, where microfilter 1315 is held during filtration. The periphery of the microfilter is retained between two O-rings 1320, which may be made of silicone or other similar material. The O-rings are in turn retained by an upper microfilter cassette portion 1305 and a lower microfilter cassette portion 1330. The upper and lower portions may be threaded to allow a secure connection that will provide sealing pressure on the O-rings 1320 to provide a fluid seal. A side of the cassette where the upper and lower portions are connected is shown by reference number 1310. Input sample and other material may be input through port 1300. Material may be evacuated, or in some cases input such as PBS priming, through evacuation port 1325.

Figure 11A:
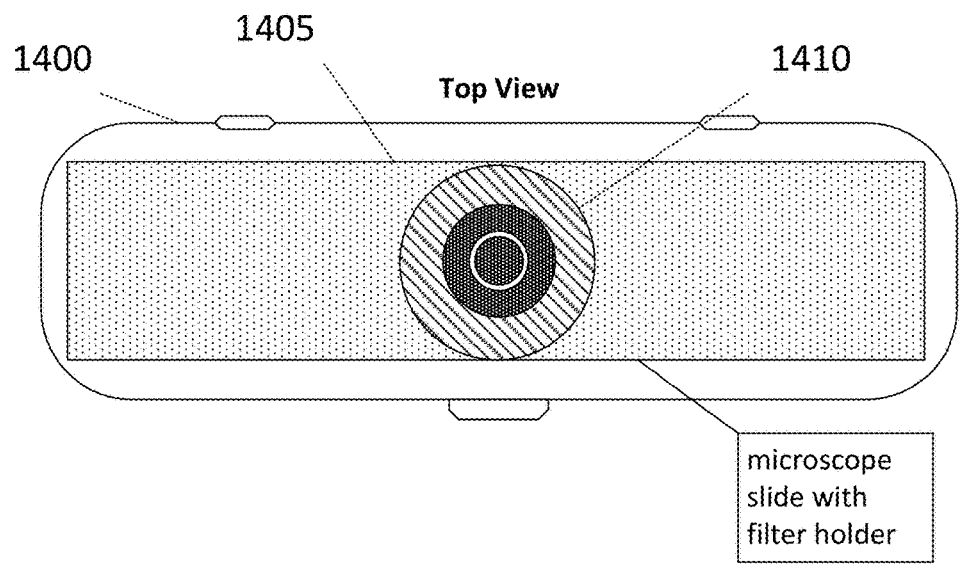
FIG. 11A shows a top view of a second embodiment of a microfilter cassette.
Figure 11B:
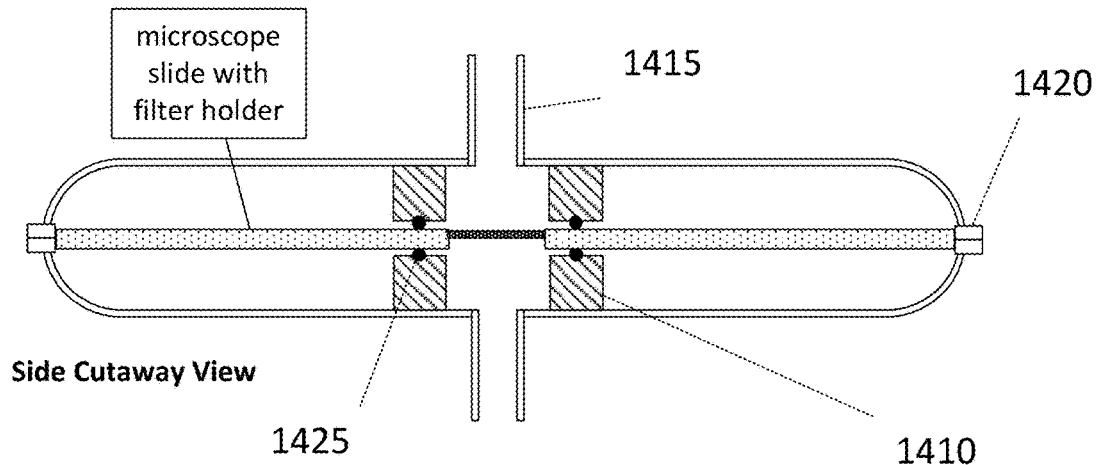
FIG. 11B shows a side cutaway view of a second embodiment of a microfilter cassette.

Another example of a microfilter cassette assembly is shown in FIG. 11A as a top view and FIG. 11B as a cutaway side view of microfilter holder 1400. In this embodiment, the microfilter is attached to a microscope slide 1405 having a central hole 1410 of a size sufficient to allow free flow of fluids being filtered but allowing the periphery of the microfilter membrane to be attached to the microscope slide with an adhesive material. The microfilter membrane is permanently affixed to the microscope slide, and the slide and microfilter are provided as an integral unit. The microfilter holder cassette has cylindrical faces 1410 that hold O-rings 1425. O-rings 1425 are pressed into contact with the microscope slide so as to provide a hydraulic seal. A mechanical press is used to provide the correct pressure and orientation of the O-rings onto the microscope slide. This allows the input port 1415 and exit port 1430 to be used for all filtration fluid processing. In some embodiments, the microfilter membrane never needs to be handled by itself, but is always handled while bonded to the microscope slide, for great improvement in handling.

Figure 12:
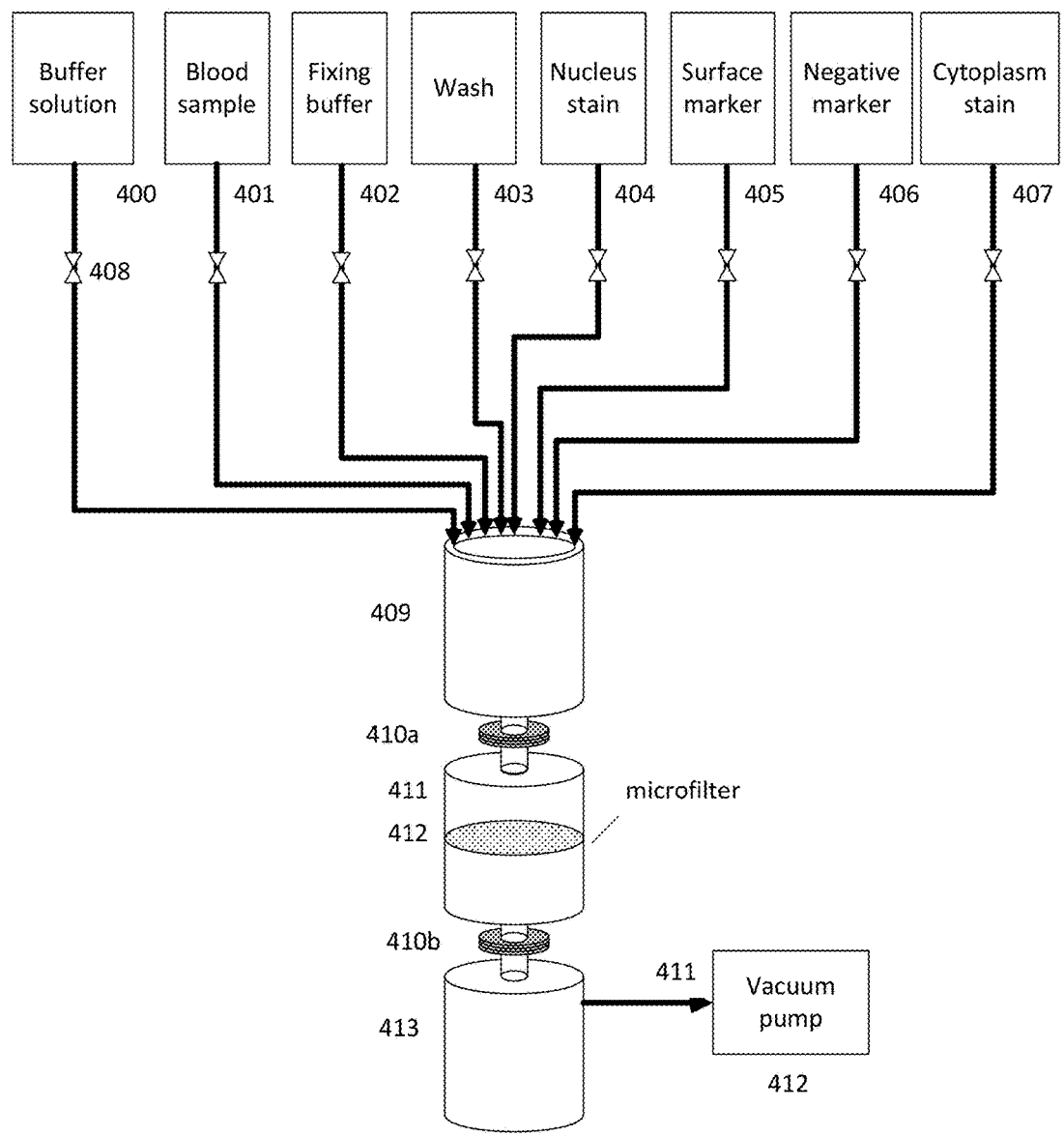
FIG. 12 shows a microfluidic control system for controlling a filtration process.

A system for microfiltration comprising a microfilter cassette assembly is shown in FIG. 12. The system uses microfluidic plumbing for the application of the microliter quantities of reagents to the surface of a microfilter that may comprise retained target cells. Material reservoirs 400 through 407 are controlled manually and/or automatically. As an alternative to this system configuration, a biological sample and reagents will follow different pathways in any manner to maximize the amount of reagent applied to the microfilter membrane.

In some embodiments, a microfiltration system comprises a syringe pump. In some methods, the syringe pump is used in a vertical orientation to draw a sample from a collection tube through the microfilter and into the waste syringe. In some embodiments, the syringe pump manually or automatically draws a 7.5 ml sample through the microfilter in a 3 minute or longer period. The slow filtration rate keeps pressure differentials to a minimum to allow target cells such as CTCs and TDMCs to be filtered without damage. In other embodiments, a sample is passed through the microfilter at a higher rate while maintaining integrity of the target cell. Non-limiting examples of sample flow rates through a microfilter include: 1-20 ml/min, such as 1, 2, 3, 4, 5, 6, 7, 8, 9, 10, 11, 12, 13, 14, 15, 16, 17, 18, 19, 20 and any range there between. In some methods, a microfilter has sufficient strength to pass a fluid through the microfilter at a rate greater than 10, 11, 12, 13, 14, 15, 16, 17, 18, 19 and 20 ml/min. The fluid need not be a biological sample and is inclusive of buffers, probes, and other reagents used in a microfiltration, washing, staining, and/or fixation method. Accordingly, in some methods a biological sample such as blood is passed through a microfilter at a first rate, and one or more fluids are passed through the microfilter at a second rate. The second rate may be higher or lower than the first rate.

In some embodiments, a microfilter is held within a cassette, where the top of the cassette is connected to an input syringe and the bottom is connected to a waste or retention syringe. In some configurations, a 60 ml syringe for waste retention is mounted vertically in the syringe pump, with the plunger at the bottom and the tip projecting upwards so as to be accessible for mounting the assembled microfilter cassette. In some configurations, an input syringe is a 30 ml syringe containing a sample to be filtered. The input syringe is attached to the top of the assembled microfilter cassette, which is attached in turn to the retention syringe. The connection between the input syringe and/or retention syringe with the cassette may be via a Luer Lock.

Provided herein are methods for filtering a biological sample to enrich on the surface of a microfilter one or more target cells present or possibly present in the biological sample. In some cases, the biological sample is prepared prior to filtration. In other cases, the biological samples is applied directly to microfilter. Examples of biological samples include blood, serum, plasma, and any sample processed from blood, and samples from a subject comprising cellular material. In some embodiments, a blood sample is collected in a tube with an anticlotting agent such as EDTA or Heparin. In some cases, the blood sample is combined with a buffer and/or labeling reagent prior to filtration. In some embodiments, a biological sample is combined with one or more probes prior to microfiltration. In an initial step of a microfiltration method, a biological sample is drawn at very low or low pressure through the pores in the filter membrane. Some or a significant portion of target cells which are larger than the diameter of the pores, if present, are retained on the surface of the microfilter. In cases where the microfilter will be imaged by fluorescence microscopy, the microfilter is optionally buffered, fixed, and/or stained. If the microfilter is not already held on a microscope slide, the microfilter is then mounted onto a microscope slide for imaging.

Referring back to the non-limiting system of FIG. 12, a microfilter 412 is held within a microfilter holder 411. The microfilter is washed with a buffer from reservoir 400, which is controlled by opening and closing of a valve 408. For all materials applied to microfilter 412 using the system configured in FIG. 12, the materials pass through a first container 409 (in some cases, an input syringe), a first connection 410a, microfilter holder 411 and microfilter 412, a second connection 410b, and a second container 413 (in some cases, a waste syringe). The materials are passed through the system by gravity or at a low pressure using a vacuum pump 412 connected 411 to the second container 413. A sample such as blood is transferred from reservoir 401 through filter 412. One or more fluids are passed through the system: a fixing buffer from reservoir 402, a wash from reservoir 403, a nucleus stain from reservoir 404, a surface marker from reservoir 405, a negative marker from reservoir 406, a cytoplasm stain from reservoir 407, or any combination thereof. In some embodiments, an additional fluid is added. In some embodiments, one or more fluids, such as one comprising a staining reagent and/or probe, are combined with the sample prior to microfiltration. Fluids may be applied together or sequentially. The microfilter is then removed for detection of the stains using, for example, fluorescence microscopy.

Cell Detection Methods and Systems

In one aspect of the disclosure, provided herein are methods and systems for analyzing a cell signature of a cell of interest in a biological sample to determine and/or characterize the cell of interest as a target cell. In some methods, the biological sample has been enriched for the target cell using any available method which will capture or otherwise concentrate a target cell from a sample of a subject. In some cases, an enriched sample is enriched on a surface and/or transferred to a surface and a target cell, if present, is analyzed on that surface. An exemplary surface is a microfilter surface, where a biological sample is passed through the microfilter to retain large target cells such as tumor derived cells on the microfilter surface.

Analysis of a cell signature includes detecting the presence or absence of a target cell, and if the target cell is present, one or more characteristics of the target cell. In some embodiments, a target cell comprises one or more distinguishing features (e.g., morphology, nucleus size, nucleus number) and/or biomarkers that are detected in the analysis. One method for identifying if a cell of interest is a target cell comprises applying to a surface comprising or suspected of comprising a target cell one or more probes that visualize a distinguishing feature and/or the presence and/or absence of one or more biomarkers of a target cell. In exemplary methods, the probe is a fluorescent probe and the methods comprise fluorescent microscopy.

A non-limiting example of a method for preparing a biological sample for analysis by fluorescent microscopy is outlined herein. The method generally involves the capture of a potential target cell, such as a potential TDMC, in a filtration process comprising passing a blood sample through a microfilter under modest pressure and then treating the microfilter with a fixation buffer and stains or dyes. In some embodiments, the stains are DAPI, and fluorescent probes comprising fluorophores conjugated to anti-CD 45, anti-EpCAM, and anti-Ck 8, 18, 19. The probes may comprise any antigen or antibody that binds to a target cell to distinguish the target cell from non-target cells. In some methods, an additional stain or probe is applied to the microfilter to determine different characteristics of the filtered sample. For example, if the target cell is a TDMC, the characteristics can include the type of tumor from which the TDMC was derived.

In some embodiments, a method for microfiltration comprises: (a) providing a biological sample, and providing a microfilter held by a microfilter holder; (b) passing the biological sample through the microfilter to enrich for cells larger than the size of the microfilter pores on the surface of the microfilter; (c) applying to the microfilter surface one or more probes to detect a signature of a cell of interest; and (d) comparing the signature of the cell of interest to a target cell signature to determine if the cell of interest is a target cell.

In some methods, the biological sample is a blood sample from a subject, for example, a blood sample with a volume between about 0.5 mL and 20 mL, or about 5, 5.5, 6, 6.5, 7, 7.5, 8, 8.5, 9 ml, or any range within 0.5 mL and 20 mL. In some cases, the biological sample is a fixed blood sample. In some methods, the biological sample is passed through the microfilter by drawing the sample from an input syringe through the microfilter and into the retention syringe. In some cases, the biological sample is passed through the microfilter at a low pressure or with gravity.

In some methods, the microfilter comprises a metal layer, as described in various embodiments throughout this disclosure. For example, the microfilter comprises nickel, palladium or a combination thereof. In some embodiments, the microfilter has low fluorescence for fluorescent microscopy imaging. In some cases, low autofluorescence is less than parylene-C filter material in the FITC, TRITC, and Cy5 fluorescent channels used in fluorescence microscopy, by relative measurement. In some embodiments, the layer has an autofluorescence that is less than about 80%, 70%, 60%, 50%, 40%, 30%, 20%, 10%, or 5% of the autofluorescence of parylene-C in the FITC, TRITC, and/or Cy5 fluorescent channels, by relative measurement. In some cases, the metal layer has an autofluorescence less than about 20% of the autofluorescence of parylene-C in the FITC channel. In some cases, the metal layer has an autofluorescence less than about 20% of the autofluorescence of parylene-C in the TRITC channel. In some cases, the metal layer has an autofluorescence less than about 50% of the autofluorescence of parylene-C in the Cy5 channel. In some cases, the metal layer has low autofluorescence from excitation wavelengths of about 330 nm to about 650 nm, when auto fluorescing in emission wavelengths of about 400 nm to about 800 nm.

In some methods, the microfilter holder is part of a microfilter cassette and the cassette is attached on one side to an input syringe and on the other side to a retention syringe. In some such cases, the method further comprises assembling the microfilter cassette. In some cases, the microfilter is washed by application of a wash solution to the microfilter prior to application of the biological sample. In some methods, the microfilter is washed with a wash solution after filtration of the biological sample. In some embodiments, the method comprises applying to the microfilter a permeabilization buffer after the microfilter is passed with the biological sample and then washing the microfilter after application of the permeabilization buffer. In some methods, the surface of the microfilter is blocked, for example, with a solution of BSA.

In some methods, the one or more probes comprises an antibody having an antigen binding domain specific for one or more of the following antigens: Cytokeratins 8, 18, 19; EpCAM; CD45; PSMA; AFP; CEA; CA-125; MUC-1; ETA; tyrosinase; MAGE; VEGF; Her2nue; B2M; c-kit/CD117; ER; PR; fibrin and fibrinogen. In some methods, the one or more probes comprises FITC (anti-Cytokeratins 8, 18, 19), TRITC (anti-EpCAM), and Cy5 (anti-CD45)], DAPI or a combination thereof. The one or more probes may be applied to the microfilter at one or separate times, optionally with a wash between applications, if applicable. In some embodiments, the one or more probes is mixed with the biological sample and applied to the microfilter with the biological sample.

In some embodiments, the microfilter cassette is disassembled and the microfilter positioned on a microscope slide, optionally with a reagent such as anti-fade reagent and a cover slip. In other embodiments, the microfilter is imaged within the cassette.

In some embodiments, potential target cells enriched on a surface of a microfilter are detected by an emission or absorption of light or electromagnetic energy, either in the visible range or otherwise from an optically-detectable label on a probe applied to the microfilter. Optically detectable labels include, without limitation, fluorescent, chemiluminescent, electrochemiluminescent, luminescent, phosphorescent, fluorescence polarization, and charge labels. In some embodiments, a fluorescently labeled probe is active only in the presence of a target molecule so that a fluorescent response from a sample signifies the presence of the target molecule. In some instances, fluorescent probes increase their fluorescence in proportion to the quantity of target present on the microfilter. This is useful where different amounts of a biomarker in a target cell, such as tumor derived cell, indicates a different type and/or stage of a disease such as cancer.

Examples of fluorophores useful in a fluorescently labeled probe described herein include, but are not limited to, 4-acetamido-4'-isothiocyanatostilbene-2,2'disulfonic acid; acridine and derivatives: acridine, acridine isothiocyanate; 5-(2 aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumarin 151); cyanine dyes; cyanosine; 4',6-diaminidmo-2-phenylmdole (DAPI); 5 r 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfiuorescein (FAM), 5-(4,6-dichlorotriazin-2-yl)ammofluorescem (DTAF), 2',7-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Cyanine-3 (Cy3); Cyanine-5 (Cy5); Cyanine-5.5 (Cy5.5), Cyanine-7 (Cy7); IRD 700; IRD 800; La Jolta Blue; phthalo cyanine; and naphthalo cyanine; any of the fluorescent labels available from Atto-Tec, for example, Atto 390, Atto 425, Atto 465, Atto 488, Atto 495, Atto 520, Atto 532, Atto 550, Atto 565, Atto 590, Atto 594, Atto 610, Atto 61 IX, Atto 620, Atto 633, Atto 635, Atto 637, Atto 647, Atto 647N, Atto 655, Atto 680, Atto 700, Atto 725, Atto 740; Rhodamine, Fluoroscein, dye derivatives of Rhodamine, dye derivatives of Fluoroscein, 5-FAM™, 6-carboxyfluorescein (6-FAM™), VIC™, hexachloro-fluorescein (HEX™), tetrachloro-fluorescein (TET™), ROX™, and TAMRA™.

The detection or monitoring of light emitted from one or more fluorophores may be performed qualitatively and/or quantitatively. Qualitative detection includes measurement of the presence or absence of a signal, and/or a change in a signal from present to absent, or absent to present, among others. As described herein, the presence or absence refers to either a whole signal (such as any light) and/or a component of the signal (such as light of a particular wavelength (or wavelength region), polarization, and/or the like. Quantitative detection can include measurement of the magnitude of a signal, such as an intensity, wavelength, polarization, and/or lifetime, among others. Quantitative detection may involve the addition of a standard via spiking, where the standard is added to the solution to be analyzed or to the filter, to enable calibration of measured signals.

In some embodiments, a microfilter comprising a sample enriched for a target cell is treated with one or more fluorescent probes. As used herein, a microfilter comprising a sample enriched for a target cell or a microfilter which has had a biological sample passed through it, may or may not comprise the target cell. In some cases, a biological sample is enriched for a target using microfiltration, but the target cell is not present in the biological sample and therefore not present on the surface of the microfilter. In some such cases, the absence of one or more features and/or biomarkers in cells of an enriched sample indicates the absence of the actual target cell in the enriched sample, and thus the biological sample input on the microfilter.

Figure 13:
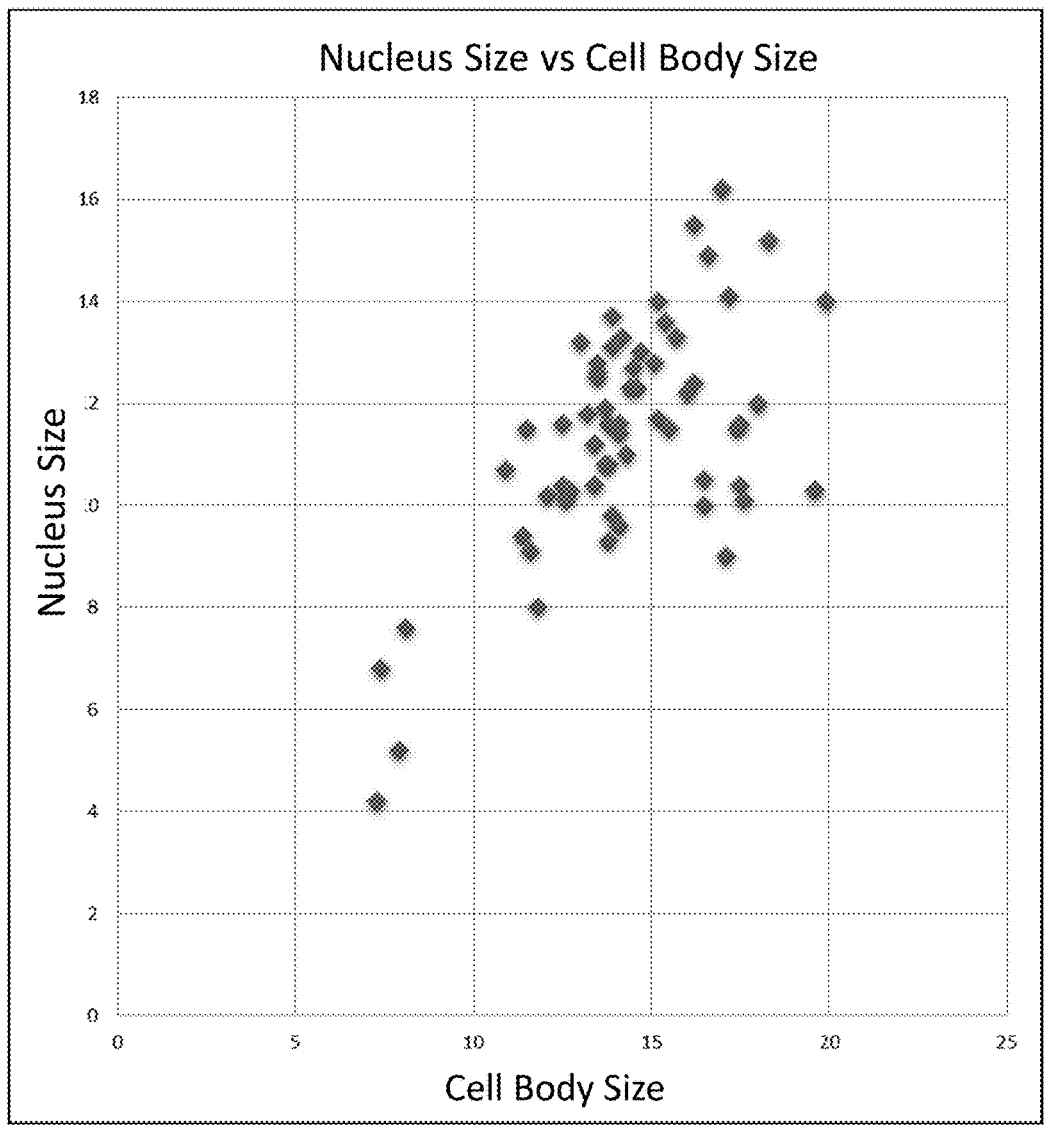
FIG. 13 is a plot of TDMC nucleus size versus cell body size isolated from a set of blood samples using microfiltration.
Figure 14:
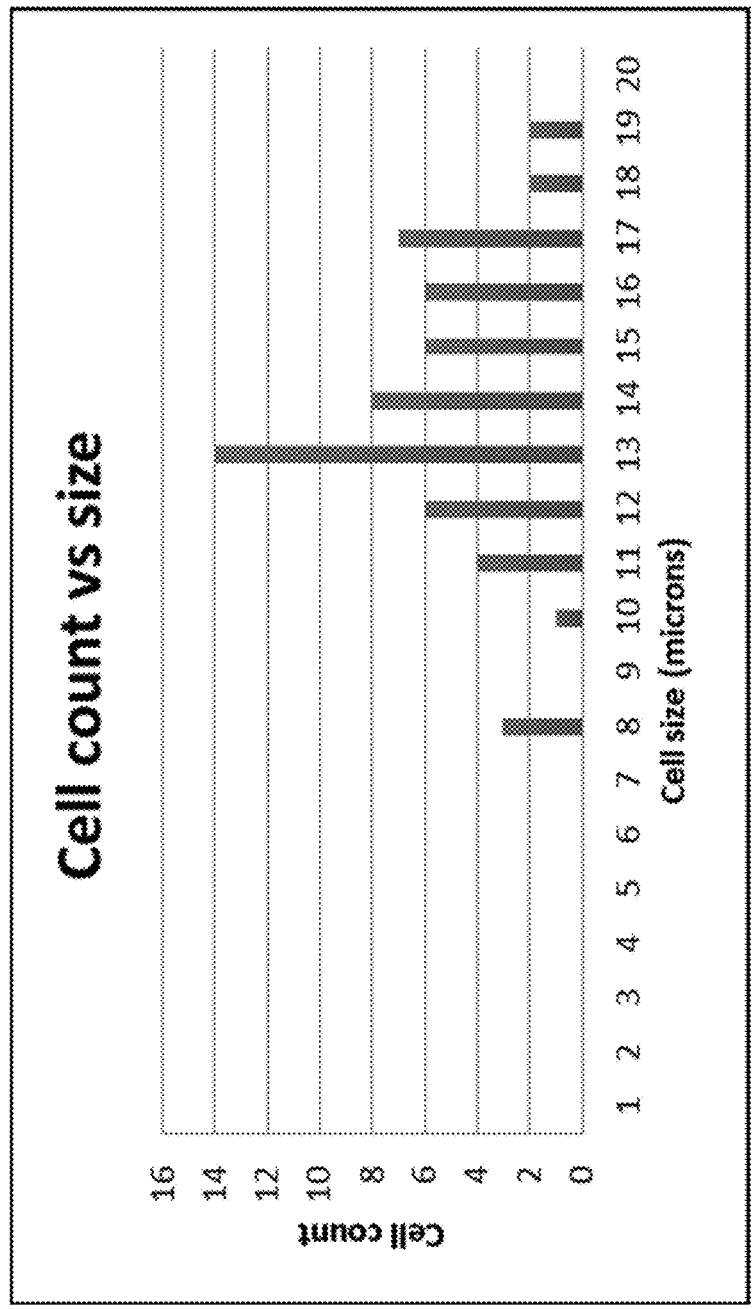
FIG. 14 is a chart showing TDMC cell count as a function of size in a set of blood samples.

A fluorescent probe useful for detecting cells with irregular or multiple nuclei, such as tumor derived cells, is DAPI. FIG. 13 shows a plot of nucleus size versus cell body size in a set of microfilter samples comprising an enriched sample of cells imaged using a DAPI probe. FIG. 14 shows a plot of the cell count versus cell size for the same set of samples. The images were first observed for nuclei having a longest diameter between about 6 and 16 microns, having an irregular form, or having multiple nuclei. In some cases, cells with irregular, large nuclei and/or multiple nuclei are indicative of a tumor derived cell such as a TDMC or CTC. To further identify the signature of stained cells, the set of microfilters were also treated with a probe comprising a fluorophore and anti-CD45 antibody; and a probe comprising a fluorophore and anti-EpCAM antibody. The CD45 channel was then observed for an anti-CD45 signal co-located with the DAPI nucleus signal. The EpCAM channel was observed for an anti-EpCAM signal in the cells.

In some embodiments, a fluorescently labeled probe specific for a biomarker of a target cell engages in non-specific binding, also referred to as cross-reactivity or cross-talk, with a moiety other than the specific biomarker in a sample. In such cases, the cross-reactive or cross-talk fluorescent signal is considered background or noise. In some embodiments, detecting the presence of a signal from a fluorescently labeled probe specifically bound to a biomarker of a target cell comprises measuring light emitted from the specifically bound probe and subtracting from that measurement a determined baseline level of background signal or noise. In some cases, this subtraction method is calibrated according to the intensity of light of an image of the sample. In some embodiments, a normalized background signal is subtracted from an image of a sample, where the normalized background signal is calibrated by measurement of a signal from an internal standard applied to the sample prior to, during, or after processing, e.g., processing by microfiltration enrichment.

For methods comprising optical detection of a signature of a target cell, a microscope or similar imaging acquisition device is employed. In some embodiments, a microscope is an optical inverted microscope comprising one or more of: a computer or manually controlled stage; an objective; and 1-10 fluorescence channels to observe cells present on the microfilter membrane. Some microscopes comprise 1, 2, 3, 4, 5, or 6 channels. In some cases, a microscope comprises four channels. For example, the four channels used to image a microfilter are DAPI, FITC, TRITC, and Cy5. A channel may be any fluorescent channel selected for compatibility with a fluorophore selected to be combined with a chosen molecule such as an antibody. A set of all channels is referred to as a frame. In some cases, each channel is recorded as a grey-scale image. The individual channels may be false colored, and the false colored channels may be combined in a composite image. In some embodiments, regardless of the signal from a specific channel, one or more channels approximately co-locate with the associated nucleus on the DAPI channel.

In some methods described herein, a microfilter enriched for a target cell is imaged using a multichannel fluorescence microscope. In some methods, the entire surface of the microfilter membrane is scanned first. To scan the entire surface of the microfilter membrane at a useful magnification for a tumor derived target cell identification of 40×, this scan will typically produce approximately 500, 4-channel frames. Alternatively, the membrane surface could be initially scanned at 20×, producing approximately 140 frames, then 40× images could be taken on regions of interested flagged by observing the 20× scan.

A human observer will typically look at a composite image, and then look at the individual channel images to verify takeup of the fluorescent probes (or stains), however, this is not required. In part, this may be performed because faint traces in one channel may be hidden by strong signals from other channels in the composite image Image processing using well known image processing software such as ImageJ (NIH), or Fiji (open source ImageJ package, Fiji Is Just ImageJ) may be used to enhance visibility of features in the various channel images.

In some embodiments, a microscope is programmed to automatically register the position of one or more slide mounted microfilters. Multiple microfilters may be mounted on individual microscopes slides in a multiple slide carrier for mounting on the microscope stage. Automatic registration may be performed using contrast or other optical feature. In some cases, registration marks are etched into or otherwise applied to each filter to enable more accurate registration. Multiple microfilters on multiple slides may be placed in a slide holder cassette and secured into the microscope stage for batch image acquisition. In some embodiments, after registration, a focus-only brightness surface scan is performed on each entire filter surface to determine the z-axis height of the filter surface, to compensate for irregularities, tilt, and warpage of the filter surface. The results of the surface scan may be stored in a memory for use during the image capture phase. In some embodiments, when image capture is performed, multiple frames are be captured at each microscope stage position in a z-stack having a focus plane centered on the filter membrane surface height previously determined to ensure an image in correct focus even if the cells are not in contact with the filter surface. The nominal focus center of the z-stack may be offset to adjust for the different wavelengths of the channels. Thus, all the DAPI images in a z-stack may be offset by a fixed amount, all the TRITC images in a z-stack may be offset by a different fixed amount, etc.

In some embodiments, a microfilter membrane surface is first scanned using each of one or more channels (e.g., 4) at a magnification of 40×, taking multiple images sufficient to cover the entire microfilter surface. An entire filter surface scan may be performed at a lower magnification, such as 20×, to facilitate a high level analysis of the filter residue. In other embodiments, individual frames at a higher magnification, such as 60×, are taken of individual objects of interest, such as potential target cells, to facilitate analysis.

In some embodiments, after image capture, an extended depth of field stitching process is used, wherein the in-focus portion of each of the multiple images for each channel in a z-stack is used to stitch together an in-focus image of the complete field captured at that stage position. After the z-stack for each channel has been processed for extended depth of field, and a final single image for that channel at that stage position has been produced, the source images may be deleted. Individual images are then selected where objects for further study have been identified.

In some embodiments, an image of a metal microfilter is focused in brightfield mode using the light transmitted from the underside of the filter that passes through the pores of the microfilter. In some cases, this mode of focusing is repeatable and consistently focuses on the surface of the microfilter. If focusing is part of a fluorescence microscopy method, a suitable offset may be added to compensate for a difference between the optimal brightfield focus point and the optimal focus point for the emission wavelength of each fluorescent channel. In some cases, an additional offset is added to compensate for a difference between the filter surface and the midpoint of the height of a target cell above the filter surface. The use of a brightfield mode is enabled by the opaque property of the metal of the microfilter. Such use of brightfield mode differs from conventional fluorescence microscopy, where a fluorescence channel, such as a DAPI fluorescence channel, is primarily used for autofocusing. In some such cases, debris present on the microfilter which may have an affinity for an antibody and/or stain used in sample processing may be more intensely fluorescent than target cells of interest. The presence of these large, bright debris objects may cause the auto-focus algorithm to focus on them instead of the filter surface, causing the cells of interest to be out of focus. Therefore, use of the brightfield mode, optionally in combination with fluorescence focusing, may be specific for focusing on the surface of the metal microfilter instead of non-target cell debris.

In various embodiments, objects or cells of interest are potential target cells having an irregular DAPI+ nucleus between 7 and 17 um in its longest dimension and/or multiple DAPI+ nuclei. In some embodiments, the overall dimensions of a potential target cell is at least about 12-20 μm. Potential target cells are initially identified for further analysis manually or automatically by analyzing the DAPI channel images, and only selecting those images which contain a DAPI spot, as determined by thresholding, and spot selection by size parameters, e.g., diameter and area. Other parameters such as circularity, connectedness, etc. may also be used in the analysis.

Potential target cells identified in a large field capture are in some methods examined in detail using 40× or higher magnification images. In some embodiments, areas of interest comprising potential target cells are identified using the DAPI channel spot analysis technique. Other methods of identifying areas of interest may be used, for example by defining logical relationships between the presence of a DAPI spot on the DAPI channel and the presence of other biomarkers on other channels that are co-located or nearly co-located with the DAPI channel spot. These areas of interest may then be cropped and expanded to provide a larger, less cluttered sub-image image of the area of interest. This sub-image may comprise a composite image and separate channel sub-images of the area of interest. This sub-image may also contain identifying sample information, as well as other parametric information that may be useful to a pathologist examining the image. This information may also include a computerized estimate of the likelihood of a potential target cell in the area of interest being a CTC or TDMC. The estimate of likelihood may include data from the object in the area of interest, data from other objects from the current sample, and historical data from other samples. This historical data may come from samples processed by the local client, or samples processed by other clients and transmitted to the local client by the central server.

Images are analyzed, either manually and/or automatically by a computer software module. In some cases, potential target cells are given a probability of being a target cell. For example, a probability if the potential target cell is a tumor derived cell such as a CTC or TDMC. In some embodiments, depending on staining characteristics, size, morphology, and other characteristics of the tumor derived cell, each object of interest is also given a probability of being from a particular type of cancer. These probabilities may be 0%, 100%, or some value in between. An overall count of all tumor derived cells in a sample and their probabilities of being from a particular type of tumor is used to calculate a weighted TDMC/CTC type and count that can be used to produce a diagnosis of whether a patient has a particular type of cancer present, and if so, what type of tumor, and what stage the tumor is at.

Potential target cells identified by fluorescent microscopy having the following signature are in some embodiments given a probability greater than 0% as being a TDMC: DAPI+, a single irregular nucleus at least 16 μm across and/or have multiple DAPI+ nuclei; uptake of anti-EpCAM (e.g., TRITC positive); uptake of Cytokeratins 8, 18, and 19 (e.g., FITC positive); uptake of anti-CD45 (e.g., Cy5 positive); and any combination thereof. In some cases, the probability of a target cell being a TDMC is greater than 10%, 20%, 30%, 40%, 50%, 60%, 70%, 80%, or 90%. In some cases, the probability of a target cell being a TDMC is greater than 90%, 91%, 92%, 93%, 94%, 95%, 96%, 97%, 98%, 98%, 99%. In some cases, a TDMC is characterized by the signature and a cell of interest having that signature defines the cell of interest as being a TDMC. In some cases, a potential target cell is identified as a TDMC with a specificity of at least about 50%, 60%, 70%, 75%, 80%, 85%, 90%, 91%, 92%, 93%, 94%, 95%, 96%, 97%, 98%, 99% or 100%. In some cases, a potential target cell is identified as a TDMC with a selectivity of at least about 50%, 60%, 70%, 75%, 80%, 85%, 90%, 91%, 92%, 93%, 94%, 95%, 96%, 97%, 98%, 99% or 100%.

Computer Systems and Methods

In various aspects, provided herein are systems and methods for analyzing data generated from a microfilter. Methods for analysis of a microfilter enriched for a target cell include imaging the microfilter and analyzing characteristics of potential target cells captured on the microfilter. In some cases the analysis is performed by a clinician, computerized method, automated computational methods, or a combination thereof. In some embodiments, computer aided image recognition programs, in particular Convolutional Neural Networks (CNNs) in Deep Learning layered configurations are architected and trained to identify and classify a potential target cell as an actual target cell such as a TDMC, CTC. In some embodiments, the CNN has multiple image input channels, one for each fluorescence channel when the image is obtained using multichannel fluorescence microscopy. As an example, the CNN has four image input channels.

In some embodiments, Convolutional Neural Networks in Deep Learning configurations are used for image classification tasks. Implementation of CNNs is realized in software or hardware or both. Use of modern Graphics Processing Units (GPUs) with hundreds or thousands of individual processor cores capable of performing large numbers of matrix calculations in parallel. Further, the GPU based implementation makes it feasible to train large neural network models with millions of parameters. A supervised DNN comprises multiple layers for image recognition, where the layers are established based on CNNs, herein referred to as CNN/DNNs CNN/DNNs can be trained to identify TDMCs and CTCs. Furthermore, they can be trained to distinguish between TDMCs and CTCs by primary tumor type, and their output can be used to automatically generate total counts of TDMCs and CTCs.

CNN/DNN Architecture

The architecture of a Convolutional Neural Network (CNN) is designed to take advantage of the 2D structure of an input image (or other 2D input such as a speech signal). This is achieved based on local connections with weights followed by a form of pooling which results in more efficient detection of translation invariant features. A benefit of CNNs is that they are easier to train and have fewer parameters than fully connected networks with the same number of hidden units. Each convolutional layer of a CNN is a set of triplets of convolution, non-linear, and pooling layers that enable the model to learn, extract and enhance implicit features of an image. The triplet layer as a whole is called the convolutional layer. When stacked together, the first layers act like a feature filter such as an edge enhancer and allow the convolutional layer to extract local features which are passed to deeper convolutional layers which act like increasingly more global feature extractors. A CNN comprises one or more convolutional layers (often with a subsampling step). Further, the one or more convolutional layers are followed by one or more fully connected layers as in a standard multilayer neural network. It is called a "Deep" CNN because it has multiple hidden convolutional layers. Each convolutional layer contains a set of feature maps, or filters, that extract features from a region of units using a convolution. Then an additive bias is applied and the result is passed through a sigmoid function. In a CNN the convolution layers are applied on 2D feature maps to compute spatial features.

In the pooling layers, a region of the previous layer is connected to a unit in the current layer, reducing the dimension of the feature maps. In a type of pooling called max-polling, for each layer only the maximum value is passed. This enhances invariance to scale and distortions of the input. In some embodiments, the parameters of a CNN are learned either by a supervised approach and tuning the filters using a labeled training database, or an unsupervised approach. In some embodiments, methods for training a CNN for uses herein are performed using the supervised approach.

In some embodiments, the first convolutional layer is input with an m×m×r image where m is the height and width of the image and r is the number of channels, e.g., for four fluorescent channel grayscale images r=4. The convolutional layer will have k filters (or kernels) of size n×n×q where n is smaller than the dimension of the image and q can either be the same as the number of channels r or smaller and may vary for each kernel. The size of the filters gives rise to the locally connected structures which are each convolved with the image to produce k feature maps of size m−n+1. Each map is then subsampled typically with mean or max pooling over p×p contiguous regions where p is usually not more than 5 for larger inputs. Either before or after the subsampling layer an additive bias and sigmoidal nonlinearity is applied to each feature map. Multiple layers are needed because each layer operates at a higher level of abstraction, using the input from the previous layer as components to synthesize the next higher level of abstraction.

In some embodiments of the CNN/DNN architecture, the first convolutional layer filters the 224×224×4 input image with 96 kernels of size 11×11×4 with a stride of 4 pixels (this is the distance between the receptive field centers of neighboring neurons in the kernel map. Each kernel is a feature filter, being an 11×11 array with element values that enable it to detect specific features when convolved with the input data. A stride of 4 will result in a 55×55 pooling layer to follow the input convolutional layer in this example as 224/4=56.

Image Preprocessing

In some embodiments, each image captured by a microscope camera or other suitable acquisition device covers a field of approximately 360×360 microns at 40× magnification. TDMCs are typically no larger than approximately 20 microns across, but may be much larger, and therefore usually only occupy a small area in the overall image. To provide the CNN input layer with an appropriate image, each channel image of a potential TDMC and/or CTC is centered in a cropped sub-image wherein a cell of interest fills the a substantial portion of the sub-image.

In some embodiments, a sub-image is defined by algorithmic edge detection of cell boundaries and other processing. Sub-images may be defined by randomly selecting a sub-image crop of a pre-determined size, and determining if a whole cell boundary lies within the sub-image as follows. Each sub-image will be analyzed for closed regions based on a threshold level. The threshold level may be manually or preferably automatically determined. Additional threshold levels above and below the nominal threshold level may also be used, and the threshold level providing the best signal to noise ratio selected for additional processing. If a closed region is truncated by the edge of the image, another sub-image will be selected and checked for closed region truncation. This process will be repeated for each closed region until the closed region is fully within the borders of the frame. Closed region locations will be identified and their locations compared to closed regions in other frames. Duplicate images of closed regions will be discarded.

Alternatively, spot detection methods may be used as is well known in the art to identify cells and sub-image boundaries constructed around them.

Each sub-channel of each sub-mage may be individually processed to enhance brightness and contrast in order to maximize the range of the signal. Pixel noise may be removed by any de-noising process as is well known in the art. The images are typically captured in up to 16 bit grayscale, but are converted to 8 bit grayscale. After processing, the brightest non-noise pixel has a maximum value of approximately 225, and the darkest pixel has a value of approximately 25. This allows utilization of the bulk of the available dynamic range of the image without clipping. Each image is then expanded or reduced, depending on the input image resolution, to 224×224 pixels or other CNN input image size for presentation to the CNN input layer.

Figure 15:
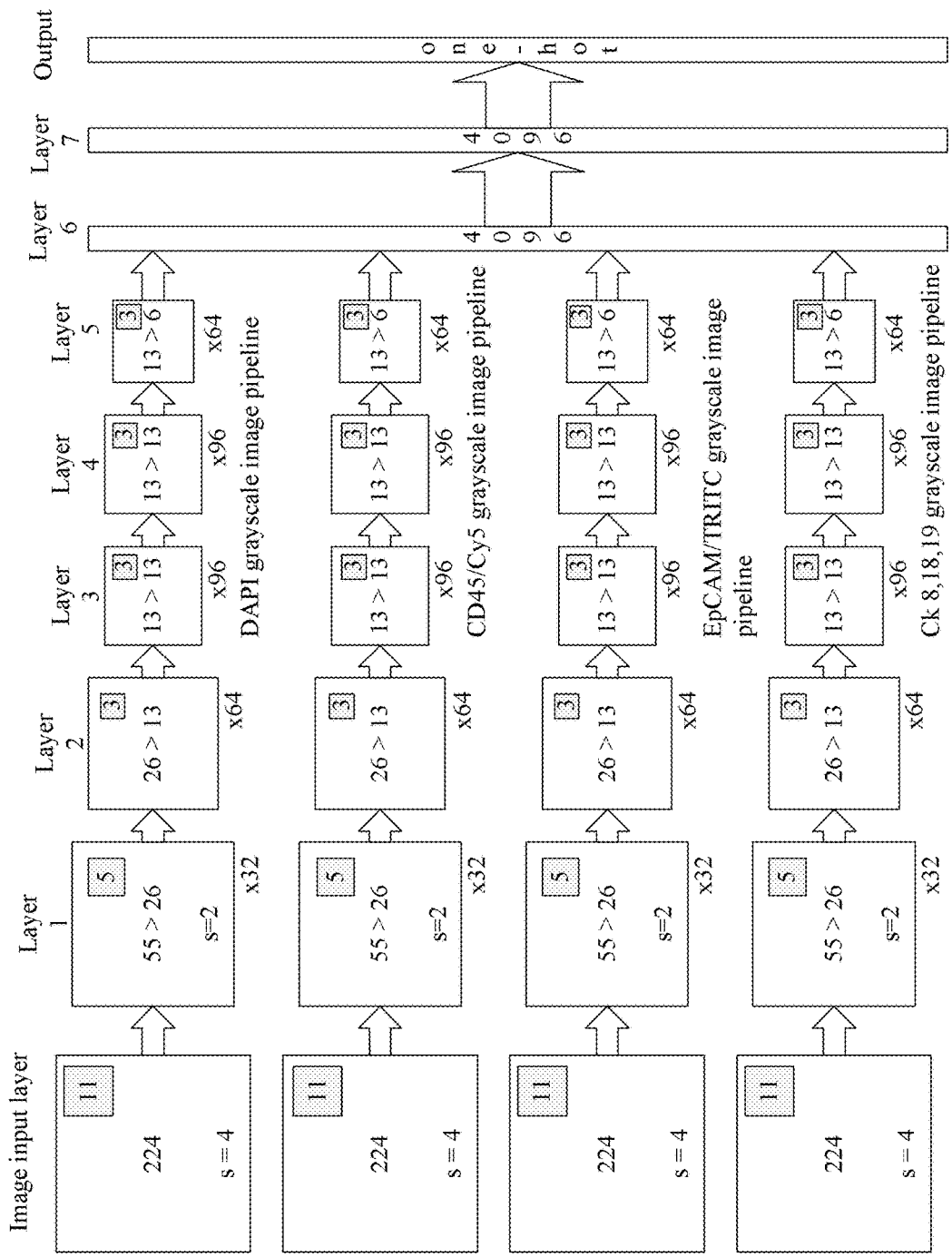
FIG. 15 is a diagram of the architecture of one embodiment of a Convolutional Neural Network/Deep Neural Network (CNN/DNN) for classifying CTCs and TDMCs.

FIG. 15 is a block diagram of one embodiment where the model includes five convolutional layers, each including a convolution, a rectified linear (ReLU) transform ($f(x)=\max(x; 0)$), and a max pooling transform (layers 1, 2, and 5). At the top of the architecture are three fully connected layers ("layer 6", "layer 7" and "layer 8" (the output)), which take as an input the output of the previous layer, multiply it by a matrix, and, in the case of layers 6, and 7 applies a rectified linear transform. The network is trained so that the layer 8 output corresponds to the one-hot encoding of the class label. The softmax loss is used during training. The class labels may be particular types of TDMCs and/or CTCs from a particular type of tumor, e.g., breast, ovarian, pancreatic, etc.

In the embodiment shown in FIG. 15, a 224×224 pixel crop of an input image is presented to the image input layer in the form of four 8 bit grayscale images, one image for each of the four fluorescent dies used in this embodiment. A filter, or "kernel" of size 11×11 is conjugated with each position in the image input, shifting by a step size of 4 after each conjugation. This results in an array of 55×55 values for each of the 32 filters used for each of the four grayscale input images. These 55×55 arrays are conjugated with a 5×5 kernel using a step size of 2 which produces a 26×26 array of max pool values, which are then presented as inputs to the next layer. This process is repeated, with the values shown in FIG. 15 for each layer through layer 5. The output of layer 5 is presented to fully connected layers 6 and 7, containing 4096 neurons each, and then to the fully connected one-hot output layer, which provides the classification signal.

The fluorophores shown in the embodiment of FIG. 15 are exemplary and the use of any fluorophore or detectable probe is envisioned. For example, any combination of the fluorophores described elsewhere herein or known in the art are used for classifying target cells using CNN/DNN.

CNN/DNN Training

After each of the one or more channel sub-images in the sub-frame has been individually processed, the sub-images can be used as a training input to the CNN/DNN. In some training methods, the sub-image frame set is labeled initially by a human operator for training. In some training methods, a minimum of approximately 500 image frames is labeled for each type of target cell and/or in the case of tumor derived cells, tumor type. Images can be rotated, reversed (mirror image), and translated to increase the size of the training set. In some embodiments, about 20% of the images are set aside for post-training testing, leaving about 80% of the images for training. In some embodiments about 75% of the training images are used for training input, and about 25% of the training images used for a validation set to be used during training. After training, accuracy is tested using the test set. Images can be flipped horizontally, vertically, and rotated to increase the size of the training image set.

When a training set has been used to train the CNN/DNN model to a satisfactory level of performance, it can be distributed from the central server to the client terminals so sample classification can be performed at the local client facility. In some cases this is performed because the file size of the images typically captured from a filter membrane can be on the order of 30 gigabytes (GB) and would take an excessive amount of time to transmit to a central facility for processing. Alternatively, only the images containing objects of interest could be uploaded to the central server and a web-based image analysis CNN/DNN method may be used. In any case, images of objects of interest from patient samples processed at client facilities can be uploaded to the central server for purposes of continually increasing the size of the training set and allowing periodic retraining of the CNN/DNN model.

Also, multiple CNN/DNN models may be used simultaneously in an ensemble, and a fully connected layer may be trained to use the outputs of all CNN/DNNs in the ensemble to produce an output classification with a higher level of performance than any individual CNN/DNN in the ensemble.

CNN/DNN TDMC Classification

In some embodiments, after successful testing, a CNN/DNN is used to analyze new images, such as those acquired during fluorescence microscopy of an enriched microfilter. The CNN/DNN will provide a classification for each frame image (one or multiple channel images) applied to the input.

In some embodiments, a computer counts the number of positive classifications the CNN/DNN makes. If the CNN/DNN has been trained on multiple tumor types, the computer keeps a count for each tumor type. The computer will also keep a count of the types of tumor classifications made by the CNN/DNN.

In some embodiments, ensembles of CNN/DNN classifier networks are used. The average of classification output values can be used, or the strongest output classification value can be used to determine the final classification of a TDMC identified in an input image.

In some embodiments, some target cells such as TDMCs are occluded by other cells or debris. The CNN/DNN can be trained with occluded images as inputs, which will enable it to recognize partially occluded target cell images as TDMCs.

In some embodiments, a microscopy communicates with a computing device (e.g., a server, a personal computer, a tablet, a laptop, a laptop, a smartphone, etc), wherein image datasets are acquired and stored in the computing device. The computing device is local or remote to the microscopy. In some embodiments, classification is performed on the computing device. In some embodiments, classification is performed on a remote computing device. For example, a server is used to host datasets imaged by a microscopy, and a tablet is used by a remote user to remotely access the server to perform classification on the images.

In some embodiments, a microscopy communicates with a computing device with a database service. In further embodiments, images collected by a microscopy are stored in a single database, or in a plurality of databases. In some cases, images in databases are processed sequentially or in parallel.

Network

In various embodiments, any system or component thereof described herein comprises and/or is operably connected to a computer network. In some instances, the computer network comprises one or more computers operably connected to an image acquisition device such as a microscope camera, wherein operably connected may be wireless or physical. In many implementations, the computer network comprises a plurality of computers and/or devices which are connected by physical or wireless means. A computer of the network may be located remotely from the acquisition device. In some instances, the computer network comprises one or more acquisition computers for controlling the acquisition of an image of a sample such a microfilter. In exemplary embodiments, the computer network is configured to control the acquisition, processing and/or display of an image of a sample such as a microfilter, wherein the image may be saved and/or live. In some instances, the network comprises one or more displays for viewing an acquired image, either saved, live or both. In some embodiments, one or more of the displays is a component of a viewing terminal of the network. A viewing terminal may be located remotely from the acquisition device. A computer, in various implementations, comprises software. In some embodiments, the computer network comprises the internet. In some embodiments, the computer network comprises a web browser.

Figure 16:
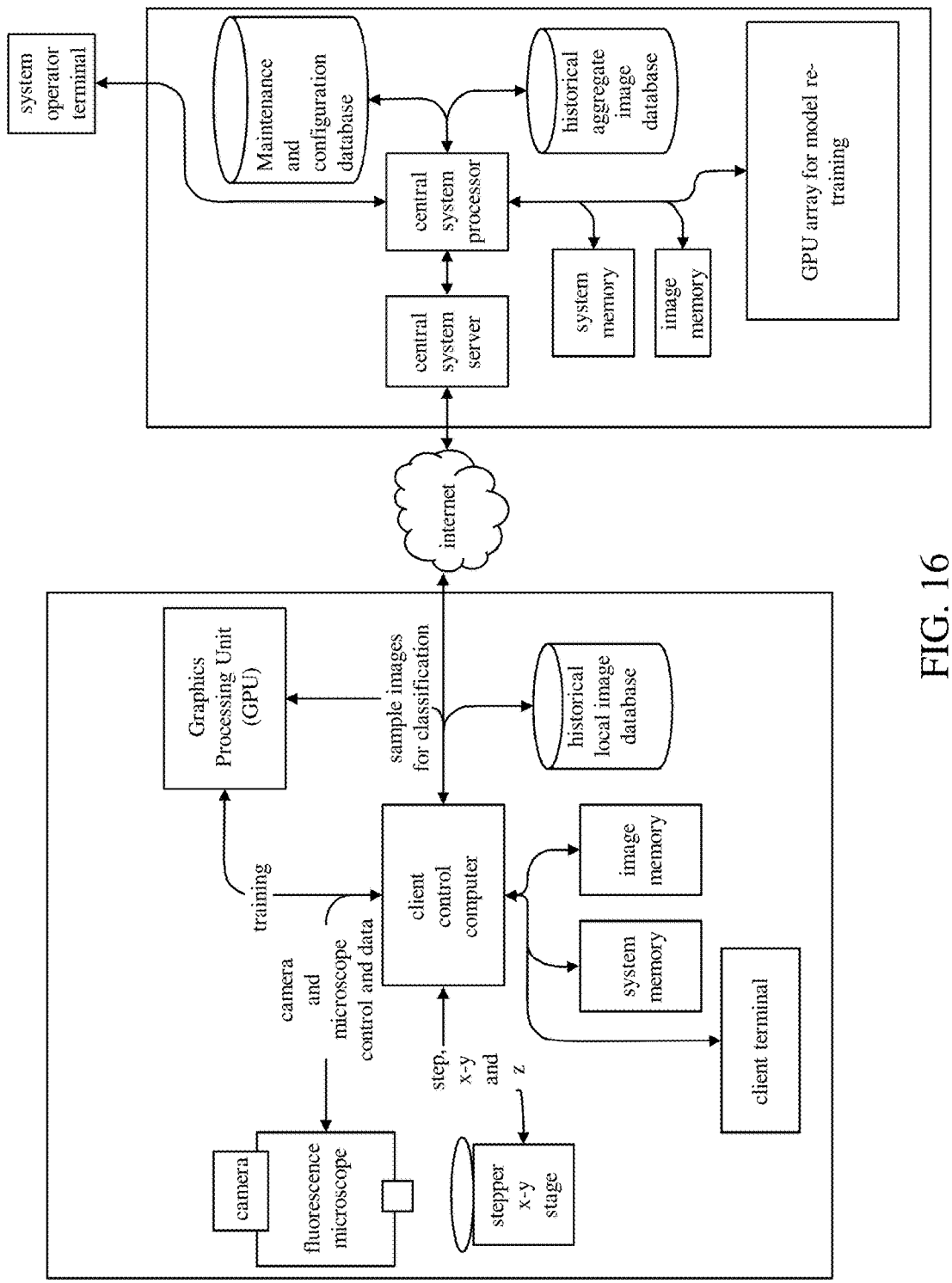
FIG. 16 is a system diagram showing one client system and one central server system.

Multiple client location terminals may perform any of the methods described herein. FIG. 16 shows how the client terminals are connected to a central system server. The central system server manages operations and distributes and updates the convolutional neural network model software used at the terminals. The central system server will receive and store image, patient status, and test result data from the client terminals. Image data from all clients can be used to continually re-train a convolutional neural network model at the server. Improvements to the model may result in an updated convolutional neural network model being distributed to the client terminals. In this way, all data available to the system as a whole can be used to optimize the deep learning convolutional neural network image analysis model.

In some embodiments, a computing system comprises one or more client systems and a server. Each client system is connected via the internet to the server. In some embodiments, any images of interest and their classification findings are transmitted to the server by the client system. At least some of the most interesting images are uploaded, even from normal patients. An image can include a target cell indicative of a cancer, or a target cell indicative of a normal condition. In some applications, only images with cancer target cells are uploaded; in some cases, only images with normal conditions are uploaded; in certain cases, both types of images are uploaded. In some embodiments, the server has a multiple-core GPU, or a very powerful CNN training hardware configuration. Pathologists review each received images, and the images are also attempted to be classified by the server CNN model, which at any given time is more advanced than the current FDA approved model rev which is out in the field at the clients (because it has seen more data since the last rev was released). Follow-up information is maintained on patients, and if their condition changes, that information is used to refine the classification capability of the central model. For example, if a patient goes from normal to stage I, (No TDMCs to a few) at a subsequent blood test, the previous images can start to form a new classification, e.g., "previously normal patient now having a positive diagnosis".

When the central model is sufficiently improved, it can be distributed as the next rev to the client system, after having received FDA approval, if necessary.

Database

In various aspects, any system components described herein comprise and/or are operably connected to a database. In some cases, the database is stored in a storage device. In some embodiments, the storage device is a removable component, for example, a universal serial bus (USB) drive or compact disk. In other or additional embodiments, the database is stored a cloud-based storage system.

In some embodiments, in order to provide a basis for the analysis of a potential target cell as an actual target cell, a reference database is established. The reference database contains a number of reference profiles from samples comprising a disease or not comprising a disease, with various types and stages of diseases optionally included. In some embodiments, a signature of a cell of interest is compared to a reference database containing the reference profiles. In some cases, if the signature of the cell of interest matches best with the signature of a particular cell type in the database, the subject is diagnosed as having that cell type. Various computer systems and software can be utilized for implementing the analytical methods of this disclosure and are apparent to one of skill in the art. In some embodiments, a score or probability that a cell of interest is a target cell is calculated by comparison to a reference database.

In view of the disclosure provided herein, those of skill in the art will recognize that many databases are suitable for the methods and systems describe herein. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Software

In some embodiments, provided herein is software for image recognition executable on a computer described herein. In some cases, the computer is a portable computer such as a laptop, tablet, phone, and the like. In some embodiments, a software program controls the acquisition of one or more images of a sample. In some embodiments, a software program analyzes an image of a sample, such as by using CNN as described elsewhere herein. In some embodiments, a software program is provided on a plurality of computers and/or devices of the system. In some embodiments, a software program is provided on a web browser of the system.

In some embodiments, a software program is useful for controlling the operation of an image acquisition device and/or microscope. This includes, without limitation, the acquisition of an image of a microfilter and/or the manipulation of a view of the microfilter. Manipulation of an image view includes, without limitation, focusing a view of a microfilter (e.g., by changing the position of an objective lens relative to the sample), changing the magnification (e.g., by changing an objective lens), and zooming and/or panning around a saved or live image. In some embodiments, software is used to control the position of a slide holder, in most cases to change the sample field of view. In some embodiments, software is used to change an objective lens of an image acquisition device to a different objective lens. In some embodiments, software is used to move the position of an objective lens relative to a microfilter to provide automatic or user controlled image focusing. In some embodiments, software automatically detects a region of a slide comprising the microfilter, and acquires one or more images so that image(s) of the entire microfilter is acquired.

Digital Processing Device

In some embodiments, methods, systems, media, and devices described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3@, Sony® PS4@, Microsoft® Xbox 360®, Microsoft Xbox One, Nintendo® WHO, Nintendo® Wii U®, and Ouya®.

In some embodiments, the digital processing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Non-Transitory Computer Readable Storage Medium

In some embodiments, methods, systems, media, and devices disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, methods, systems, media, and devices disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™ Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, methods, systems, media, and devices disclosed herein include software, server, and/or database modules, or use of the same. In some embodiments, a software module performs one or more operations of image analysis using CNN as described elsewhere herein. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Applications of the Methods

In various aspects, provided herein are methods for the detection of a disease and/or characteristic of a disease in a subject by comparing a signature of a cell of interest from the subject with a signature of a target cell indicative of the disease. In some embodiments, the disease is cancer and a target cell is a tumor derived cell. In some embodiments, tumor derived cells are detected by analyzing a signature of enriched cells of interest from a sample of the subject. As a non-limiting example, if a cell of interest comprises a signature of a tumor derived cell, the patient is diagnosed as having cancer. In some embodiments, a signature includes cell morphology and/or the presence or absence of one or more tumor biomarkers in a cell of interest. In some cases, detecting a cell of interest comprises identifying the presence or absence of a cell with a large, irregular nucleus or multiple nuclei characteristic of a tumor derived cell. For example, by using a fluorescent stain that localizes to the nucleus, such as DAPI. In some cases, identifying a cell of interest as a target cell comprises identifying a biomolecule bound to the cell of interest, and/or identifying a binding event between a biomolecule and the cell of interest, wherein the biomolecule is specific for a biomarker of the target cell. A biomolecule configured to bind or otherwise interact with a biomarker of a target cell, such as a protein expressed on a tumor derived cell, is a probe.

In various methods provided herein, a biological sample is enriched for tumor derived cells, and the enriched sample is treated with one or more probes specific for a biomarker or feature of tumor derived cells. In some methods, a biological sample is combined with the one or more probes and then enriched for tumor derived cells. Non-limiting examples of probes include: a biomolecule that binds to CD45, a biomolecule that binds to EpCAM, a biomolecule that binds to Ck8, a biomolecule that binds to Ck18, a biomolecule that binds to Ck19, and a biomolecule that binds to a specific marker characteristic of a type of tumor. Non-limiting examples of markers characteristic of tumor type include PSMA, AFP, CEA, CA-125, MUC-1, ETA, tyrosinase, MAGE, VEGF, Her2nue, B2M, c-kit/CD117, ER, PR, fibrin and fibrinogen. Biomolecules include small molecules, peptides and proteins such as antibodies. An antibody includes an entire immunoglobulin molecule or any polypeptide comprising fragment of an immunoglobulin including, but not limited to: heavy chain, light chain, variable domain of a heavy chain, variable domain of a light chain, constant domain of a heavy chain, constant domain of a light chain, complementarity determining region (CDR), framework region, fragment antigen binding (Fab) region, Fab', F(ab')2, F(ab')3, fragment crystallizable (Fc) region, single chain variable fragment (scFV), di-scFv, single domain immunoglobulin, trifunctional immunoglobulin, chemically linked F(ab')2, and any portion or combination thereof.

In some embodiments, a probe binds to nucleic acids and thus is localized to the nucleus of a cell. In some cases, a probe is a fluorescent probe. Non-limiting examples of probes include: DAPI; and anti-CD45, anti-EpCAM antibody, anti-Ck8 antibody, anti-Ck18 antibody, anti-Ck19 antibody, and conjugates thereof, e.g., conjugates comprising a fluorophore. Detection methods provided herein may occur in tandem or successively. For example, detection comprises identifying the presence of a tumor derived cell and then identifying the type of tumor from which the cell was derived.

In some embodiments, a method for diagnosis cancer in a subject comprises passing a biological sample from the subject through a microfilter comprising a membrane and a plurality of pores extending through the membrane; wherein a diameter of one or more of the plurality pores is smaller than a length of a target cell; and wherein if the biological sample comprises the target cell, retaining the target cell on a surface of the membrane; applying to the microfilter a probe comprising a ligand specific for a biomarker of the target cell; wherein if the target cell is retained on the surface of the membrane, binding the probe to the target cell; and detecting the presence or absence of the target cell by detecting the presence or absence of the probe bound to the target cell; wherein the presence of the target cell is indicative of cancer in the subject. In some cases, the target cell is a TDMC, CTC and/or TAM. In some methods, a biomarker is cytokeratin 8, cytokeratin 18, cytokeratin 19, EpCAM, or a combination thereof. In some embodiments, the method comprises applying to the microfilter a probe that binds to a nucleic acid and/or localizes to the nucleus of a cell, for example, DAPI. In some methods the cancer is breast cancer. In some methods the cancer is ovarian cancer. The cancer may be any cancer as described elsewhere herein or known in the art. In some methods, the specificity for diagnosing cancer in the subject is greater than about 50%, 60%, 70%, 80%, 90% or greater. In some methods, the selectivity for diagnosing cancer in the subject is greater than about 50%, 60%, 70%, 80%, 90% or greater.

In some embodiments, the biological sample is whole blood, serum or plasma. In some embodiments, the biological sample is passed through the microfilter at a rate of between 1 and 15 milliliters per minute. In some embodiments, a biological sample has a volume between about 1 and about 15 milliliters, for example about 7.5 milliliters.

In some embodiments, the membrane comprises a metal. In some such cases, the membrane has an autofluorescence less than parylene-C filter material in the FITC, TRITC, and Cy5 fluorescent channels used in fluorescence microscopy, by relative measurement. In some embodiments, the membrane has an autofluorescence that is less than about 80%, 70%, 60%, 50%, 40%, 30%, 20%, 10%, or 5% of the autofluorescence of parylene-C in the FITC, TRITC, and/or Cy5 fluorescent channels, by relative measurement. In some cases, the membrane has an autofluorescence less than about 20% of the autofluorescence of parylene-C in the FITC channel. In some cases, the membrane has an autofluorescence less than about 20% of the autofluorescence of parylene-C in the TRITC channel. In some cases, the membrane has an autofluorescence less than about 50% of the autofluorescence of parylene-C in the Cy5 channel In some cases, the membrane has low autofluorescence from excitation wavelengths of about 330 nm to about 650 nm, when auto fluorescing in emission wavelengths of about 400 nm to about 800 nm. In some cases, the metal comprises nickel, gold, cobalt, chromium, copper, iron, manganese, platinum, zinc, palladium, titanium, silver, molybdenum, tungsten, aluminum, indium, carbon, silicon, tin, lead, or an alloy or combination thereof. As a non-limiting example, the metal comprises nickel, palladium or a combination thereof. In some cases, the microfilter withstands a pressure of at least about 10 mm Hg to 760 mm Hg. In some cases, the tensile strength of the membrane or a material thereof (e.g., metal) is greater than about 75, 100, 150, 200, 300, 400, or 500 MPa. As a non-limiting example, the membrane comprises a metal having a tensile strength between about 200 and 800 MPa, between about 200 and 600 MPa, between about 300 and 500 MPa, or any value there between.

In some embodiments, the diameter of one or more of the plurality of pores is between about 1 and about 50 microns, for example, about 5, 6, 7, 8, 9, 10, 15, 20, 30, 40 or 50 microns. In some embodiments, the height of the microfilter is between about 5 and about 1,000 microns. Non-limiting microfilter heights include about 5, 6, 7, 8, 9, 10, 11, 12, 13, 14, 15, 16, 17, 18, 19, 20, 50, 100, 200, 300, 400, 500, 600, 700, 800, 900 and 1,000 microns, as well as any range therein, such as 5-15, and 50-500 microns. In some embodiments, the aspect-ratio of each of the plurality of pores is less than about 5, 4, 3, 2 or 1. In other embodiments, the aspect-ratio of each of the plurality of pores is greater than about 5, 10, 15 or 20. In some embodiments, the diameter or length along an axis of the microfilter is between about 1 and about 30 millimeters. Non-limiting examples of microfilter diameters and lengths include about 1, 2, 3, 4, 5, 6, 7, 8, 9, 10, 11, 12, 13, 14, 15, 16, 17, 18, 19, 20, 21, 22, 23, 24, 25, 26, 27, 28, 29 and 30 millimeters, as well as any range therein, such as 1-20, 6-18, 7-16, 8-15, and 9-14. In some embodiments, the filter surface area of the microfilter is between about 20 mm$^2$ and 1,000 mm$^2$, between about 20 mm$^2$ and 300 mm$^2$, or between about 40 mm$^2$ and 80 mm$^2$. In some embodiments, a first pore of the plurality of pores is separated from a second pore of the plurality of pores by a distance of about 1 to about 24 microns. In some embodiments, the density of the plurality of pores per square millimeter is between about 1 and about 10,000 pores, between about 1 and 3,000 pores, less than about 1 pore, or greater than about 3,000 pores.

In some embodiments, the microfilter is patterned so that a central region of the microfilter comprises a plurality of pores (referred to as a membrane) and surrounding this central region is an annular support ring optionally not comprising a pore. The annular support ring is not limited in shape to a ring and includes any shape suitable for surround one or more sides or the entire central region. In some such cases, the width of the annular supporting ring is between about 0.5 and about 20 millimeters. For example, the annular supporting ring is about 1, 2, 3, 4, 5, 10, 15 or 20 millimeters in width. In some cases, the diameter or length along an axis of the central region is between about 5 and about 30 millimeters. For example, the diameter or length of the central region is about 5, 6, 7, 8, 9, 15, 20, 25 or 30 millimeters.

In some embodiments, the target cell is captured on the surface of the membrane by a biomolecule or chemical moiety that binds to or otherwise attracts the target cell. In some cases, the biomolecule is a protein such as a cytokine or other antigen. In some cases, the biomolecule is an antibody. In some cases, the biomolecule is specific for a type of target cell, for example, if the target cell is tumor derived, the biomolecule is specific for the tumor.

Detection methods include detecting the presence or absence of the probe bound to a potential target cell by measuring or detecting an electric signal, a chemiluminescent signal, a fluorescent signal, or other detection methods known in the art. In some methods, the detection is by fluorescence microscopy and the probe comprises a fluorophore. In some cases, detecting the presence or absence of the probe bound to the potential target cell comprises detecting a fluorescent signal from the fluorophore. In some embodiments, a software module configured to detect fluorescence detects the presence or absence of the fluorescent signal.

In some embodiments, a cell captured on a microfilter is identified as a tumor derived cell by visually assessing one or more images of the microfilter for a tumor derived cell signature in the captured cell. In some cases, the captured cell is a potential target cell or cell of interest that is identified using multi-channel fluorescence microscopy. In some microscopy methods, the entire microfilter surface is viewed/imaged at a magnification of approximately 40×, where potential target cell-like objects are identified using size, morphology, and response to stains and antibodies. Images of an individual cell of interest may be cropped so as to fully include the cell image along with sufficient background to frame the cell, and a thumbnail array consisting typically of images of the one or more fluorescence channels (depending on the number and type of fluorophores) and a composite. In some cases, the number of images is 5, corresponding to four images from four fluorescence channels and one composite image. In some cases, because tumor derived cells such as TDMCs are heterogeneous, they may require visual inspection by a trained clinician to verify that a cell of interest is indeed a TDMC. This method is sufficient for low to medium volume testing, but may become prohibitively expensive for larger testing programs. Therefore, some methods provide for computer aided image recognition programs, in particular Convolutional Neural Networks (CNNs) in Deep Learning layered configurations can be architected and trained to identify and classify TDMCs and CTCs. In one embodiment, the CNN may have four image input channels, one for each fluorescence channel.

In some methods, detecting the presence or absence of a target cell comprises a computer-implemented method comprising: (a) transmitting, by a computer, a surface scanning instruction to a multichannel fluorescence acquisition device, wherein the microfilter is positioned on a stage of the multichannel fluorescence acquisition device; the surface scanning instruction comprising one or more commands for the multichannel fluorescence acquisition device to determine the z-axis height of the microfilter surface; (b) transmitting, by a computer, an image capture instruction to the multichannel fluorescence acquisition device, the image capture instruction comprising one or more commands for the multichannel fluorescence acquisition device to acquire a plurality of digital images of the microfilter using a channel corresponding to the fluorophore, wherein the plurality of digital images are acquired at each stage position in a z-stack having a focus plan centered on the microfilter surface height determined in step (a); (c) generating, by a computer, an in-focus image by stitching together in-focus portions of each of multiple images of the plurality of digital images; (d) selecting, by a computer, an in-focus image that comprises a cell of interest; and (e) identifying, by a computer, an area of interest comprising the cell of interest in the in-focus image. In some embodiments, the method comprises determining, by a user, a probability of the cell of interest being the target cell. In some embodiments, the method comprises determining, by a user, a probability of the cell of interest being from a particular type of cancer. In some embodiments, the method comprises applying to the microfilter one or more additional probes each comprising an additional fluorophore; wherein the computer implemented method further comprises transmitting a scanning instruction comprising one or more commands for the digital acquisition device to acquire a digital image of the microfilter using one or more additional fluorescent channels corresponding to the one or more additional fluorophores.

In some embodiments, an in-focus image of a metal microfilter surface is generated in brightfield mode using the light transmitted from the underside of the filter that passes through the pores of the microfilter. In some cases, this mode of focusing is repeatable and consistently focuses on the surface of the microfilter. If focusing is part of a fluorescence microscopy method, a suitable offset may be added to compensate for a difference between the optimal brightfield focus point and the optimal focus point for the emission wavelength of each fluorescent channel. In some cases, an additional offset is added to compensate for a difference between the filter surface and the midpoint of the height of a target cell above the filter surface. The use of a brightfield mode is enabled by the opaque property of the metal of the microfilter.

Some computer-implemented methods comprise enhancing, by a computer, the visibility of a feature in the acquired digital image.

In some embodiments, detecting the presence or absence of the target cell comprises a computer-implemented method comprising: (a) transmitting, by a computer, an image capture instruction to a multichannel fluorescence acquisition device, wherein the microfilter is positioned on a stage of the multichannel fluorescence acquisition device; the image capture instruction comprising one or more commands for the multichannel acquisition device to acquire one or more digital images of the microfilter using a channel corresponding to a fluorophore of the probe; (b) receiving, by a computer, the one or more digital images of the microfilter; and (c) determining, by a computer, the presence or absence of the target cell in each of the one or more digital images of the microfilter. In some cases, the computer determines the presence or absence of the target cell using a software module configured with a trained convolutional neural network (CNN).

In some embodiments, a cell of interest is analyzed for a signature that is similar to the signature of a tumor derived cell. For example, a cell of interest captured using a microfilter described herein has one or more features and/or signatures of a TDMC: large irregular nucleus and/or multiple nuclei, CD45+, and/or binds to anti-EPCAM and/or anti-Ck 8, 18, and 19 antibodies. In some such cases, a cell of interest is determined to be a tumor derived cell and the patient from which the tumor was derived is diagnosed as having cancer. In some cases, the diagnosis is a probability. For example, the probability is anywhere between 0% and 100%. In some cases, the patient is diagnosed with having cancer with a specificity of at least about 50%, 60%, 70%, 80%, 90%, 91%, 92%, 93%, 94%, 95%, 96%, 97%, 98%, 99% or about 100%. In some cases, the patient is diagnosed with having cancer with a selectivity of at least about 50%, 60%, 70%, 80%, 90%, 91%, 92%, 93%, 94%, 95%, 96%, 97%, 98%, 99% or about 100%.

In some embodiments, the number and/or signature of a cell of interest identified as a tumor derived cell is indicative of a stage of cancer. In some cases, the tumor derived cell is a TDMC isolated and/or detected using any method and/or device described herein. In some embodiments, the degree of intensity from a fluorescent signal in a fluorescence microscopy detection method indicates a stage of cancer. In some cases, the stage of cancer in a patient is diagnosed with a specificity of at least about 50%, 60%, 70%, 80%, 90%, 91%, 92%, 93%, 94%, 95%, 96%, 97%, 98%, 99% or about 100%. In some cases, the stage of cancer in a patient is diagnosed with having cancer with a selectivity of at least about 50%, 60%, 70%, 80%, 90%, 91%, 92%, 93%, 94%, 95%, 96%, 97%, 98%, 99% or about 100%. In some cases, a patient with early stage cancer (e.g., stage 0 or 1) is diagnosed with a specificity of at least about 50%, 60%, 70%, 80%, 90%, 91%, 92%, 93%, 94%, 95%, 96%, 97%, 98%, 99% or about 100%. In some cases, a patient with early stage cancer (e.g., stage 0 or 1) is diagnosed with a selectivity of at least about 50%, 60%, 70%, 80%, 90%, 91%, 92%, 93%, 94%, 95%, 96%, 97%, 98%, 99% or about 100%. In some cases, a patient with middle stage cancer (e.g., stage 2) is diagnosed with a specificity of at least about 50%, 60%, 70%, 80%, 90%, 91%, 92%, 93%, 94%, 95%, 96%, 97%, 98%, 99% or about 100%. In some cases, a patient with middle stage cancer (e.g., stage 2) is diagnosed with a selectivity of at least about 50%, 60%, 70%, 80%, 90%, 91%, 92%, 93%, 94%, 95%, 96%, 97%, 98%, 99% or about 100%. In some cases, a patient with an advanced stage of cancer (e.g., stage 3 or 4) is diagnosed with a specificity of at least about 50%, 60%, 70%, 80%, 90%, 91%, 92%, 93%, 94%, 95%, 96%, 97%, 98%, 99% or about 100%. In some cases, a patient with an advanced stage of cancer (e.g., stage 3 or 4) is diagnosed with a selectivity of at least about 50%, 60%, 70%, 80%, 90%, 91%, 92%, 93%, 94%, 95%, 96%, 97%, 98%, 99% or about 100%.

In some embodiments, the number and/or signature of a cell of interest identified as a tumor derived cell is indicative of a type of cancer. In some cases, the tumor derived cell is a TDMC isolated and/or detected using any method and/or device described herein. In some embodiments, the degree of intensity from a fluorescent signal in a fluorescence microscopy detection method indicates a type of cancer. In some cases, the type of cancer in a patient is diagnosed with a specificity of at least about 50%, 60%, 70%, 80%, 90%, 91%, 92%, 93%, 94%, 95%, 96%, 97%, 98%, 99% or about 100%. In some cases, the type of cancer in a patient is diagnosed with having cancer with a selectivity of at least about 50%, 60%, 70%, 80%, 90%, 91%, 92%, 93%, 94%, 95%, 96%, 97%, 98%, 99% or about 100%. The cancer may be any cancer described herein, including breast and ovarian cancers. In some embodiments, the signature of a TDMC from one type of cancer is different from another type of cancer, e.g., the TDMCs are morphologically distinct and/or respond differently to stains and reagents. For example, in some embodiments ovarian cancer has less takeup of antibodies to EpCAM, Ck 8,18,19 and CD45 than breast cancer. As a result, TDMC morphology and staining response can be used to distinguish between different types of tumor. CNN/DNN networks can learn to make these distinctions by training on known samples.

In some embodiments, following identification of a tumor derived cell in a biological sample from a patient, Fluorescence In Situ Hybridization (FISH) testing is performed on the isolated tumor derived cells to identify gene abnormalities associated with particular types of cancer. Similarly, single cell RNA sequencing can be used to detect the presence of RNA sequences known to be associated with particular types of cancer.

In some embodiments, the number and/or signature of a cell of interest identified as a tumor derived cell in a sample of a patient taken at a first time point is compared to the number and/or signature of a cell of interest identified as a tumor derived cell in a second sample of the patient taken at a second time point. In some cases, the tumor derived cell is a TDMC isolated and/or detected using any method and/or device described herein. In some cases, monitoring tumor derived cell number and/or signature indicates the progression of cancer. In some cases, monitoring tumor derived cell number and/or signature indicates success and/or failure of treatment. In some cases, monitoring tumor derived cell number and/or signature is indicative of remission. For example, if a tumor derived cell is detected in the first time point and not the second time point. Likewise, in some cases, monitoring the signature is indicative of recurrence. For example, if a tumor derived cell is detected in the first time, not detected in the second time point, and detected in a third time point. In some embodiments, the degree of intensity from a fluorescent signal from a tumor derived cell in a fluorescence microscopy detection method between two different samples from a patient taken at two different time points provides an indication of prognosis, treatment efficacy, remission and/or recurrence. In some cases, the prognosis of cancer in a patient is identified with a specificity of at least about 50%, 60%, 70%, 80%, 90%, 91%, 92%, 93%, 94%, 95%, 96%, 97%, 98%, 99% or about 100%. In some cases, the prognosis of cancer in a patient is diagnosed with having cancer with a selectivity of at least about 50%, 60%, 70%, 80%, 90%, 91%, 92%, 93%, 94%, 95%, 96%, 97%, 98%, 99% or about 100%. In some cases, remission in a patient is identified with a specificity of at least about 50%, 60%, 70%, 80%, 90%, 91%, 92%, 93%, 94%, 95%, 96%, 97%, 98%, 99% or about 100%. In some cases, remission of cancer in a patient is diagnosed with having cancer with a selectivity of at least about 50%, 60%, 70%, 80%, 90%, 91%, 92%, 93%, 94%, 95%, 96%, 97%, 98%, 99% or about 100%. In some cases, recurrence of cancer in a patient is identified with a specificity of at least about 50%, 60%, 70%, 80%, 90%, 91%, 92%, 93%, 94%, 95%, 96%, 97%, 98%, 99% or about 100%. In some cases, recurrence of cancer in a patient is diagnosed with having cancer with a selectivity of at least about 50%, 60%, 70%, 80%, 90%, 91%, 92%, 93%, 94%, 95%, 96%, 97%, 98%, 99% or about 100%.

Time points for the monitoring cell signatures from a patient provided herein include any interval of time. In some embodiments, the time points are 1 day, 2 days, 3 days, 4 days, 5 days 6 days, 1 week, 2 weeks, 3, weeks, 4 weeks, 1 month, 2 months, 3 months, 4 months, 5 months, 6 months, 7 months, 8 months, 9 months, 10 months, 11 months, 1 year, 2 years or longer apart.

In some embodiments, the number and/or signature of a cell of interest identified as a tumor derived cell is determined to confirm or validate a cancer diagnosis method performed using a different method. In some cases, the tumor derived cell is a TDMC isolated and/or detected using any method and/or device described herein. For example, after a patient suspected of having lung cancer has received an indeterminate screening result from a Low Dose Computerized Tomography (LDCT) test, which occurs in 25% of LDCT lung cancer screening tests, additional procedures such as needle or surgical biopsy are required. But 96% of all LDCT indeterminate results turn out to be benign, so 96% of these follow-on procedures are unnecessary. A test for the presence of TDMCs in the patient's blood, as described herein, is a promising alternative to a biopsy to confirm or negate the LDCT result. In some cases, a cancer diagnosis is validated with a specificity of at least about 50%, 60%, 70%, 80%, 90%, 91%, 92%, 93%, 94%, 95%, 96%, 97%, 98%, 99% or about 100%. In some cases, a cancer diagnosis is validated with a selectivity of at least about 50%, 60%, 70%, 80%, 90%, 91%, 92%, 93%, 94%, 95%, 96%, 97%, 98%, 99% or about 100%.

In some embodiments, cancer refers to an abnormal growth of cells that proliferate in an uncontrolled way and, in some cases, metastasize. Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer)) and hematological tumors (such as the leukemias and lymphomas) at any stage of the disease, with or without metastases.

In some embodiments, the cancer is a solid tumor. In some embodiments, the cancer is bladder cancer, colon cancer, brain cancer, breast cancer, endometrial cancer, heart cancer, kidney cancer, lung cancer, liver cancer, uterine cancer, blood and lymphatic cancer, ovarian cancer, pancreatic cancer, prostate cancer, thyroid cancer, or skin cancer. In some embodiments, the cancer is a sarcoma, carcinoma, or lymphoma. In some instances, the cancer is metastatic melanoma. In some instances, the cancer is non-small cell lung cancer. In some instances, the cancer is renal-cell cancer. In some instances, the cancer is prostate cancer. In some instances, the cancer is colorectal cancer. In some instances, the cancer is pancreatic cancer. In some instances, the cancer is cervical cancer. In some instances, the cancer is gastric cancer. In some instances, the cancer is ovarian cancer. In some instances, the cancer is breast cancer.

Additional non-limiting examples of cancers include acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, desmoid tumors, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, microfilter, microfiltration method, and/or diagnosis method described herein is used to diagnosis, characterize, stage, and/or monitor breast cancer.

In some embodiments, microfilter, microfiltration method, and/or diagnosis method described herein is used to diagnosis, characterize, stage, and/or monitor ovarian cancer.

In some embodiments, microfilter, microfiltration method, and/or diagnosis method described herein is used to diagnosis, characterize, stage, and/or monitor oral cancer, prostate cancer, rectal cancer, non-small cell lung cancer, lip and oral cavity cancer, liver cancer, lung cancer, anal cancer, kidney cancer, vulvar cancer, breast cancer, oropharyngeal cancer, nasal cavity and paranasal sinus cancer, nasopharyngeal cancer, urethra cancer, small intestine cancer, bile duct cancer, bladder cancer, ovarian cancer, laryngeal cancer, hypopharyngeal cancer, gallbladder cancer, colon cancer, colorectal cancer, head and neck cancer, parathyroid cancer, penile cancer, vaginal cancer, thyroid cancer, pancreatic cancer, esophageal cancer, Hodgkin's lymphoma, leukemia-related disorders, mycosis fungoides, or myelodysplastic syndrome.

In some embodiments, microfilter, microfiltration method, and/or diagnosis method described herein is used to diagnosis, characterize, stage, and/or monitor non-small cell lung cancer, pancreatic cancer, breast cancer, ovarian cancer, colorectal cancer, or head and neck cancer.

In some embodiments, microfilter, microfiltration method, and/or diagnosis method described herein is used to diagnosis, characterize, stage, and/or monitor a carcinoma, a tumor, a neoplasm, a lymphoma, a melanoma, a glioma, a sarcoma, or a blastoma.

In some embodiments, the carcinoma comprises adenocarcinoma, adenoid cystic carcinoma, adenosquamous carcinoma, adrenocortical carcinoma, well differentiated carcinoma, squamous cell carcinoma, serous carcinoma, small cell carcinoma, invasive squamous cell carcinoma, large cell carcinoma, islet cell carcinoma, oat cell carcinoma, squamous carcinoma, undifferentiated carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, basal cell carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis.

In some embodiments, the tumor comprises astrocytic tumors, malignant mesothelial tumors, ovarian germ cell tumor, supratentorial primitive neuroectodermal tumors, Wilm's tumor, pituitary tumors, extragonadal germ cell tumor, gastrinoma, germ cell tumors, gestational trophoblastic tumor, brain tumors, pineal and supratentorial primitive neuroectodermal tumors, pituitary tumor, somatostatin-secreting tumor, endodermal sinus tumor, carcinoids, central cerebral astrocytoma, glucagonoma, hepatic adenoma, insulinoma, medulloepithelioma, plasmacytoma, vipoma, and pheochromocytoma.

In some embodiments, the neoplasm comprises intraepithelial neoplasia, multiple myeloma/plasma cell neoplasm, plasma cell neoplasm, interepithelial squamous cell neoplasia, endometrial hyperplasia, focal nodular hyperplasia, hemangioendothelioma, lymphangioleio myomatosis and malignant thymoma.

In some embodiments, the lymphoma comprises nervous system lymphoma, AIDS-related lymphoma, cutaneous T-cell lymphoma, non-Hodgkin's lymphoma, mantle cell lymphoma, follicular lymphoma and Waldenstrom's macroglobulinemia.

In some embodiments, the melanoma comprises acral lentiginous melanoma, superficial spreading melanoma, uveal melanoma, lentigo maligna melanomas, melanoma, intraocular melanoma, adenocarcinoma nodular melanoma, and hemangioma.

In some embodiments, the sarcoma comprises adenomas, adenosarcoma, chondosarcoma, endometrial stromal sarcoma, Ewing's sarcoma, Kaposi's sarcoma, leiomyosarcoma, rhabdomyosarcoma, sarcoma, uterine sarcoma, osteosarcoma, and pseudosarcoma.

In some embodiments, the glioma comprises glioma, brain stem glioma, and hypothalamic and visual pathway glioma.

In some embodiments, the blastoma comprises pulmonary blastoma, pleuropulmonary blastoma, retinoblastoma, neuroblastoma, medulloblastoma, glioblastoma, and hemangiblastomas.

Kits

In various embodiments, provided herein are kits comprising one or more reagents or devices for the performance of the methods disclosed herein. In some embodiments, provided is a kit for isolation, detection, and or analysis of a cell or interest or target cell from a biological sample of a patient.

In some embodiments, a kit comprises a microfilter. The microfilter may comprise a metal such as nickel, palladium or a combination thereof. In some cases, a kit comprises one or more reagents for microfiltration, including, without limitation, wash buffers, fixing agents, and blocking agents.

In some cases, a kit comprises one or more fluorescent probes for the detection of a feature of a target cell. In some embodiments, the kit comprises an antibody having an antigen binding domain specific for one or more of the following antigens: Cytokeratins 8, 18, 19; EpCAM; CD45; CD163; PSMA; AFP; CEA; CA-125; MUC-1; ETA; tyrosinase; MAGE; VEGF; Her2nue; B2M; c-kit/CD117; ER; PR; fibrin and fibrinogen; wherein the antibody is optionally attached to one or more fluorophores. In some embodiments, a kit comprises DAPI, Cy5-anti-CD45, TRITC-anti-EpCAM, FITC-anti-Ck 8, 18, 19, or any combination thereof.

In some cases, the kit comprises a device for holding the microfilter such as a slide or a cassette and optionally associated components thereof. In some embodiments, the kit includes instructions for performing microfiltration. In some embodiments, the kit includes instructions for analyzing a sample enriched on a microfilter using fluorescence microscopy.

In some embodiments, the kit comprises a software application for performing a microfiltration method, for example, using automation. In some embodiments, the kit comprises a software application for performing fluorescence microscopy imaging. In some embodiments, the kit comprises a software module for analyzing one or more images of a microfilter, and determining if cells on the microfilter are target cells.

In some embodiments, a kit provided herein includes a carrier means being compartmentalized to receive in close confinement one or more containers such as vials, tubes, and the like, each of the containers comprising one of the separate elements to be used in a method provided herein.

The following examples are provided to further illustrate the advantages and features of the present disclosure, but are not intended to limit the scope of the disclosure. While they are typical of those that might be used, other procedures, methodologies, or techniques known to those skilled in the art may alternatively be used.

EXAMPLES

Example 1: Micro Filtration of a Biological Sample

Blood samples from cancer and normal patients were drawn for enrichment of tumor derived cells using microfiltration. The microfilter comprised nickel-palladium and had the following structural features: 13 mm diameter, 8 um pore size, and 8 um thickness. The microfilter was assembled into a cassette comprising a fitting for an input syringe and a retention syringe.

For each patient, a 7.5 mL sample of the patient's blood was mixed with fixation buffer. The cassette was attached to a retention syringe, which was subsequently inserted into a syringe pump. An input syringe was then attached to the cassette. All washes and materials applied to the membrane within the cassette were applied through the input syringe. The microfilter was washed with phosphate buffered saline (PBS). The fixed patient blood sample was transferred to the input syringe and the blood sample was drawn from the input syringe, through the microfilter, and into the retention syringe at a low pressure. The filter was washed with PBS, treated with permeabilization buffer, washed with PBS, and blocked with bovine serum albumin A set of probes were applied to the filter in a mixed solution [FITC (anti-Cytokeratins 8, 18, 19), TRITC (anti-EpCAM), and Cy5 (anti-CD45)] onto the microfilter. The cassette was disassembled and the microfilter placed on a microscope slide. A drop of Anti-Fade Reagent was applied onto the microfilter and the microfilter was covered with a cover slip.

Example 2: Analysis of Microfiltration-Isolated Cells from a First Panel of Breast Cancer Patients A first panel of 4 breast cancer patients had their blood drawn, filtered and stained as described in Example 1. Microfilters corresponding to blood samples from each patient were scanned at 40× in order to determine whether TDMCs were observed using the microfilters.

Patient Breast-101 (right lumpectomy, right SNB) was diagnosed with breast cancer. Blood was drawn prior to surgery for a right lumpectomy and right sentinel node biopsy. After blood sample filtering, staining, and microscopic filter membrane imaging at 20× and 40× in a four channel fluorescent microscope, 6 image sets (each image set includes four individual fluorescence channels and a composite) from approximately 500 frame sets were selected for detailed observation. At least 3-4 TDMCs were identified in the images.

Figure 17A:
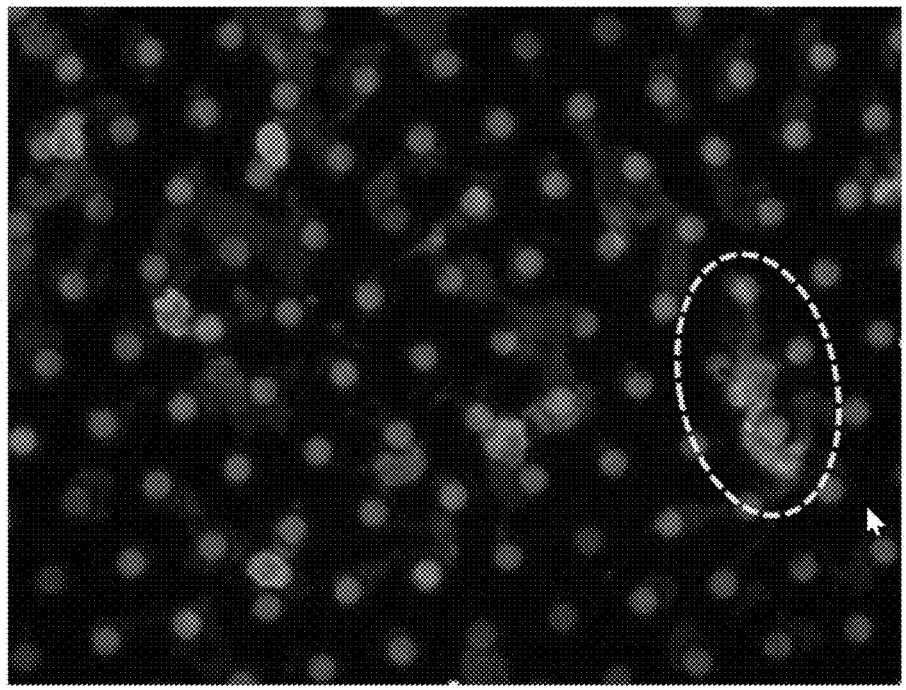
FIG. 17A is a four channel fluoroscopy composite microscope image showing a TDMC from a blood sample taken from a first breast cancer patient as described in Example 2.
Figure 17B:
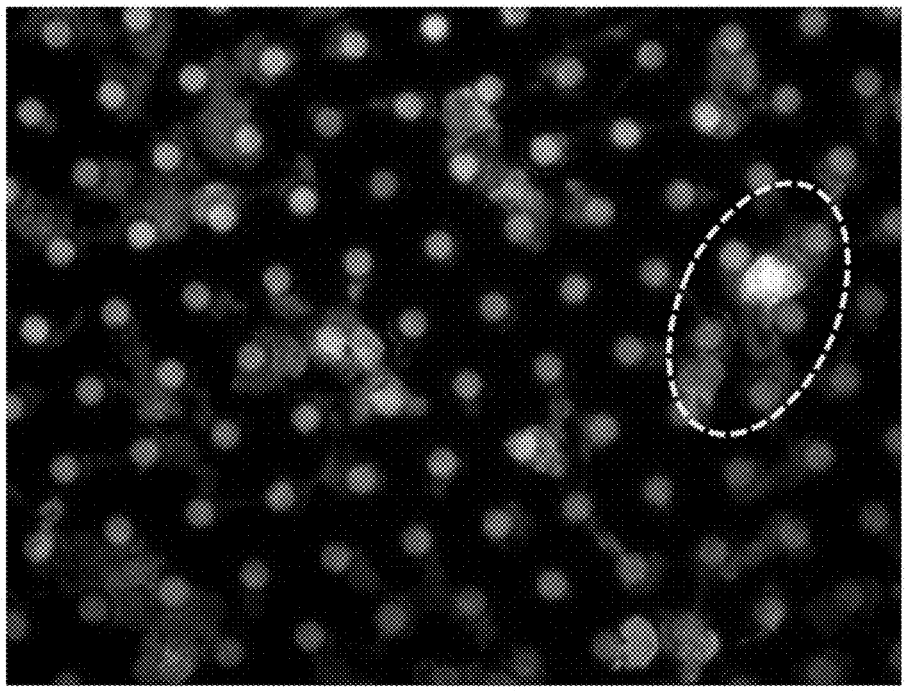
FIG. 17B is a four channel fluoroscopy composite microscope image showing a TDMC from a blood sample taken from a first breast cancer patient as described in Example 2.

Observation of filtered cells from patient Breast-101 demonstrated cells that were DAPI positive (blue channel) and CD45 positive (conjugated with fluorescent dye Cy5 shown as magenta channel), indicating leukocytes, and which had multiple nuclei or irregular nuclei having a dimension greater than 16 µm, and overall cell extant having a dimension greater than 20 µm. Two representative images are shown in FIGS. 17A and 17B. Potential TDMCs are identified with dashed ovals. The images do not have an explicit scale, but the cell dimensions can be approximately ascertained by comparing to the microfilter pore diameter of 8 µm. Takeup of potential TDMCs of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in the composite images and is distinct in the individual channel images.

Patient Breast-102 (left lumpectomy, left SNB) was diagnosed with breast cancer. Blood was drawn prior to surgery for a left lumpectomy and left sentinel node biopsy. After blood sample filtering, staining, and microscopic filter membrane imaging at 20× and 40× in a four channel fluorescent microscope, 7 image sets (each image set includes four individual fluorescence channels and a composite) from approximately 500 frame sets were selected for detailed observation. At least 2-3 TDMCs were identified in the images.

Figure 18A:
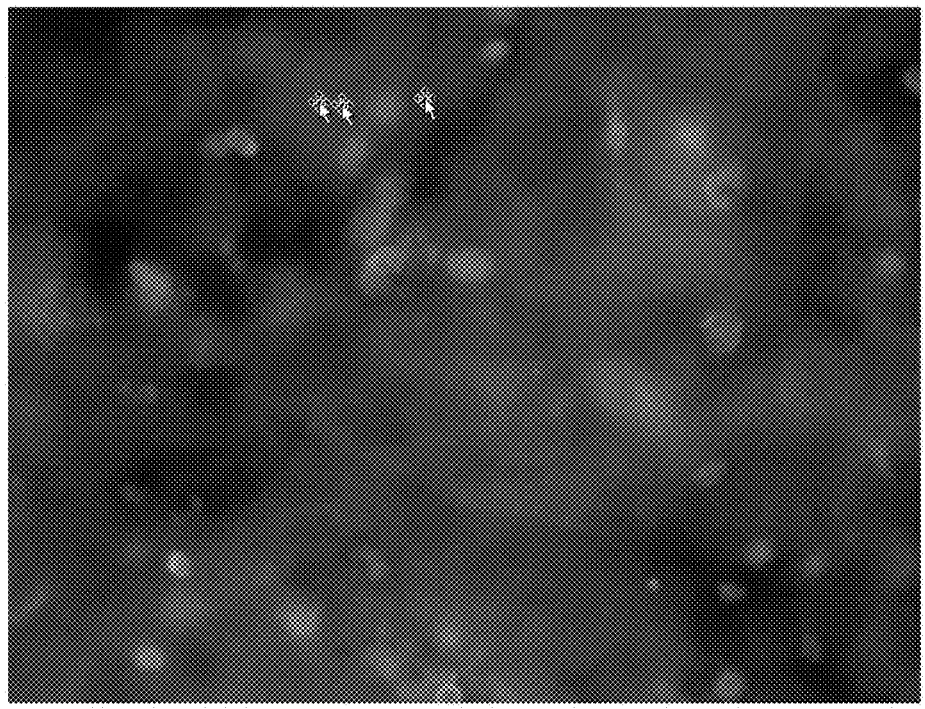
FIG. 18A is a four channel fluoroscopy composite microscope image showing a TDMC from a blood sample taken from a second breast cancer patient as described in Example 2.
Figure 18B:
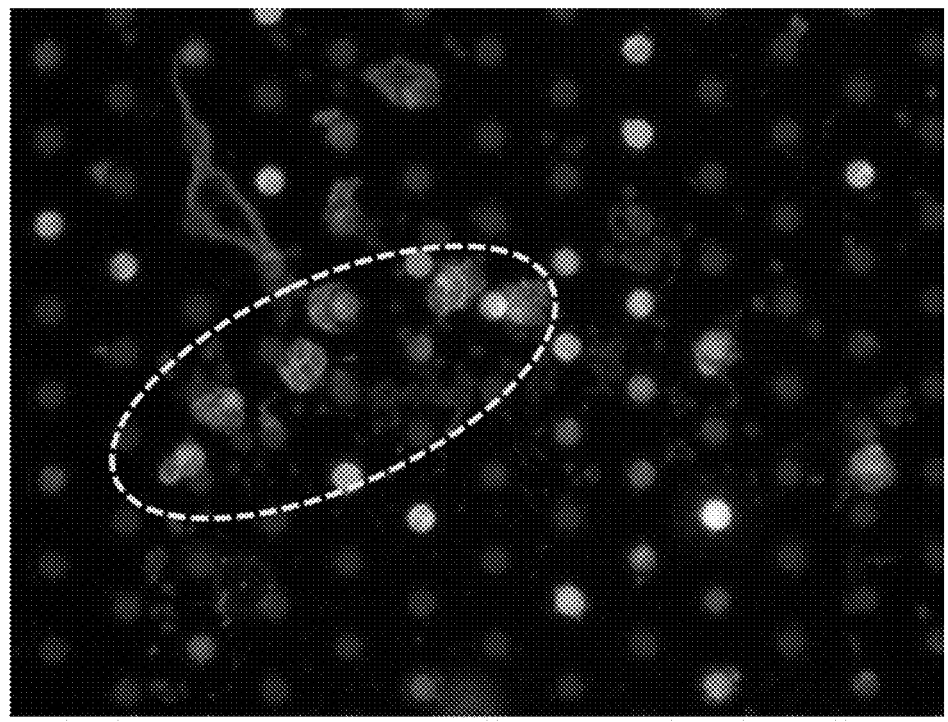
FIG. 18B is a four channel fluoroscopy composite microscope image showing a TDMC from a blood sample taken from a second breast cancer patient as described in Example 2.

Observation of filtered cells from patient Breast-102 demonstrated cells that were DAPI positive (blue channel) and CD45 positive (conjugated with fluorescent dye Cy5 shown as magenta channel), indicating leukocytes, and which had multiple nuclei or irregular nuclei having a dimension greater than 16 µm, and overall cell extant having a dimension greater than 20 µm. Two representative images are shown in FIGS. 18A and 18B. Potential TDMCs are identified with dashed ovals. The images do not have an explicit scale, but the cell dimensions can be approximately ascertained by comparing to the microfilter pore diameter of 8 µm. Indication of takeup of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in the composite images and is distinct in the individual channel images.

Patient Breast-103 (left mastectomy) was diagnosed with breast cancer. Blood was drawn prior to surgery for a left mastectomy. After blood sample filtering, staining, and microscopic filter membrane imaging at 20× and 40× in a four channel fluorescent microscope, 7 image sets (each image set includes four individual fluorescence channels and a composite) from approximately 500 frame sets were selected for detailed observation. At least 1 TDMC was identified in the images.

Figure 19A:
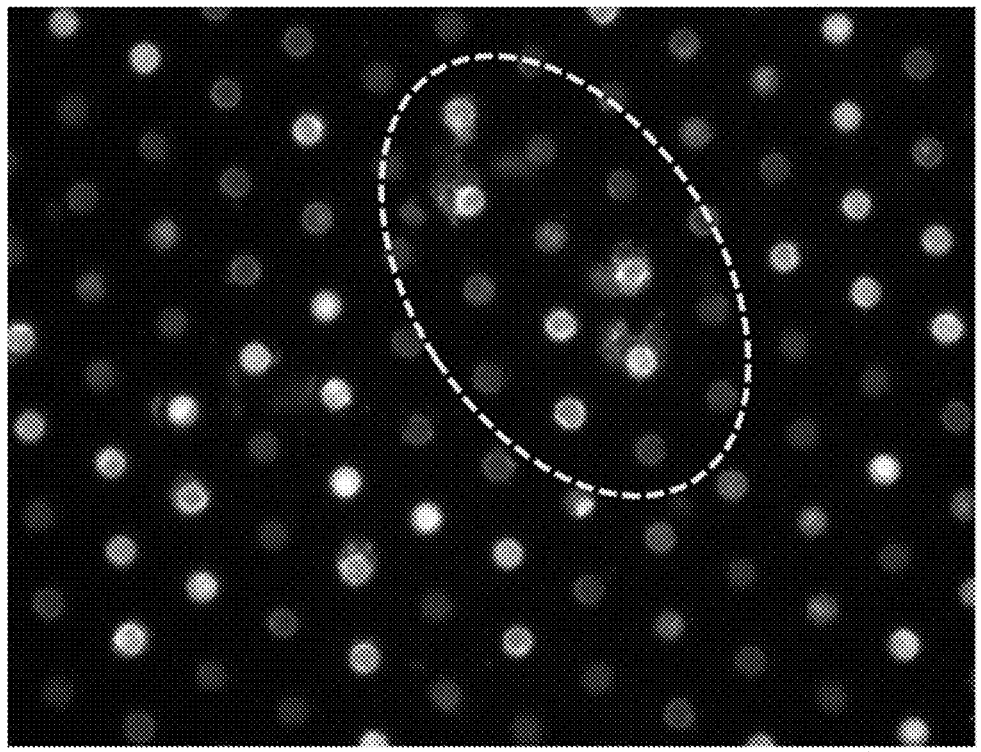
FIG. 19A is a four channel fluoroscopy composite microscope image showing a TDMC from a blood sample taken from a third breast cancer patient as described in Example 2.
Figure 19B:
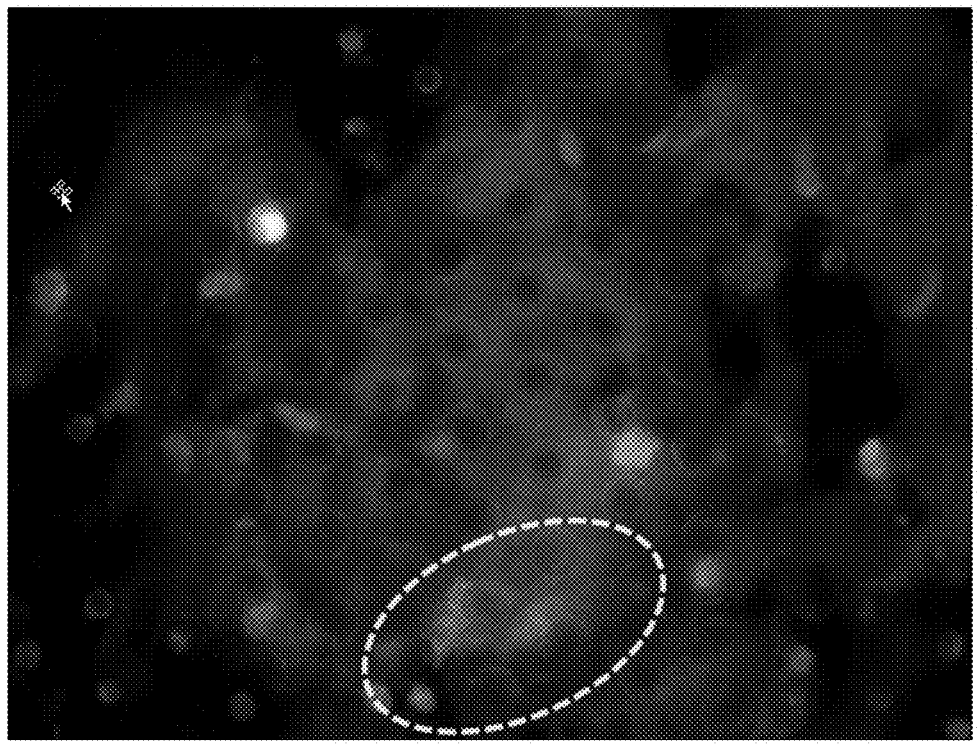
FIG. 19B is a four channel fluoroscopy composite microscope image showing a TDMC from a blood sample taken from a third breast cancer patient as described in Example 2.

Observation of filtered cells from patient Breast-103 demonstrated cells that were DAPI positive (blue channel) and CD45 positive (conjugated with fluorescent dye Cy5 shown as magenta channel), indicating leukocytes, and which had irregular nuclei having a dimension greater than 16 µm and overall cell extant having a dimension greater than 20 µm. Two representative images are shown in FIGS. 19A and 19B. Potential TDMCs are identified with dashed ovals. The images do not have an explicit scale, but the cell dimensions can be approximately ascertained by comparing to the microfilter pore diameter of 8 µm. Some indication of takeup of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in these images.

Patient Breast-104 (right mastectomy) was diagnosed with breast cancer. Blood was drawn prior to surgery for a right mastectomy. After blood sample filtering, staining, and microscopic filter membrane imaging at 20× and 40× in a four channel fluorescent microscope, 14 image sets (each image set includes four individual fluorescence channels and a composite) from approximately 500 frame sets were selected for detailed observation. At least 5-6 TDMCs were identified in the images.

Figure 20A:
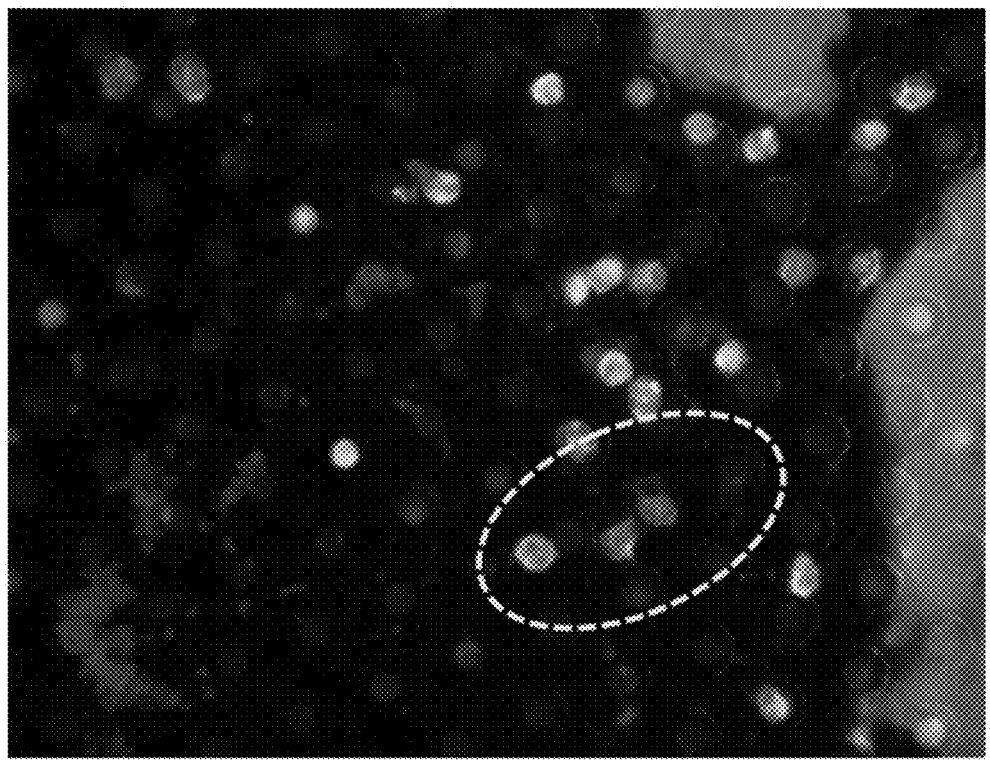
FIG. 20A is a four channel fluoroscopy composite microscope image showing a TDMC from a blood sample taken from a fourth breast cancer patient as described in Example 2.
Figure 20B:
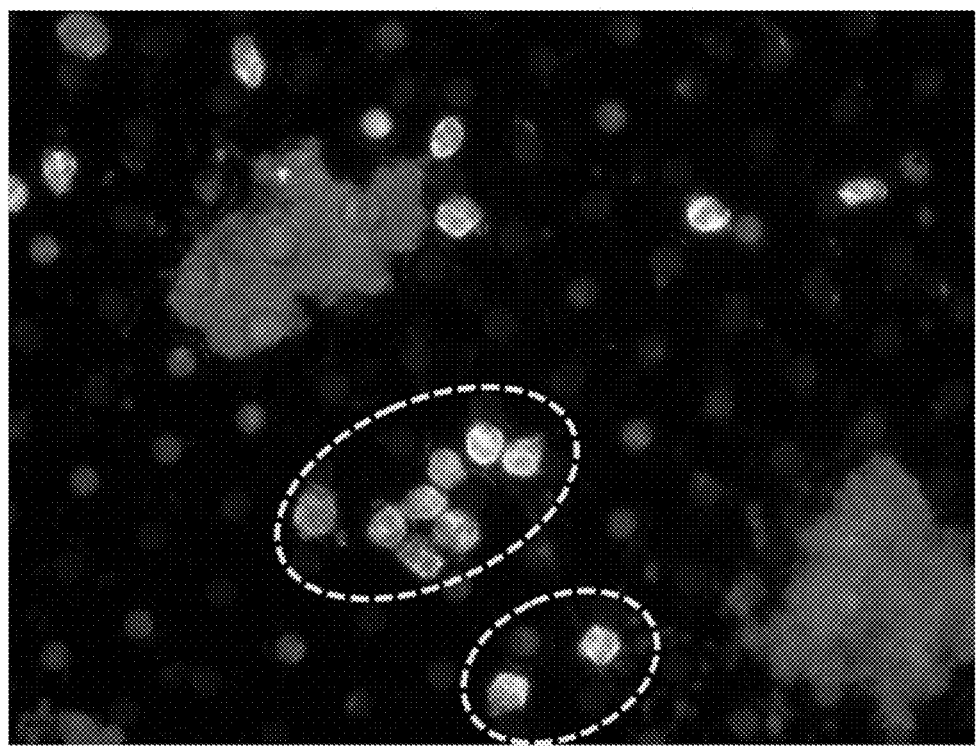
FIG. 20B is a four channel fluoroscopy composite microscope image showing a TDMC from a blood sample taken from a fourth breast cancer patient as described in Example 2.

Observation of filtered cells from patient Breast-104 demonstrated cells that were DAPI positive (blue channel) and CD45 positive (conjugated with fluorescent dye Cy5 shown as magenta channel), indicating leukocytes, and which had irregular nuclei having a dimension greater than 16 µm and overall cell extant having a dimension greater than 20 µm. Two representative images are shown in FIGS. 20A and 20B. Potential TDMCs are identified with dashed ovals. The images do not have an explicit scale, but the cell dimensions can be approximately ascertained by comparing to the microfilter pore diameter of 8 µm. Some indication of takeup of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in these images.

Figure 20C:
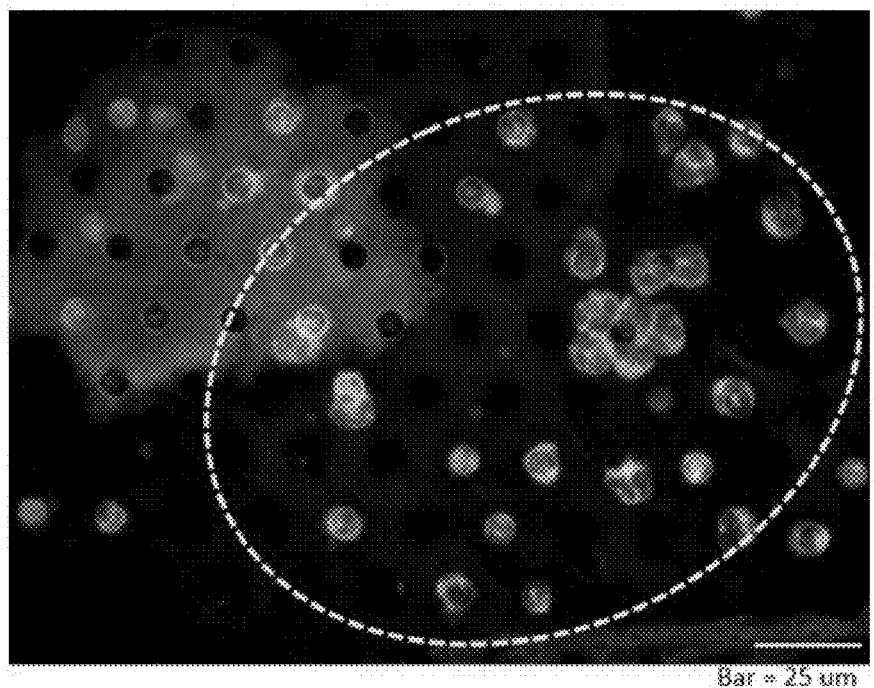
FIG. 20C is a four channel fluoroscopy composite microscope image showing a TDMC from a blood sample taken from a fourth breast cancer patient as described in Example 2.
Figure 20D:
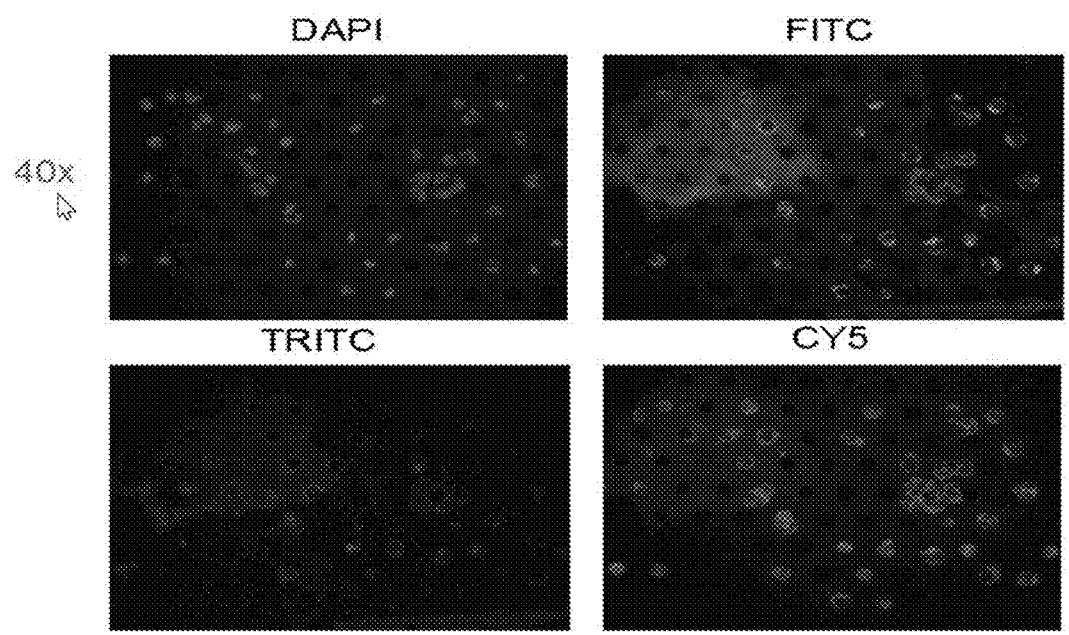
FIG. 20D is four microscope images of the four individual fluorescence channels showing a TDMC from a blood sample taken from a fourth breast cancer patient as described in Example 2.

FIG. 20C shows another composite image from patient Breast-104. FIG. 20D is the corresponding individual channels image. FIG. 20D shows the presence of all four stains in a number of cells.

Example 3: Analysis of Microfiltration-Isolated Cells from Normal Patients

A panel of normal patients had their blood drawn, filtered and stained as described in Example 1. Microfilters corresponding to blood samples from each patient were scanned at 40× in order to determine whether TDMCs were observed using the microfilters.

Figure 21:
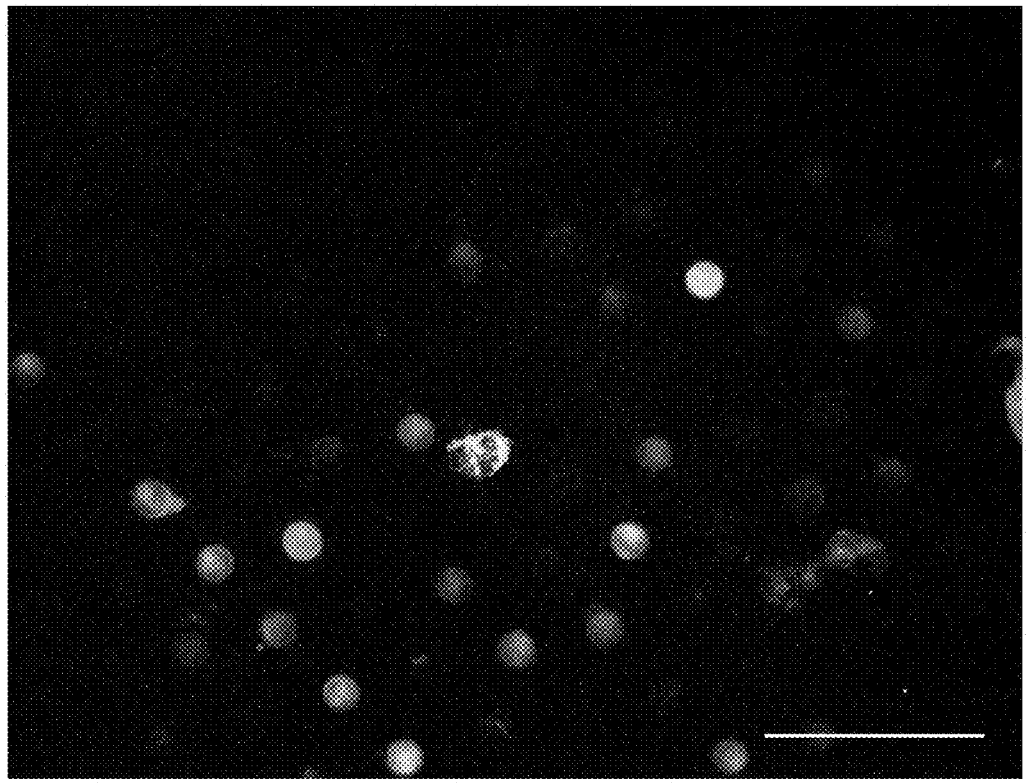
FIG. 21 is a four channel fluoroscopy composite microscope image showing that there are no TDMCs found in a blood sample taken from a first normal patient as described in Example 3.

Normal Subject Female Normal-001F: Blood was Drawn from Normal Subject N-001F. After blood sample filtering, staining, and microscopic filter membrane imaging at 20× and 40× in a four channel fluorescent microscope, approximately 500 frame sets were analyzed. As shown by the sample image of FIG. 21, no TDMCs were found in this sample.

Figure 22:
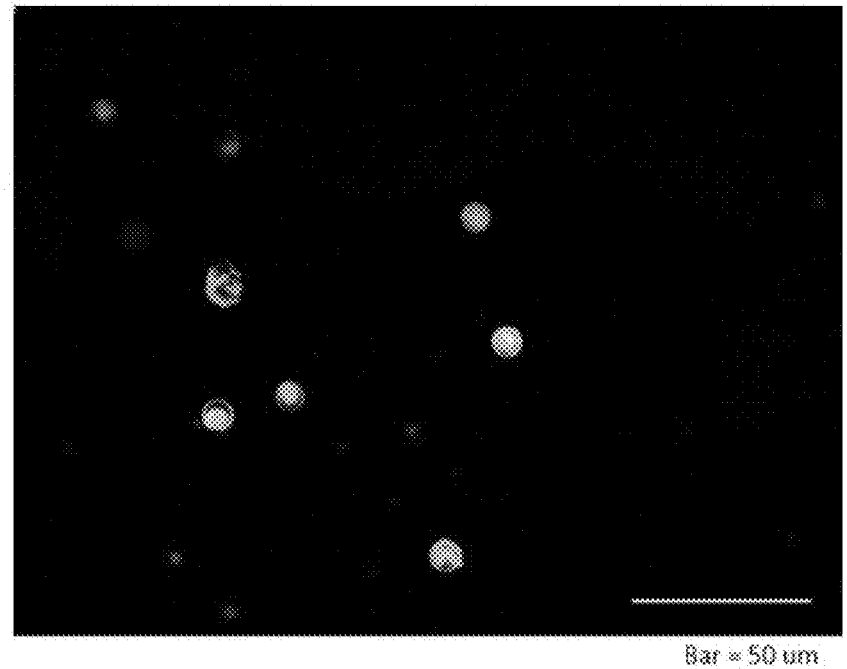
FIG. 22 is a four channel fluoroscopy composite microscope image showing that there are no TDMCs found in a blood sample taken from a second normal patient as described in Example 3.

Normal Subject Female Normal-002F: Blood was drawn from normal subject N-002F. After blood sample filtering, staining, and microscopic filter membrane imaging at 20× and 40× in a four channel fluorescent microscope, approximately 500 frame sets were analyzed. As shown by the sample image of FIG. 22, no TDMCs were found in this sample.

Example 4: Analysis of Microfiltration-Isolated Cells from a Second Panel of Breast Cancer Patients A second panel of 4 breast cancer patients had their blood drawn, filtered and stained as described in Example 1. Microfilters corresponding to blood samples from each patient were scanned at 40× in order to determine whether TDMCs were observed using the microfilters.

Patient Breast-201 (right lumpectomy, right SNB) was diagnosed with breast cancer. Blood was drawn prior to surgery for a right lumpectomy and right sentinel node biopsy. After blood sample filtering, staining, and microscopic filter membrane imaging at 20× and 40× in a four channel fluorescent microscope, 6 image sets (each image set includes four individual fluorescence channels and a composite) from approximately 500 frame sets were selected for detailed observation. At least 4-5 TDMCs were identified in the images.

Figure 23:
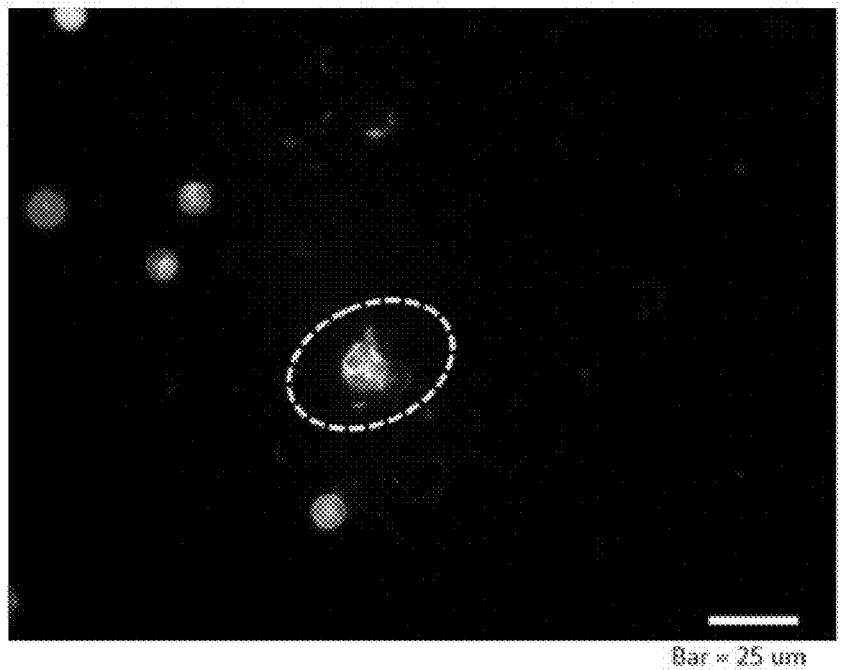
FIG. 23 is a four channel fluoroscopy composite microscope image showing a TDMC from a blood sample taken from a fifth breast cancer patient as described in Example 4.

Observation of filtered cells from patient Breast-201 demonstrated cells that were DAPI positive (blue channel) and CD45 positive (conjugated with fluorescent dye Cy5 shown as magenta channel), indicating leukocytes, and which had multiple nuclei or irregular nuclei having a dimension greater than 16 µm, and overall cell extant having a dimension greater than 20 µm. A representative image is shown in FIG. 23. A potential TDMC is identified with dashed ovals. Indication of takeup of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in the composite images and is distinct in the individual channel images.

Patient Breast-202 (right lumpectomy, right SNB) was diagnosed with breast cancer. Blood was drawn prior to surgery for a right lumpectomy and right sentinel node biopsy. After blood sample filtering, staining, and microscopic filter membrane imaging at 20× and 40× in a four channel fluorescent microscope, 6 image sets (each image set includes four individual fluorescence channels and a composite) from approximately 500 frame sets were selected for detailed observation. At least 3-4 TDMCs were identified in the images.

Figure 24A:
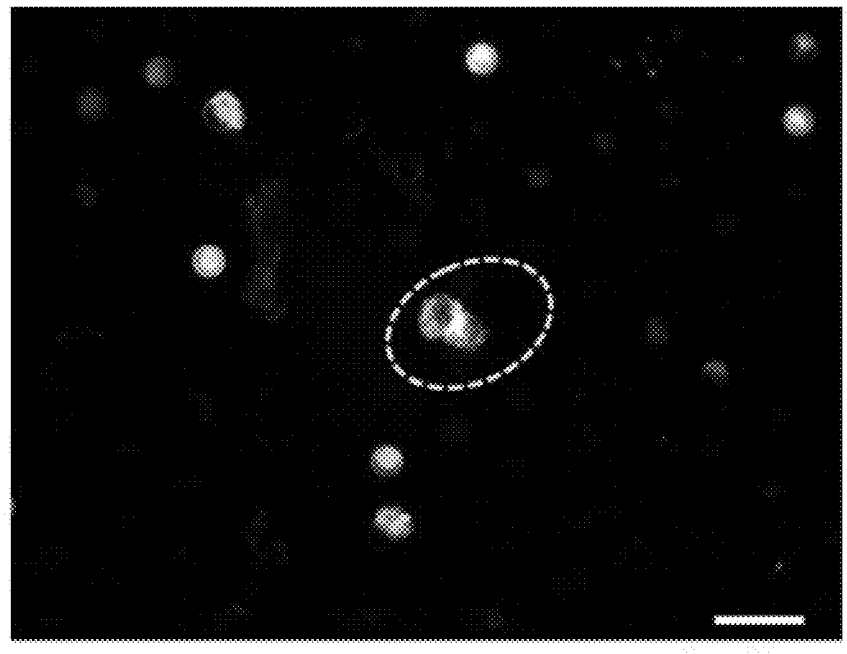
FIG. 24A is a four channel fluoroscopy composite microscope image showing a TDMC from a blood sample taken from a sixth breast cancer patient as described in Example 4.
Figure 24B:
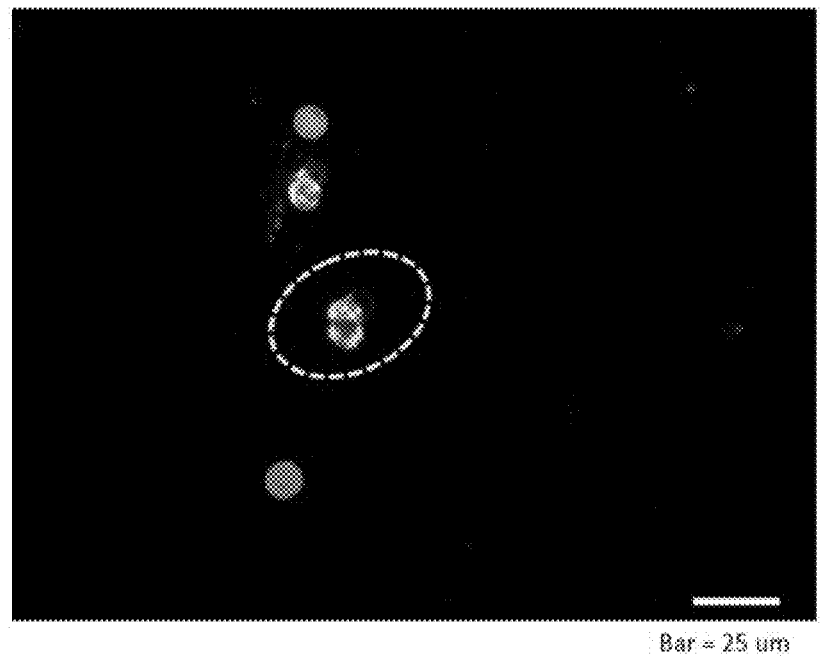
FIG. 24B is a four channel fluoroscopy composite microscope image showing a TDMC from a blood sample taken from a sixth breast cancer patient as described in Example 4.
Figure 24C:
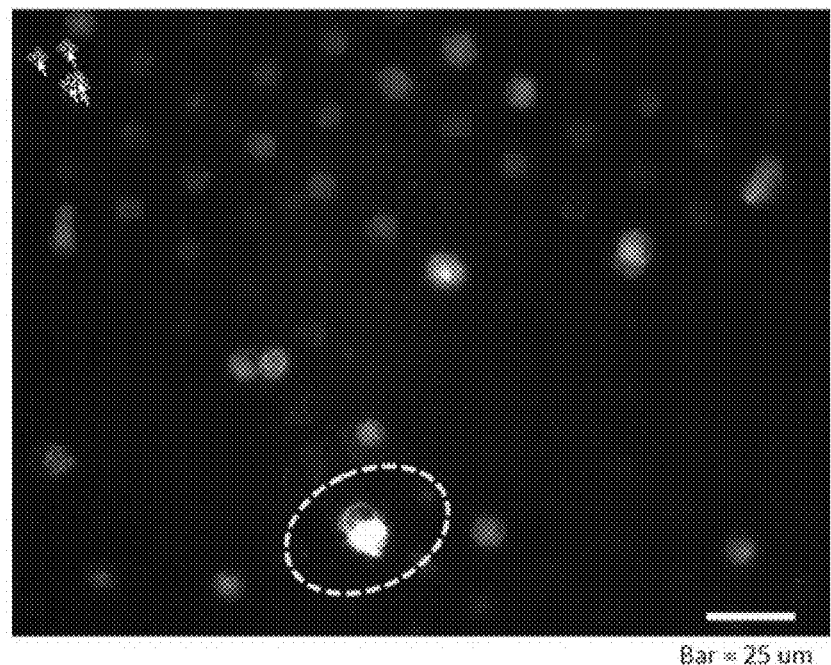
FIG. 24C is a four channel fluoroscopy composite microscope image showing a TDMC from a blood sample taken from a sixth breast cancer patient as described in Example 4.
Figure 25A:
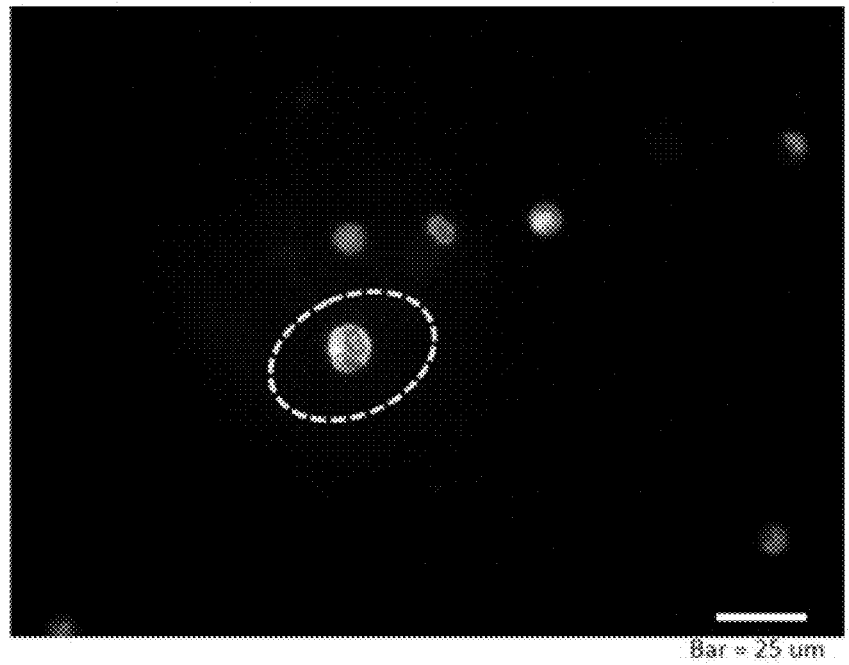
FIG. 25A is a four channel fluoroscopy composite microscope image showing a TDMC from a blood sample taken from a seventh breast cancer patient as described in Example 4.
Figure 25B:
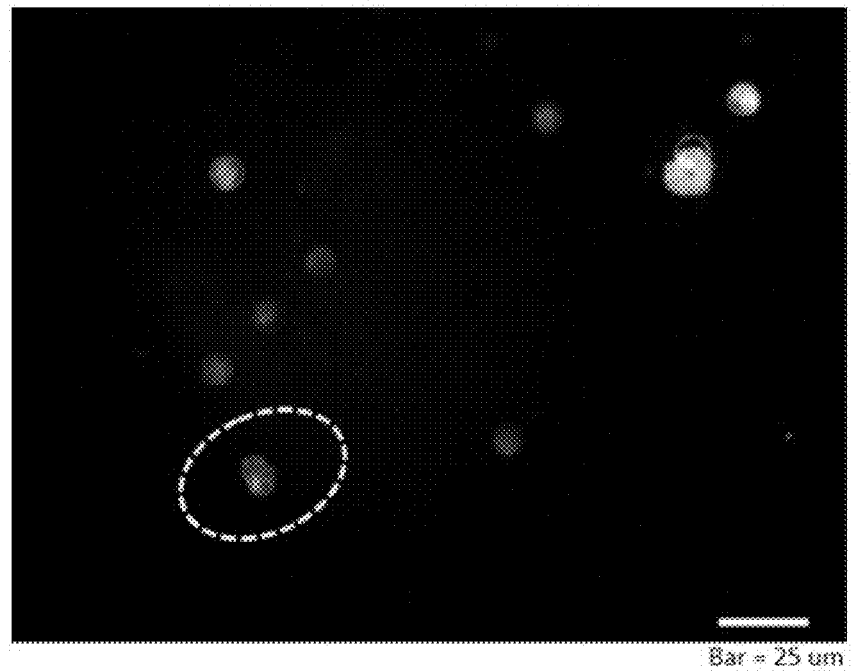
FIG. 25B is a four channel fluoroscopy composite microscope image showing a TDMC from a blood sample taken from a seventh breast cancer patient as described in Example 4.
Figure 25C:
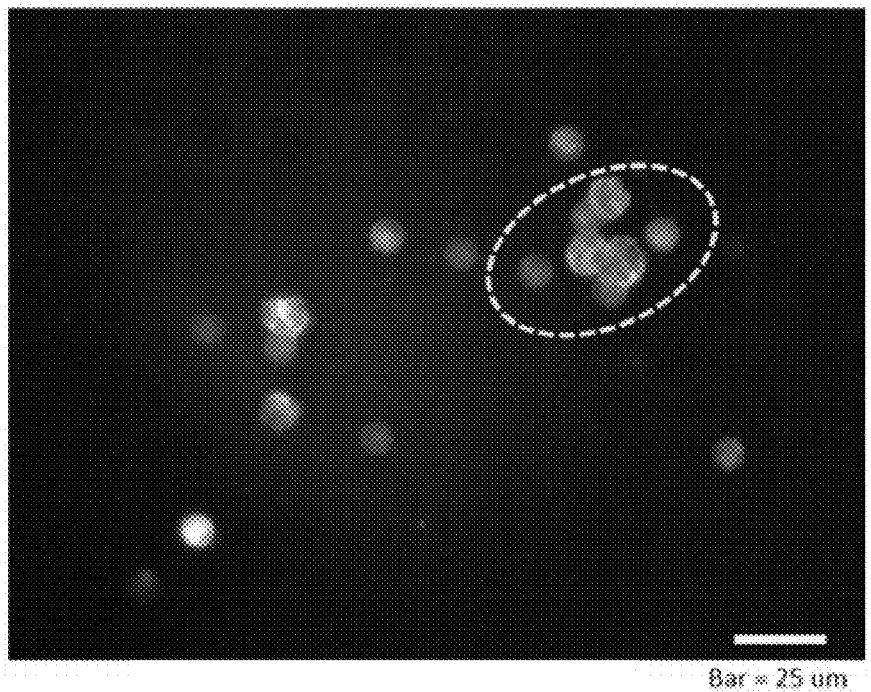
FIG. 25C is a four channel fluoroscopy composite microscope image showing a TDMC from a blood sample taken from a seventh breast cancer patient as described in Example 4.
Figure 25D:
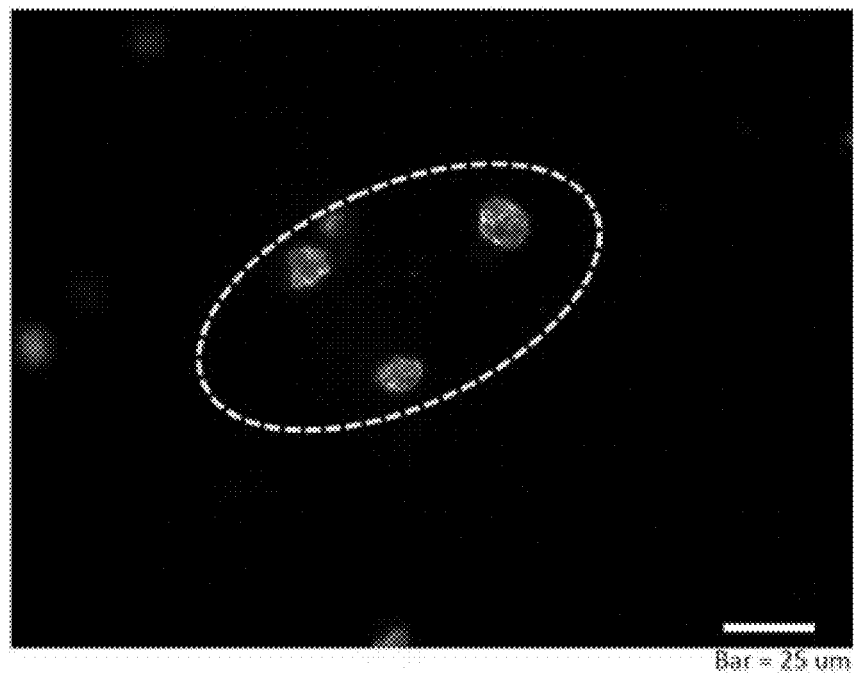
FIG. 25D is a four channel fluoroscopy composite microscope image showing a TDMC from a blood sample taken from a seventh breast cancer patient as described in Example 4.
Figure 25E:
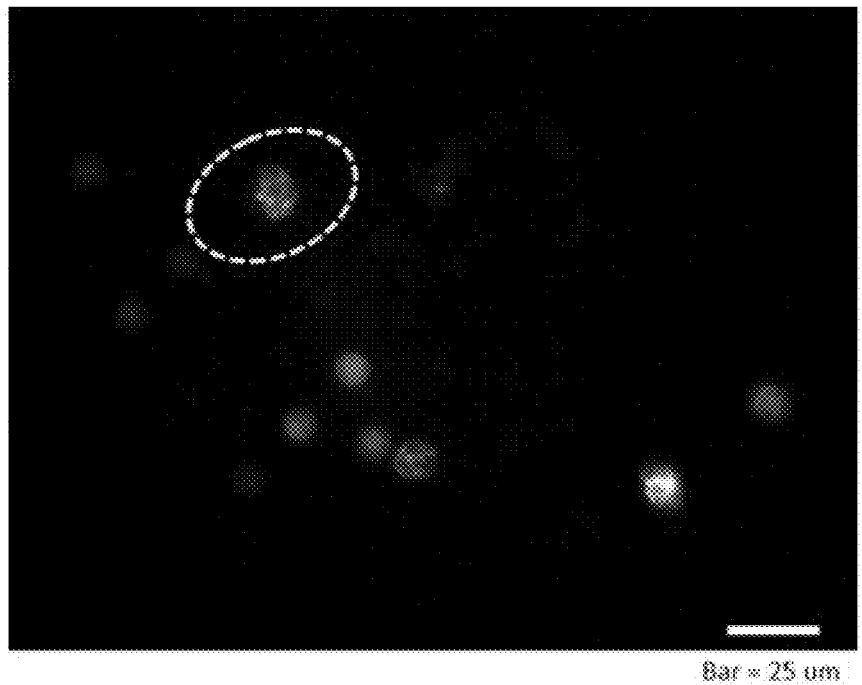
FIG. 25E is a four channel fluoroscopy composite microscope image showing a TDMC from a blood sample taken from a seventh breast cancer patient as described in Example 4.
Figure 25F:
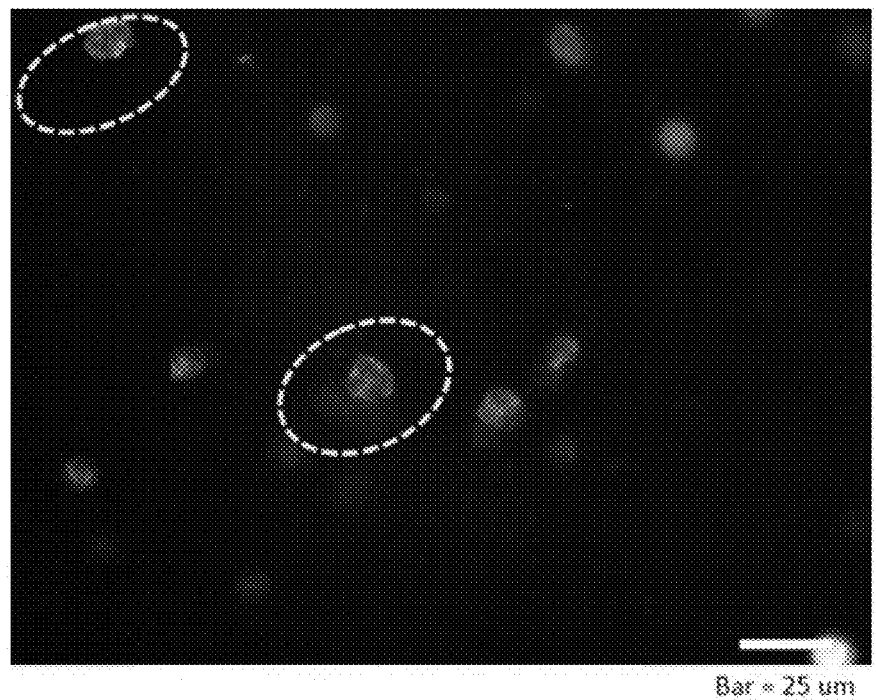
FIG. 25F is a four channel fluoroscopy composite microscope image showing a TDMC from a blood sample taken from a seventh breast cancer patient as described in Example 4.
Figure 25G:
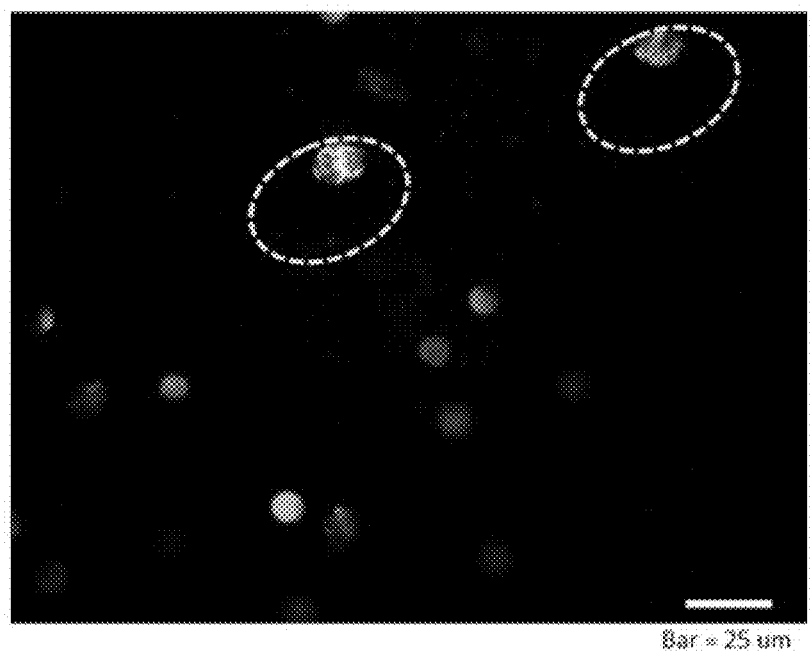
FIG. 25G is a four channel fluoroscopy composite microscope image showing a TDMC from a blood sample taken from a seventh breast cancer patient as described in Example 4.
Figure 25H:
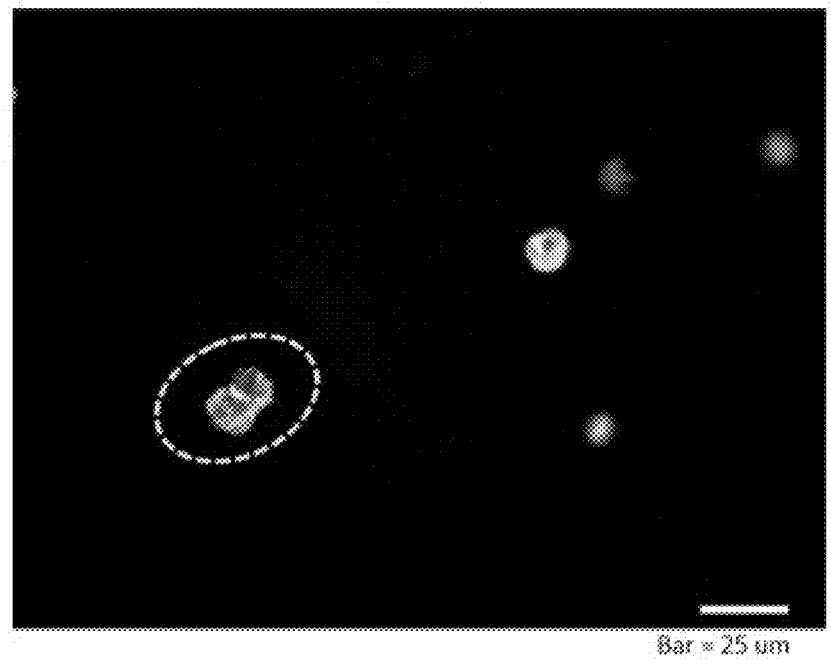
FIG. 25H is a four channel fluoroscopy composite microscope image showing a TDMC from a blood sample taken from a seventh breast cancer patient as described in Example 4.
Figure 26A:
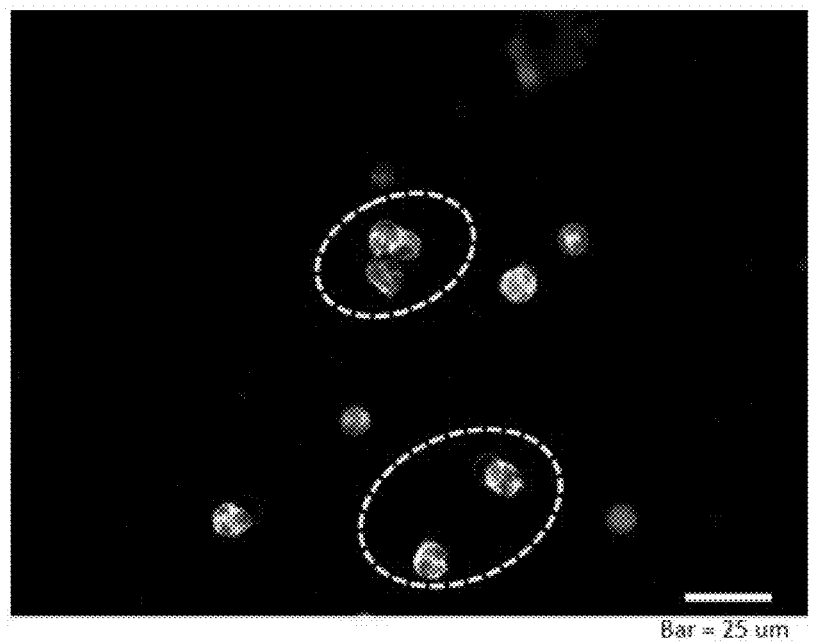
FIG. 26A is a four channel fluoroscopy composite microscope image showing a TDMC from a blood sample taken from an eighth breast cancer patient as described in Example 4.
Figure 26B:
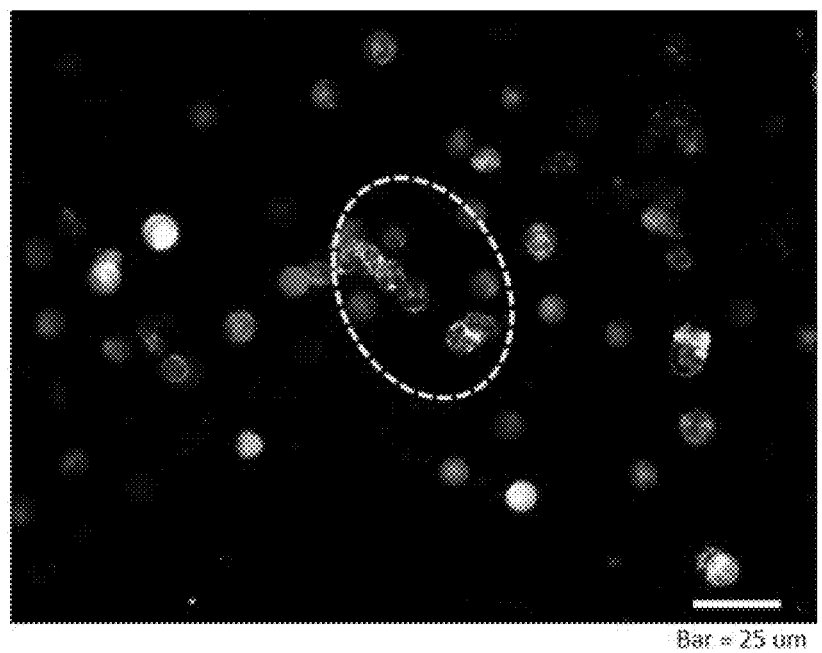
FIG. 26B is a four channel fluoroscopy composite microscope image showing a TDMC from a blood sample taken from an eighth breast cancer patient as described in Example 4.
Figure 26C:
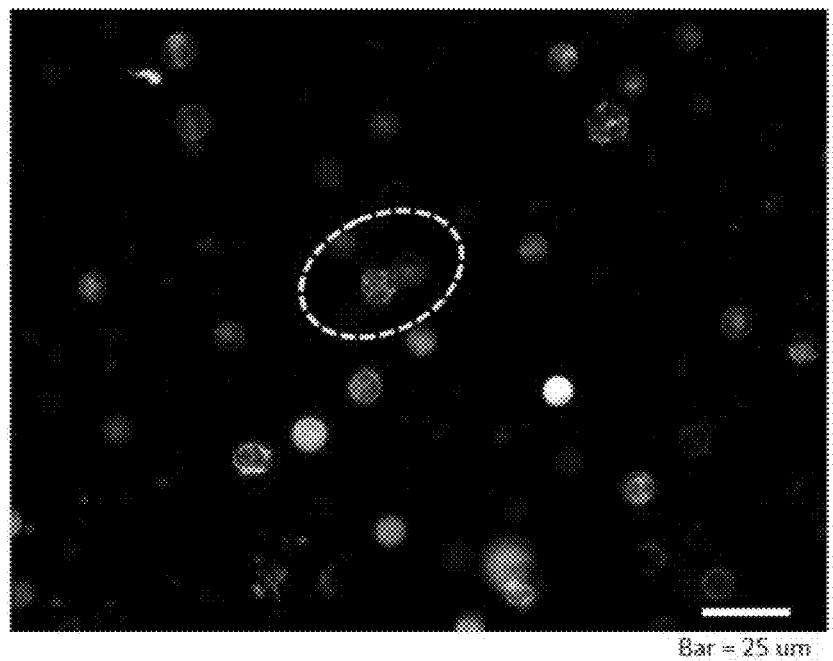
FIG. 26C is a four channel fluoroscopy composite microscope image showing a TDMC from a blood sample taken from an eighth breast cancer patient as described in Example 4.
Figure 26D:
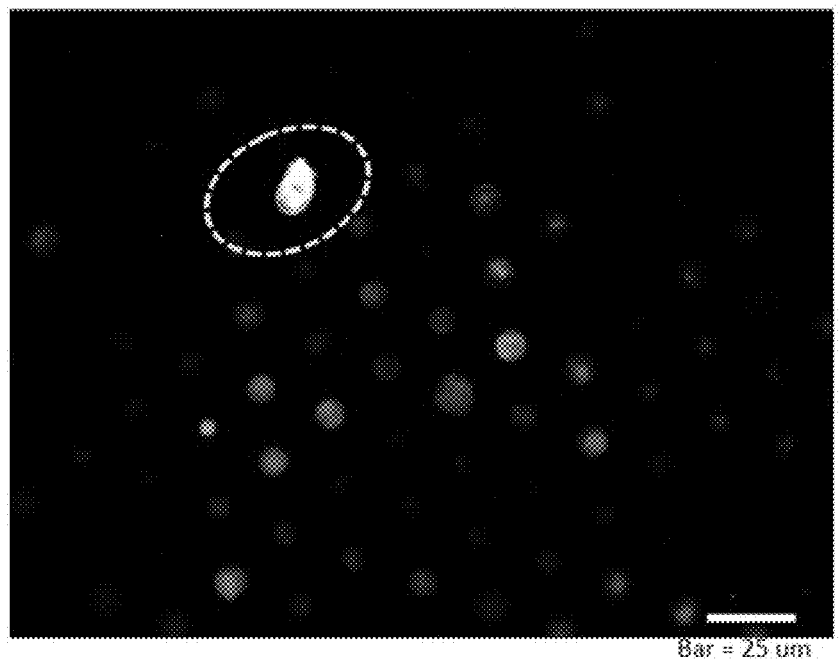
FIG. 26D is a four channel fluoroscopy composite microscope image showing a TDMC from a blood sample taken from an eighth breast cancer patient as described in Example 4.
Figure 26E:
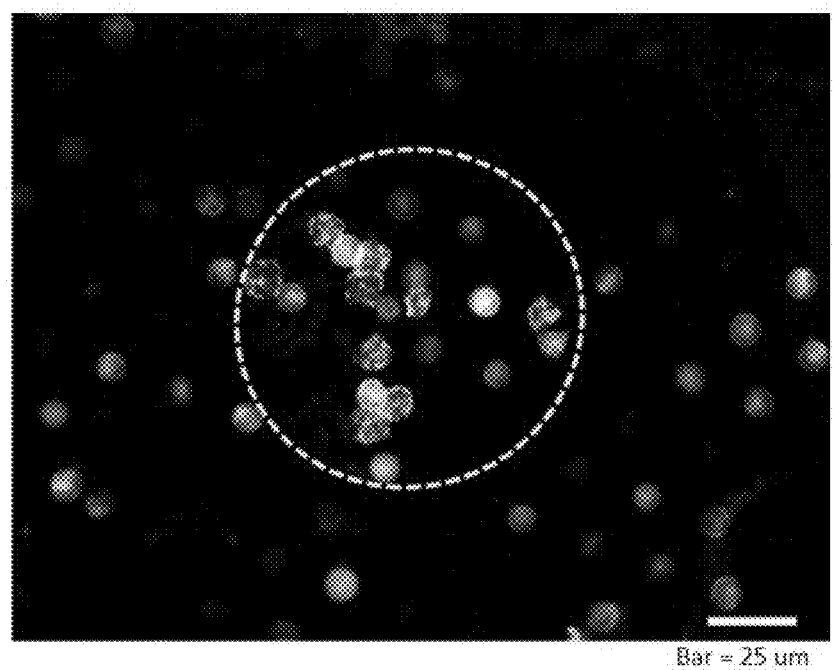
FIG. 26E is a four channel fluoroscopy composite microscope image showing a TDMC from a blood sample taken from an eighth breast cancer patient as described in Example 4.

Observation of filtered cells from patient Breast-202 demonstrated cells that were DAPI positive (blue channel) and CD45 positive (conjugated with fluorescent dye Cy5 shown as magenta channel), indicating leukocytes, and which had multiple nuclei or irregular nuclei having a dimension greater than 16 µm, and overall cell extant having a dimension greater than 20 µm. Representative images are shown in FIGS. 24A-C. A potential TDMC is identified with dashed ovals. Indication of takeup of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in the composite images and is distinct in the individual channel images.

Patient Breast-203 (left lumpectomy NL, left SNB) was diagnosed with breast cancer. Blood was drawn prior to surgery for a left lumpectomy and left sentinel node biopsy. After blood sample filtering, staining, and microscopic filter membrane imaging at 20× and 40× in a four channel fluorescent microscope, 14 image sets (each image set includes four individual fluorescence channels and a composite) from approximately 500 frame sets were selected for detailed observation. At least 8-9 TDMCs were identified in the images.

Observation of filtered cells from patient Breast-203 demonstrated cells that were DAPI positive (blue channel) and CD45 positive (conjugated with fluorescent dye Cy5 shown as magenta channel), indicating leukocytes, and which had multiple nuclei or irregular nuclei having a dimension greater than 16 µm, and overall cell extant having a dimension greater than 20 µm. Representative images are shown in FIGS. 25A-H. Potential TDMCs are identified with dashed ovals. Indication of takeup of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in the composite images and is distinct in the individual channel images.

Patient Breast-204 (right lumpectomy, right SNB) was diagnosed with breast cancer. Blood was drawn prior to surgery for a right lumpectomy and right sentinel node biopsy. After blood sample filtering, staining, and microscopic filter membrane imaging at 20× and 40× in a four channel fluorescent microscope, 13 image sets (each image set includes four individual fluorescence channels and a composite) from approximately 500 frame sets were selected for detailed observation. At least 2-3 TDMCs were identified in the images.

Observation of filtered cells from patient Breast-204 demonstrated cells that were DAPI positive (blue channel) and CD45 positive (conjugated with fluorescent dye Cy5 shown as magenta channel), indicating leukocytes, and which had multiple nuclei or irregular nuclei having a dimension greater than 16 µm, and overall cell extant having a dimension greater than 20 µm. A representative image is shown in FIGS. 26A-E. A potential TDMC is identified with dashed ovals. Indication of takeup of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in the composite images and is distinct in the individual channel images.

Patient Breast-205 (right and left (prophylactic) mastectomy, right SNB) was diagnosed with breast cancer. Blood was drawn prior to surgery for a right mastectomy, left prophylactic mastectomy and right sentinel node biopsy. After blood sample filtering, staining, and microscopic filter membrane imaging at 20× and 40× in a four channel fluorescent microscope, 4 image sets (each image set includes four individual fluorescence channels and a composite) from approximately 500 frame sets were selected for detailed observation. At least 2-3 TDMCs were identified in the images.

Figure 27A:
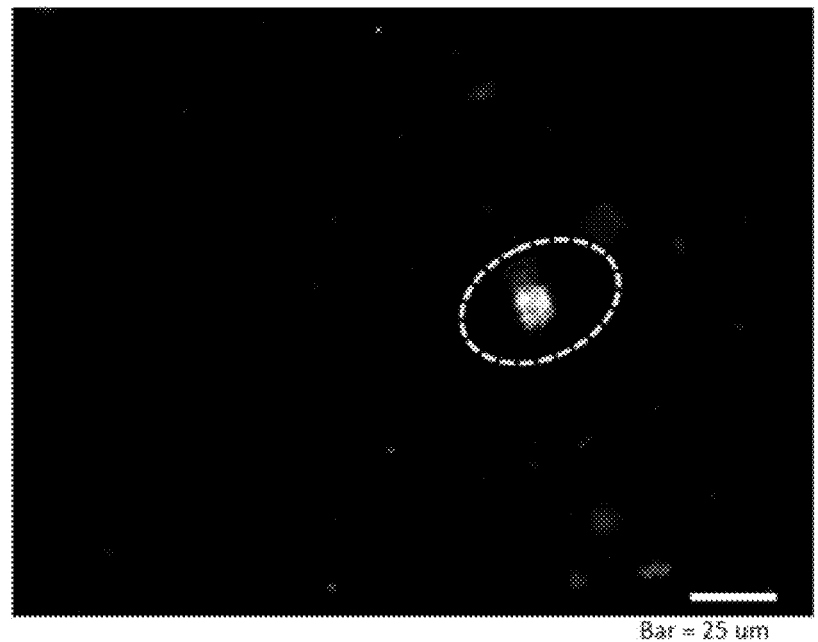
FIG. 27A is a four channel fluoroscopy composite microscope image showing a TDMC from a blood sample taken from a ninth breast cancer patient as described in Example 4.
Figure 27B:
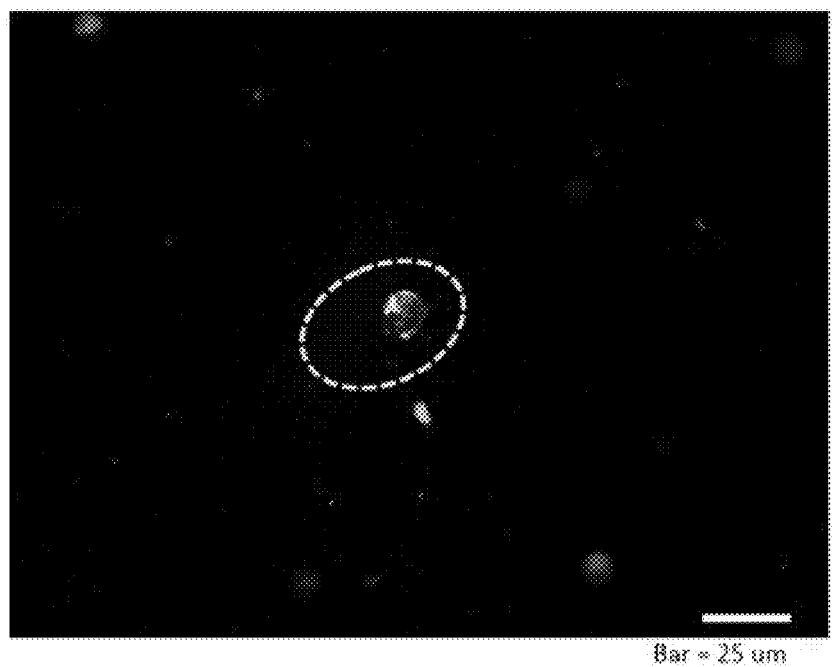
FIG. 27B is a four channel fluoroscopy composite microscope image showing a TDMC from a blood sample taken from a ninth breast cancer patient as described in Example 4.
Figure 27C:
FIG. 27C is a four channel fluoroscopy composite microscope image showing a TDMC from a blood sample taken from a ninth breast cancer patient as described in Example 4.
Figure 28A:
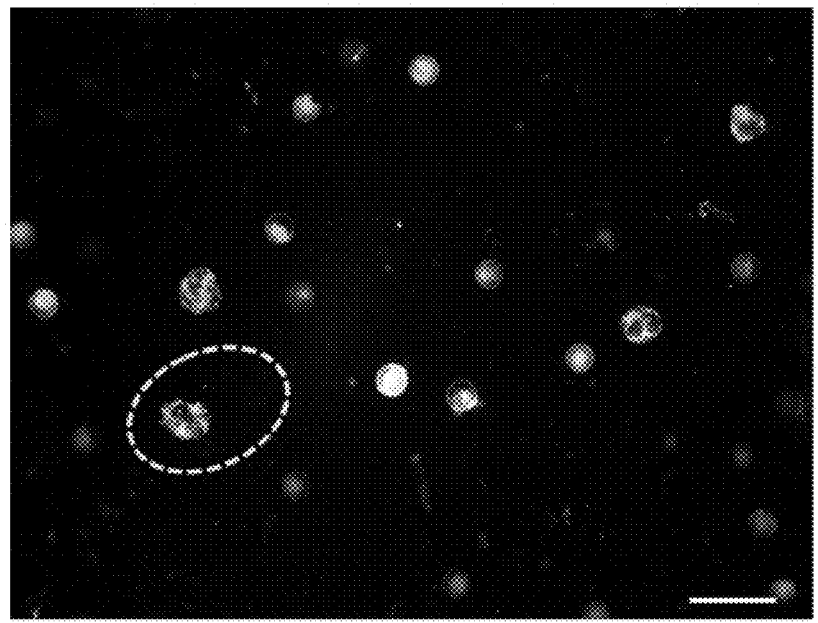
FIG. 28A is a four channel fluoroscopy composite microscope image showing a TDMC from a blood sample taken from a tenth breast cancer patient as described in Example 4.
Figure 28B:
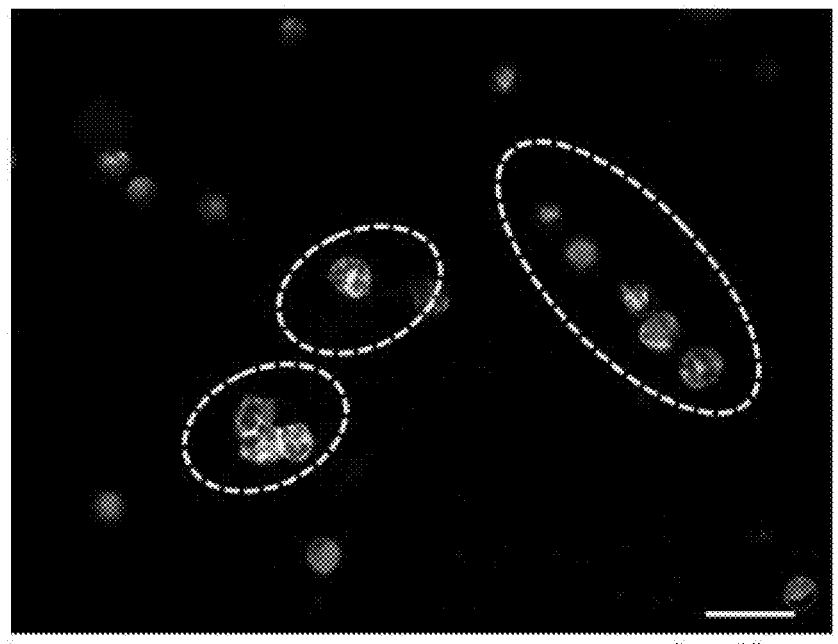
FIG. 28B is a four channel fluoroscopy composite microscope image showing a TDMC from a blood sample taken from a tenth breast cancer patient as described in Example 4.
Figure 28C:
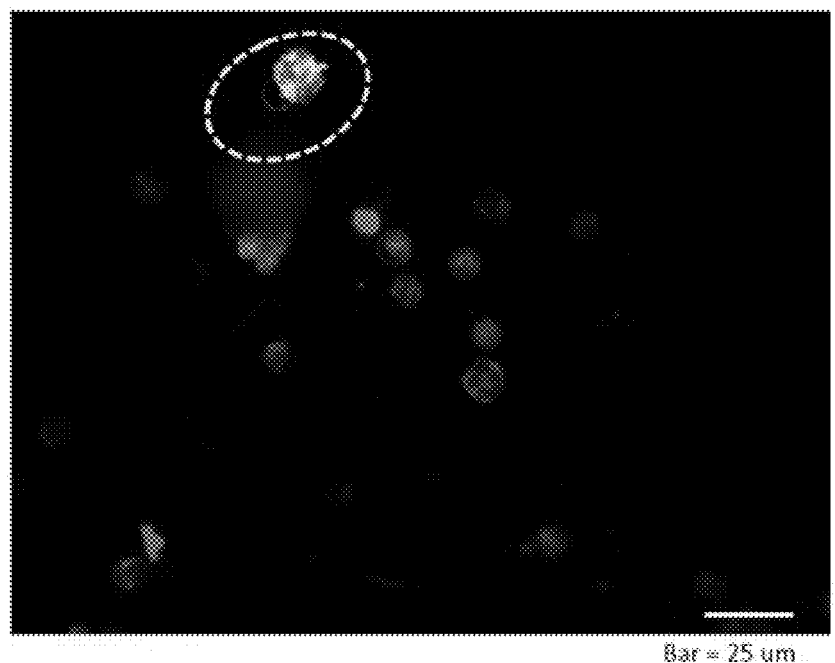
FIG. 28C is a four channel fluoroscopy composite microscope image showing a TDMC from a blood sample taken from a tenth breast cancer patient as described in Example 4.
Figure 28D:
FIG. 28D is a four channel fluoroscopy composite microscope image showing a TDMC from a blood sample taken from a tenth breast cancer patient as described in Example 4.

Observation of filtered cells from patient Breast-205 demonstrated cells that were DAPI positive (blue channel) and CD45 positive (conjugated with fluorescent dye Cy5 shown as magenta channel), indicating leukocytes, and which had multiple nuclei or irregular nuclei having a dimension greater than 16 µm, and overall cell extant having a dimension greater than 20 µm. A representative image is shown in FIGS. 27A-C. A potential TDMC is identified with dashed ovals. Indication of takeup of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in the composite images and is distinct in the individual channel images.

Patient Breast-206 (right lumpectomy, right SNB) was diagnosed with breast cancer. Blood was drawn prior to surgery for a right lumpectomy and right sentinel node biopsy. After blood sample filtering, staining, and microscopic filter membrane imaging at 20× and 40× in a four channel fluorescent microscope, 21 image sets (each image set includes four individual fluorescence channels and a composite) from approximately 500 frame sets were selected for detailed observation. At least 17-20 TDMCs were identified in the images.

Observation of filtered cells from patient Breast-206 demonstrated cells that were DAPI positive (blue channel) and CD45 positive (conjugated with fluorescent dye Cy5 shown as magenta channel), indicating leukocytes, and which had multiple nuclei or irregular nuclei having a dimension greater than 16 µm, and overall cell extant having a dimension greater than 20 µm. A representative image is shown in FIGS. 28A-D. A potential TDMC is identified with dashed ovals. Indication of takeup of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in the composite images and is distinct in the individual channel images.

Patient Breast-207 (left lumpectomy, left SNB) was diagnosed with breast cancer. Blood was drawn prior to surgery for a left lumpectomy and left sentinel node biopsy. After blood sample filtering, staining, and microscopic filter membrane imaging at 20× and 40× in a four channel fluorescent microscope, 10 image sets (each image set includes four individual fluorescence channels and a composite) from approximately 500 frame sets were selected for detailed observation. At least 3 TDMCs were identified in the images.

Figure 29A:
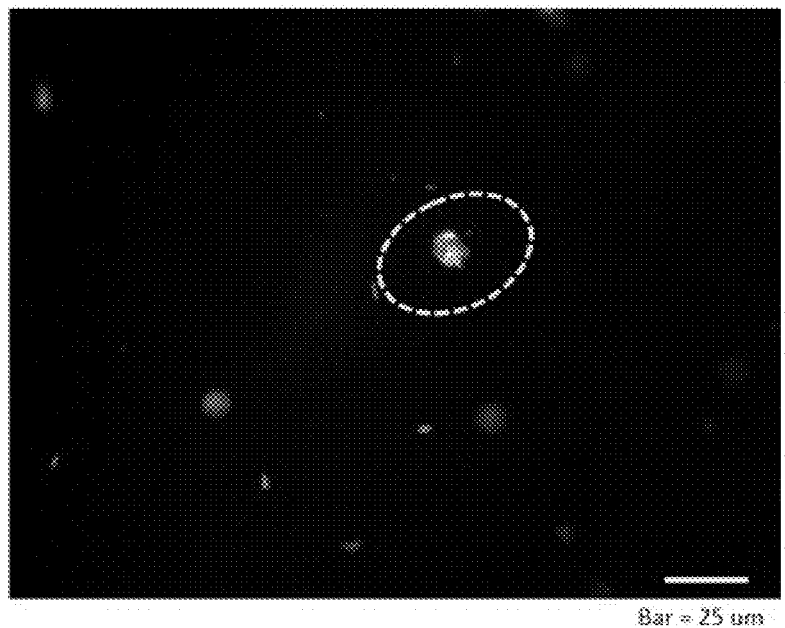
FIG. 29A is a four channel fluoroscopy composite microscope image showing a TDMC from a blood sample taken from an eleventh breast cancer patient as described in Example 4.
Figure 29B:
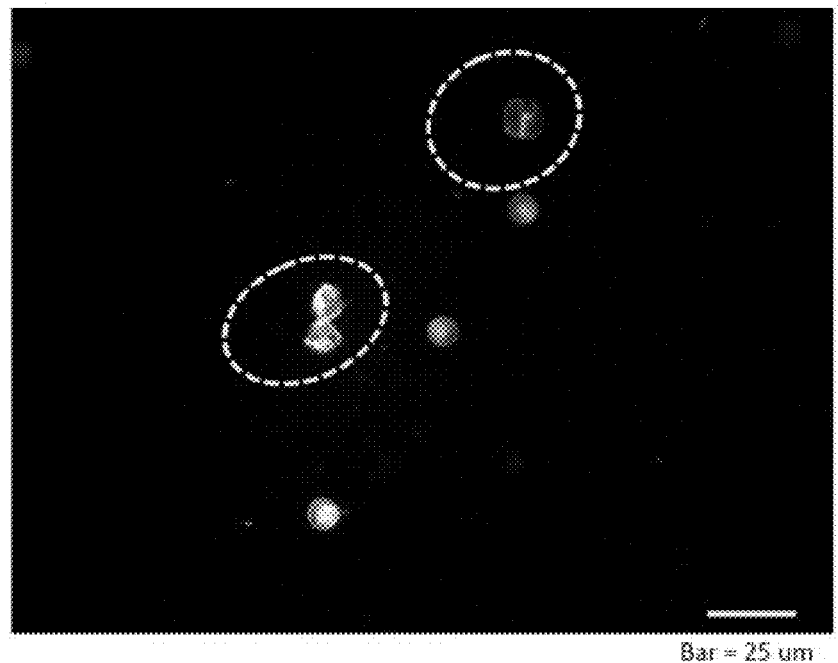
FIG. 29B is a four channel fluoroscopy composite microscope image showing a TDMC from a blood sample taken from an eleventh breast cancer patient as described in Example 4.

Observation of filtered cells from patient Breast-207 demonstrated cells that were DAPI positive (blue channel) and CD45 positive (conjugated with fluorescent dye Cy5 shown as magenta channel), indicating leukocytes, and which had multiple nuclei or irregular nuclei having a dimension greater than 16 µm, and overall cell extant having a dimension greater than 20 µm. A representative image is shown in FIGS. 29A-B. A potential TDMC is identified with dashed ovals. Indication of takeup of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in the composite images and is distinct in the individual channel images.

Example 5: Analysis of Microfiltration-Isolated Cells from an Ovarian Cancer Patient An ovarian cancer patient had their blood drawn, filtered and stained as described in Example 1. The microfilter was scanned at 40× in order to determine whether TDMCs were observed on the microfilter.

Patient Ovarian-101 Cancer Sample 1 was diagnosed with ovarian cancer. Blood was drawn prior to debulking surgery. After blood sample filtering, staining, and microscopic filter membrane imaging at 20× and 40× in a four channel fluorescent microscope, 23 image sets (each image set includes four individual fluorescence channels and a composite) from approximately 660 frame sets were selected for detailed observation. At least 23-27 TDMCs were identified in the images.

Figure 30A:
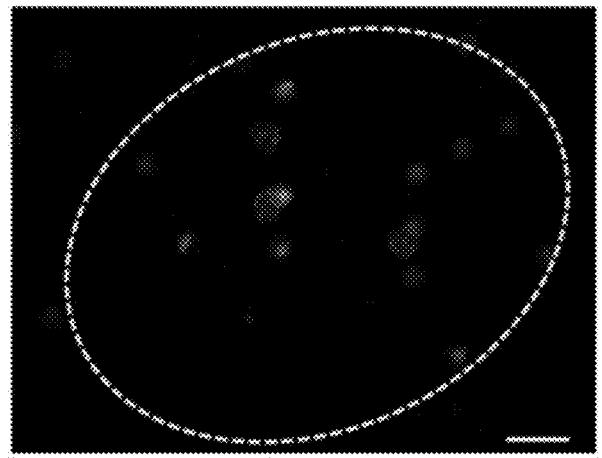
FIG. 30A is a four channel fluoroscopy composite microscope image showing a TDMC from a blood sample taken from an ovarian cancer patient as described in Example 5.
Figure 30B:
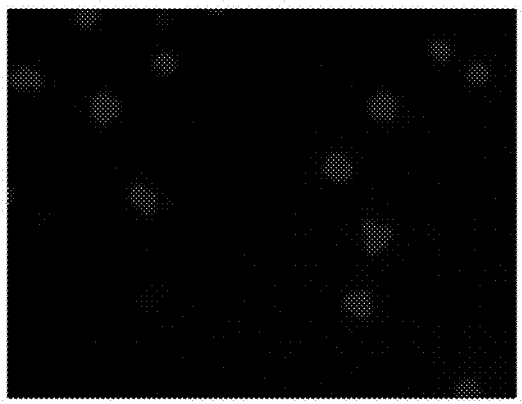
FIG. 30B is a single channel fluorescence DAPI channel image showing a TDMC from a blood sample taken from an ovarian cancer patient as described in Example 5.
Figure 30C:
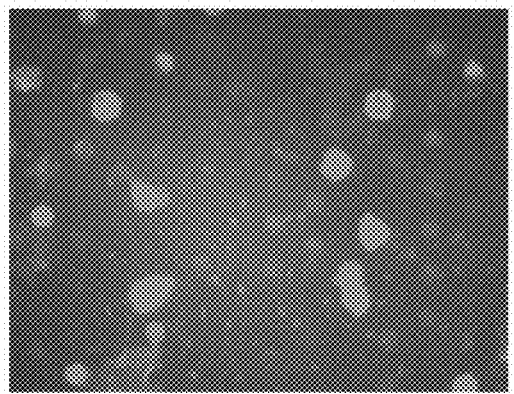
FIG. 30C is a single channel fluorescence FITC channel image showing a signal corresponding to a FITC-anti-Ck 8,18,19 antibody bound to a TDMC from a blood sample taken from an ovarian cancer patient as described in Example 5.
Figure 30D:
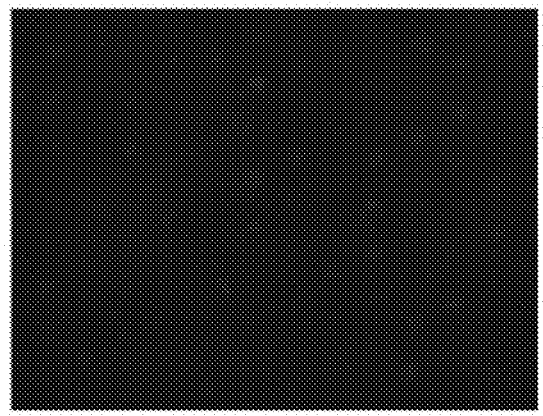
FIG. 30D is a single channel fluorescence TRITC channel image showing a signal corresponding to a TRITC-anti-EpCAM antibody bound to a TDMC from a blood sample taken from an ovarian cancer patient as described in Example 5.
Figure 30E:
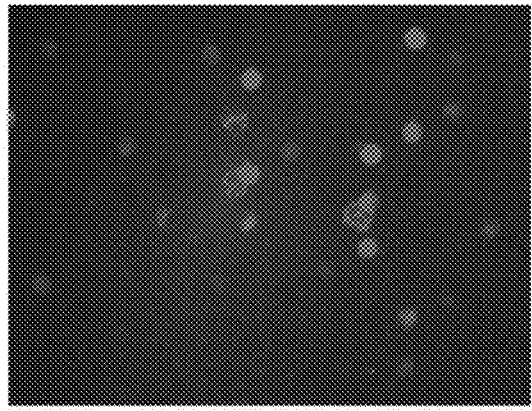
FIG. 30E is a single channel fluorescence Cy5 channel image showing a signal corresponding to a Cy5-anti-CD45 antibody bound to a TDMC from a blood sample taken from an ovarian cancer patient as described in Example 5.
Figure 30F:
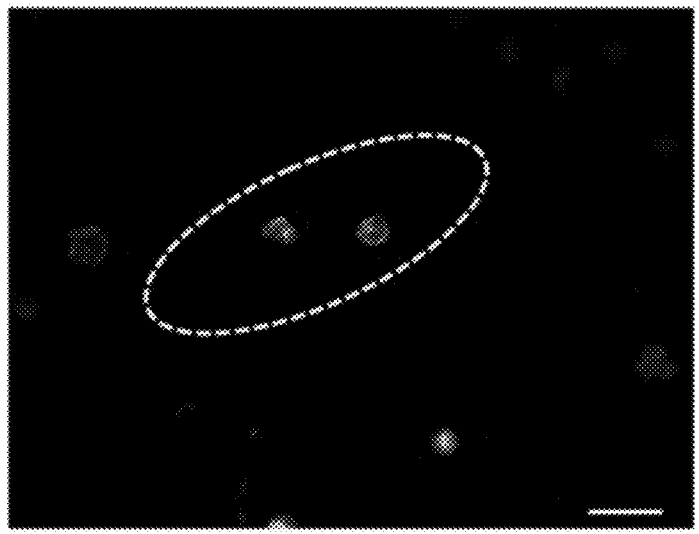
FIG. 30F is a four channel fluoroscopy composite microscope image showing a TDMC from a blood sample taken from an ovarian cancer patient as described in Example 5.
Figure 30G:
FIG. 30G is a single channel fluorescence DAPI channel image showing a TDMC from a blood sample taken from an ovarian cancer patient as described in Example 5.
Figure 30H:
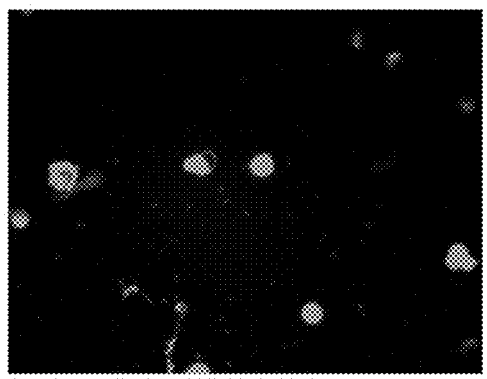
FIG. 30H is a single channel fluorescence FITC channel image showing a signal corresponding to a FITC-anti-Ck 8,18,19 antibody bound to a TDMC from a blood sample taken from an ovarian cancer patient as described in Example 5.
Figure 30I:
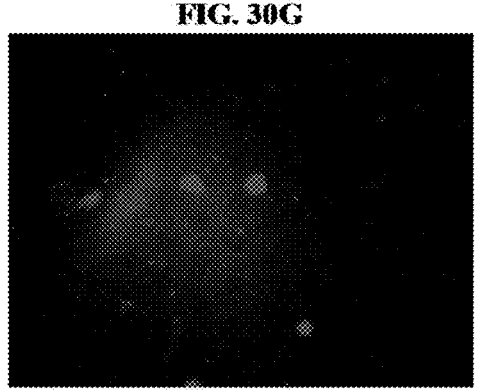
FIG. 30I is a single channel fluorescence TRITC channel image showing a signal corresponding to a TRITC-anti-EpCAM antibody bound to a TDMC from a blood sample taken from an ovarian cancer patient as described in Example 5.
Figure 30J:
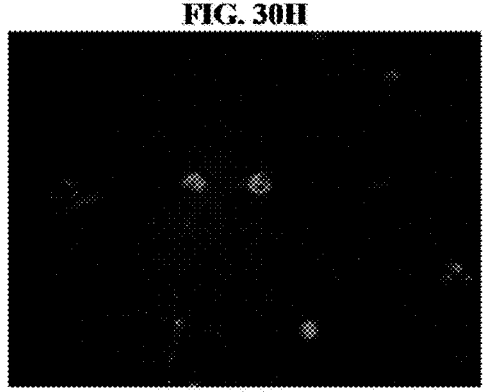
FIG. 30J is a single channel fluorescence Cy5 channel image showing a signal corresponding to a Cy5-anti-CD45 antibody bound to a TDMC from a blood sample taken from an ovarian cancer patient as described in Example 5.
Figure 30K:
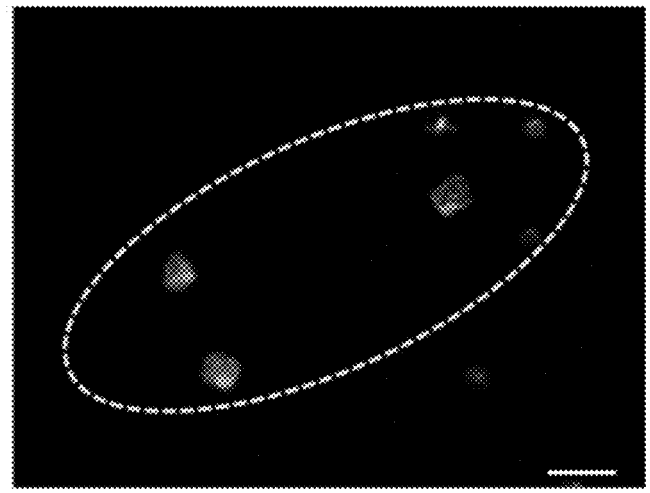
FIG. 30K is a four channel fluoroscopy composite microscope image showing a TDMC from a blood sample taken from an ovarian cancer patient as described in Example 5.
Figure 30L:
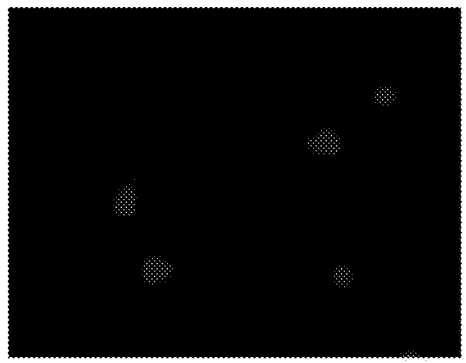
FIG. 30L is a single channel fluorescence DAPI channel image showing a TDMC from a blood sample taken from an ovarian cancer patient as described in Example 5.
Figure 30M:
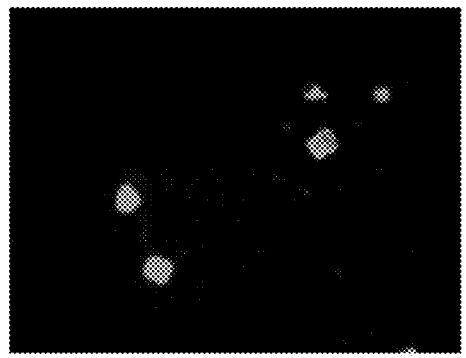
FIG. 30M is a single channel fluorescence FITC channel image showing a signal corresponding to a FITC-anti-Ck 8,18,19 antibody bound to a TDMC from a blood sample taken from an ovarian cancer patient as described in Example 5.
Figure 30N:
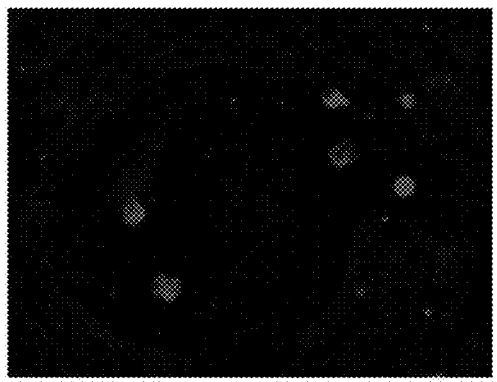
FIG. 30N is a single channel fluorescence Cy5 channel image showing a signal corresponding to a Cy5-anti-CD45 antibody bound to a TDMC from a blood sample taken from an ovarian cancer patient as described in Example 5.
Figure 30O:
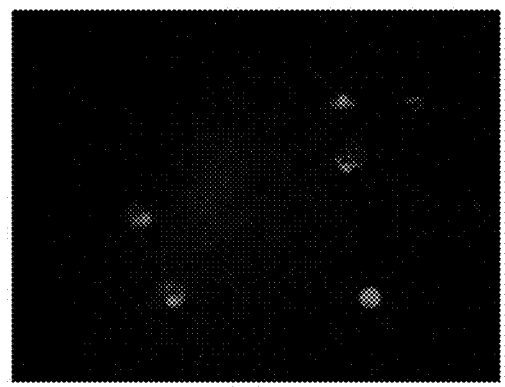
FIG. 30O is a single channel fluorescence Cy5 channel image showing a signal corresponding to a Cy5-anti-CD45 antibody bound to a TDMC from a blood sample taken from an ovarian cancer patient as described in Example 5.

Observation of filtered cells from patient Ovarian-101 demonstrated cells that were DAPI positive (blue channel) and CD45 positive (conjugated with fluorescent dye Cy5 shown as magenta channel), indicating leukocytes, and which had multiple nuclei or irregular nuclei having a dimension greater than 16 µm, and overall cell extant having a dimension greater than 20 µm. A representative image is shown in FIGS. 30A-O. A potential TDMC is identified with dashed ovals. Indication of takeup of anti-EpCAM antibody (conjugated with fluorescent dye TRITC shown as red channel), indicating presence of epithelial tissue, and takeup of anti-Cytokeratins 8,18,19 (conjugated with fluorescent dye FITC shown as green channel), indicating presence of the associated cytokeratins, can be seen in the composite images and is distinct in the individual channel images.

Example 6: Autofluorescence of a Nickel-Palladium Microfilter

Five Corning borosilicate glass microscope slides were prepared having clean nickel-palladium (NiPd) filter membranes placed on them and covered with a borosilicate glass cover slip having a thickness of approximately 0.17 mm. The cover slips were approximately 20 mm square and completely covered the NiPd filter. Similarly, five Corning borosilicate glass microscope slides were prepared having parylene-C membranes approximately 10 um thick placed on them, which were also covered with a borosilicate glass cover slip having a thickness of approximately 0.17 mm. The slides thus prepared were mounted in a microscope slide carrier and secured in the microscope stage for observation and autofluorescence measurement.

Autofluorescence was measured by manually focusing on each sample using brightfield illumination, then exciting each sample at excitation wavelengths of 395 nm, 485 nm, 560 nm, and 640 nm. The excitation source was filtered with bandpass filters having band-pass characteristics of 395 nm+/−12.5 nm, 485 nm+/−12.5 nm, 560 nm+/−16 nm, and 640 nm+/−15 nm. Exposure times of 75 ms, 300 ms, 750 ms, and 300 ms, respectively, were used. Autofluorescent emission filters having bandpass characteristics of 435 nm+/−13 nm, 515 nm+/−15 nm, 595 nm+/−20 nm, and 705 nm+/−36 nm respectively were used to filter each fluorescent channel. The fluorescence signals of 5 samples (numbered 1-5) from each type of filter are shown in Table 1.

TABLE 1

Autofluorescence of NiPd and parylene-C membranes.

| Channel | parylene-C | | | | | NiPd | | | | |
| --- | --- | --- | --- | --- | --- | --- | --- | --- | --- | --- |
| | #1 | #2 | #3 | #4 | #5 | #1 | #2 | #3 | #4 | #5 |
| DAPI | 466 | 382 | 396 | 369 | 370 | 529 | 536 | 476 | 488 | 501 |
| FITC | 2591 | 2557 | 2400 | 2383 | 2440 | 392 | 376 | 377 | 358 | 378 |
| TRITC | 986 | 1009 | 963 | 1009 | 994 | 120 | 123 | 122 | 115 | 122 |
| CY5 | 334 | 368 | 342 | 374 | 339 | 164 | 164 | 168 | 156 | 160 |

The average autofluorescent signal from the NiPd filters were 1.28 times the autofluorescent signal from the parylene-C filter in the DAPI channel, but the autofluorescent signals in the FITC, TRITC, and Cy5 channels were 15%, 12%, and 46% respectively of the autofluorescent signals from the parylene-C sample.

While preferred embodiments of the present disclosure have been shown and described herein, it will be obvious to those skilled in the art that such embodiments are provided by way of example only. Numerous variations, changes, and substitutions will now occur to those skilled in the art without departing from this disclosure.

What is claimed is:

1. A method of determining the presence or absence of a target cell in a biological sample from a subject, the method comprising:
   a) passing the biological sample through a microfilter comprising a metal layer and a plurality of pores extending through the metal layer; wherein a length of one or more of the plurality of pores is smaller than a length of the target cell, and the metal layer comprises nickel;
   b) if the biological sample comprises a cell of interest, retaining the cell of interest on a surface of the metal layer;
   c) applying to the surface of the metal layer a first probe comprising a molecule specific for a biomarker of the target cell; and
   d) if the cell of interest is retained on the surface of the metal layer, determining if the first probe is bound to the cell of interest;
   wherein if the first probe is bound to the cell of interest, the cell of interest is the target cell and the target cell is present in the biological sample from the subject, wherein the first probe comprises a first fluorophore; and
   e) determining if the first probe is bound to the cell of interest using a computer-implemented method comprising:
      (i) transmitting, by a computer, a surface scanning instruction to a multichannel fluorescence acquisition device, wherein the microfilter is positioned on a stage of the multichannel fluorescence acquisition device; the surface scanning instruction comprising one or more commands for the multichannel fluorescence acquisition device to determine the z-axis height of the microfilter surface;
      (ii) transmitting, by a computer, an image capture instruction to the multichannel fluorescence acquisition device, the image capture instruction comprising one or more commands for the multichannel fluorescence acquisition device to acquire a plurality of digital images of the microfilter using a channel corresponding to the first fluorophore, wherein the plurality of digital images are acquired at each stage position in a z-stack having a focus plan centered on the microfilter surface height determined in step (i);
(iii) generating, by a computer, an in-focus image by stitching together in-focus portions of each of multiple images of the plurality of digital images;
(iv) selecting, by a computer, an in-focus image that comprises the cell of interest; and
(v) identifying, by a computer, an area of interest comprising the cell of interest in the in-focus image.

2. The method of claim 1, wherein determining if the first probe is bound to the cell of interest on the surface of the metal layer comprises use of a microscope, wherein the signal from the first probe comprises a fluorescent signal.

3. The method of claim 2, wherein the fluorescent signal of the first probe, bound to the cell of interest, is determined automatically by the computer-implemented method, to determine a location of the cell of interest.

4. The method of claim 1, wherein the cell of interest comprises a Tumor Derived Myeloid Cell (TDMC), Circulating Tumor Cell (CTC), Tumor Associated Macrophage (TAM), or a combination thereof.

5. The method of claim 3, further comprising wherein a user detects the presence or absence of the fluorescent signal by fluorescent microscopy; or both the user and the computer detect the presence or absence of the fluorescent signal.

6. The method of claim 1, comprising determining if the cell of interest is retained on the surface of the metal layer by applying to the surface of the metal layer a second probe comprising a molecule specific for a second biomarker of the cell of interest.

7. The method of claim 6, wherein the second biomarker of the cell of interest is CD45.

8. The method of claim 1, wherein the presence of the target cell in the biological sample is indicative of cancer in the subject.

9. The method of claim 8, wherein the cancer is breast cancer.

10. The method of claim 8, wherein the cancer is ovarian cancer.

11. The method of claim 1, wherein the biomarker of the target cell comprises cytokeratin 8 (Ck8), cytokeratin 18 (Ck18), cytokeratin 19 (Ck19), EpCAM, or a combination thereof.

12. The method of claim 1, comprising applying to the surface of the metal layer a DAPI stain, wherein if the cell of interest is retained on the surface of the metal layer, the nucleus of the cell of interest is stained and viewed by fluorescent microscopy; wherein the cell of interest retained on the surface of the metal layer is the target cell if: (i) the longest diameter of the nucleus of the cell of interest is between about 6 and about 16 microns, (ii) the nucleus of the cell of interest has an irregular form, (iii) the cell of interest comprises multiple nuclei, or (iv) a combination of (i)-(iii).

13. The method of claim 1, comprising applying to the microfilter a second probe comprising a second fluorophore; wherein the computer implemented method further comprises transmitting a scanning instruction comprising one or more commands for the multichannel fluorescence acquisition device to acquire a digital image of the microfilter using a second fluorescent channel corresponding to the second fluorophore.

14. The method of claim 1, further comprising enhancing, by a computer, the visibility of a feature in the acquired digital image.

15. The method of claim 3, wherein determining if the first probe is bound to the cell of interest using a computer-implemented method further comprising:
(i) determining, by a computer, if a signal from the first probe correlates to the location of the cell of interest on the surface of the metal layer in each of the one or more digital images of the microfilter.

16. The method claim 15, wherein the computer determines the presence or absence of the target cell using a software module configured with a trained convolutional neural network (CNN).

17. A method of diagnosing cancer in a subject, the method comprising:
a) passing a biological sample from the subject through a microfilter comprising a metal layer and a plurality of pores extending through the metal layer; wherein a length of one or more of the plurality of pores is smaller than a length of a target cell, and the metal layer has an autofluorescence less than a membrane filter comprising parylene-C in the FITC, TRITC or Cy5 fluorescent channel;
b) if the biological sample comprises the target cell, separating the target cell from the biological sample on a surface of the metal layer, and (i) retaining the target cell on the surface of the metal layer or (ii) collecting the target cell from the surface of the metal layer;
c) applying a probe comprising a molecule specific for a biomarker of the target cell to either (i) the surface of the metal layer or (ii) material collected from the surface of the metal layer; wherein if the biological sample comprises the target cell, the target cell is present on either the surface of the metal layer or the material collected from the surface of the metal layer, and the probe is bound to the target cell, wherein the probe comprises a fluorophore; and
d) determining the presence or absence of the target cell on either (i) the surface of the metal layer or (ii) the material collected from the surface of the metal layer, by detecting the presence, absence, intensity, location, or combination thereof of a signal from the applied probe using a computer-implemented method comprising:
I. transmitting, by a computer, a surface scanning instruction to a multichannel fluorescence acquisition device, wherein the microfilter is positioned on a stage of the multichannel fluorescence acquisition device; the surface scanning instruction comprising one or more commands for the multichannel fluorescence acquisition device to determine the z-axis height of the microfilter surface;
II. transmitting, by a computer, an image capture instruction to the multichannel fluorescence acquisition device, the image capture instruction comprising one or more commands for the multichannel fluorescence acquisition device to acquire a plurality of digital images of the microfilter using a channel corresponding to the fluorophore, wherein the plurality of digital images are acquired at each stage position in a z-stack having a focus plan centered on the microfilter surface height determined in step (I);
III. generating, by a computer, an in-focus image by stitching together in-focus portions of each of multiple images of the plurality of digital images;
IV. selecting, by a computer, an in-focus image that comprises the cell of interest; and
V. identifying, by a computer, an area of interest comprising the cell of interest in the in-focus image;

wherein the presence of the target cell is indicative of cancer in the subject.

18. The method of claim 17, wherein the metal layer comprises nickel, palladium, titanium, gold, silver, cobalt, chromium, copper, iron, manganese, platinum, zinc, molybdenum, tungsten, aluminum, indium, carbon, silicon, tin, lead, or an alloy or combination thereof.

19. The method of claim 17, wherein each of the plurality of pores has a first length between about 1 and about 50 microns.

20. The method of claim 17, wherein the plurality of pores of the microfilter has a density of is between about 1 and about 10,000 pores per square millimeter.

21. The method of claim 17, wherein an edge-to-edge distance between two adjacent pores in the plurality of pores is between about 2 and about 24 microns.

22. The method of claim 17, wherein the microfilter is between about 5 and 100 microns thick.

23. The method of claim 17, wherein the metal layer has an autofluorescence less than 50% of the autofluorescence of the membrane filter comprising parylene-C in the FITC, TRITC or Cy5 fluorescent channel.

24. The method of claim 17, wherein the biomarker is cytokeratin 8, cytokeratin 18, cytokeratin 19, EpCAM, or a combination thereof.

25. The method of claim 17, wherein the cancer is selected from breast cancer and ovarian cancer.

26. The method of claim 17, wherein the biological sample is passed through the microfilter at a rate of between 0.1 and 15 milliliters per minute.

27. The method of claim 17, wherein the biological sample has a volume between about 1 and about 15 milliliters.

28. The method of claim 17, wherein the surface of the metal layer is functionalized with a biomolecule specific for the target cell.

* * * * *

UNITED STATES PATENT AND TRADEMARK OFFICE
CERTIFICATE OF CORRECTION

PATENT NO. : 9,739,783 B1
APPLICATION NO. : 15/209616
DATED : August 22, 2017
INVENTOR(S) : Amit Kumar et al.

Page 1 of 1

It is certified that error appears in the above-identified patent and that said Letters Patent is hereby corrected as shown below:

In the Claims

Column 65, Line 12, Claim 20, please delete "is"

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*